United States Patent
Burns

(10) Patent No.: US 8,809,359 B2
(45) Date of Patent: Aug. 19, 2014

(54) PHENYL AMINO PYRIMIDINE BICYCLIC COMPOUNDS AND USES THEREOF

(71) Applicant: YM Biosciences Australia Pty Ltd, Foster City, CA (US)

(72) Inventor: Christopher John Burns, Caulfield North (AU)

(73) Assignee: YM Biosciences Australia Pty Ltd, Foster City, CA (US)

( * ) Notice: Subject to any disclaimer, the term of this patent is extended or adjusted under 35 U.S.C. 154(b) by 0 days.

(21) Appl. No.: 13/830,152

(22) Filed: Mar. 14, 2013

(65) Prior Publication Data

US 2014/0005161 A1    Jan. 2, 2014

Related U.S. Application Data

(60) Provisional application No. 61/666,725, filed on Jun. 29, 2012.

(51) Int. Cl.
*A01N 43/54* (2006.01)
*A61K 31/505* (2006.01)

(52) U.S. Cl.
USPC ........ 514/275; 514/230.5; 544/105; 544/330; 544/331

(58) Field of Classification Search
CPC ............................ C07D 239/42; A61K 31/506
USPC ................ 544/331, 105, 330; 514/275, 230.5
See application file for complete search history.

(56) References Cited

U.S. PATENT DOCUMENTS

| | | | |
|---|---|---|---|
| 3,481,932 A | 12/1969 | Wagner | |
| 6,600,037 B1 | 7/2003 | Davis et al. | |
| 7,235,588 B2 | 6/2007 | Siddiqui et al. | |
| 7,593,820 B2 | 9/2009 | Wilks et al. | |
| 8,486,941 B2 * | 7/2013 | Burns et al. | 514/235.8 |
| 2002/0147339 A1 | 10/2002 | Batchelor et al. | |
| 2004/0180914 A1 | 9/2004 | Batchelor et al. | |
| 2006/0079543 A1 | 4/2006 | Sum et al. | |
| 2010/0069417 A1 | 3/2010 | Bouaboula et al. | |
| 2014/0005180 A1 * | 1/2014 | Burns et al. | 514/227.8 |
| 2014/0011803 A1 * | 1/2014 | Burns et al. | 514/227.8 |

FOREIGN PATENT DOCUMENTS

| | | | |
|---|---|---|---|
| AU | 2007209928 B2 | 3/2013 | |
| CA | 2507406 A1 | 5/2004 | |
| CN | 1860104 A | 11/2006 | |
| CN | 101600697 A | 12/2009 | |
| JP | 2003-502406 A | 1/2003 | |
| JP | 2006-508107 A | 3/2006 | |
| JP | 2006-512314 A | 4/2006 | |
| JP | 2007-500179 A | 1/2007 | |
| JP | 2009-525337 A | 7/2009 | |
| RU | 2295329 C2 | 3/2007 | |
| WO | WO-97/19065 A1 | 5/1997 | |
| WO | WO-00/78731 A1 | 12/2000 | |
| WO | WO-01/29009 A1 | 4/2001 | |
| WO | WO-02/46171 A2 | 6/2002 | |
| WO | WO-02/46171 A3 | 6/2002 | |
| WO | WO-02/079197 A1 | 10/2002 | |
| WO | WO-03/022244 A1 | 3/2003 | |
| WO | WO-2004/016597 A2 | 2/2004 | |
| WO | WO-2004/016597 A3 | 2/2004 | |
| WO | WO-2004/041789 A1 | 5/2004 | |
| WO | WO-2004/041810 A1 | 5/2004 | |
| WO | WO-2004/041814 A1 | 5/2004 | |
| WO | WO-2005/012262 A1 | 2/2005 | |
| WO | WO-2006/044457 A1 | 4/2006 | |
| WO | WO-2007/089768 A2 | 8/2007 | |
| WO | WO-2007/089768 A3 | 8/2007 | |
| WO | WO-2007/101232 A2 | 9/2007 | |
| WO | WO-2007/101232 A3 | 9/2007 | |
| WO | WO-2008/099074 A1 | 8/2008 | |
| WO | WO 2008109943 A1 * | 9/2008 | |
| WO | WO-2009/029998 A1 | 3/2009 | |
| WO | WO-2009/032861 A1 | 3/2009 | |
| WO | WO-2010/017122 A2 | 2/2010 | |
| WO | WO-2010/017122 A3 | 2/2010 | |
| WO | WO-2012/071612 A1 | 6/2012 | |
| WO | WO-2012/149602 A1 | 11/2012 | |
| WO | WO-2014/000032 A1 | 1/2014 | |

OTHER PUBLICATIONS

A.M. Traynor et al., Drugs of Today, 40(8), 697-710, 698 (2004).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman'S: The Pharmacological Basis of Therapeutics 1315-1403, 1315 (L.L. Brunton et al., eds., 11th ed., 2006).*
I.S. Lucet et al., 107 Blood 176-183 (2006).*
M. Pesu et al., 223 Immunological Reviews, 132-142 (2008).*
A. Pardanani et al., 23 Leukemia, 1441-1445 (2009).*

(Continued)

*Primary Examiner* — Deepak Rao
*Assistant Examiner* — Alexander R Pagano

(57) ABSTRACT

The present invention relates to phenyl amino pyrimidine bicyclic compounds formula I which are inhibitors of protein kinases including JAK kinases. In particular the compounds are active against JAK1, JAK2, JAK3 and TYK2 kinases. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

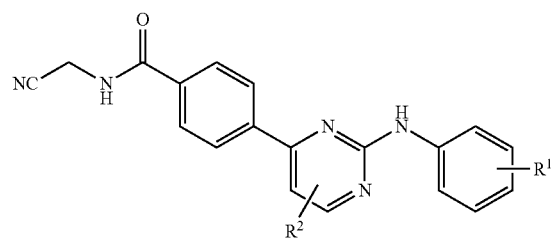

14 Claims, 2 Drawing Sheets

(56) References Cited

OTHER PUBLICATIONS

T. Anastassiadis et al., 29 Nature Biotechnology, 1039-1046 (2011).*
Alas, S. et al. (Jan. 2003). "Inhibition of Constitutive STAT3 Activity Sensitizes Resistant Non-Hodgkin's Lymphoma and Multiple Myeloma to Chemotherapeutic Drug-Mediated Apoptosis," *Clinical Cancer Research* 9:316-326.
Anastassiadis, T. et al. (Nov. 2011, e-pub. Oct. 30, 2011). "Comprehensive Assay of Kinase Catalytic Activity Reveals Features of Kinase Inhibitor Selectivity," *Nature Biotechnology* 29(11):1039-1045.
Berger, L.C. et al. (Jul. 15, 1994). "Tyrosine Phosphorylation of JAK-TYK Kinases in Malignant Plasma Cell Lines Growth-Stimulated by Interleukins 6 and 11," *Biochemical and Biophysical Research Communications* 202(1):596-605.
Burger, R. et al. (Jan. 2009). "Janus Kinase Inhibitor INCB20 has Antiproliferative and Apoptotic Effects on Human Myeloma Cells In Vitro and In Vivo," *Mol Cancer Ther* 8(1):26-35.
Burns, C.J. et al. (2009, e-pub. Aug. 23, 2009). "Phenylaminopyrimidines as Inhibitors of Janus Kinases (JAKs)," *Bioorganic & Medicinal Chemistry Letters* 19:5887-5892.
Chatterjee, M. et al. (Nov. 1, 2002). "In the Presence of Bone Marrow Stromal Cells Human Multiple Myeloma Cells Become Independent of the IL-6/gp130/STAT3 Pathway," *Blood* 100(9):3311-3318.
Chatterjee, M. et al. (Dec. 1, 2004). "Combined Disruption of Both the MEK/ERK and the IL-6R/STAT3 Pathways is Required to Induce Apoptosis of Multiple Myeloma Cells in the Presence of Bone Marrow Stromal Cells," *Blood* 104(12):3712-3721.
Cheung, W.C. et al. (2001). "The Bone Marrow Stromal Microenvironment Influences Myeloma Therapeutic Response In Vitro," *Leukemia* 15:264-271.
Daley, G.Q. et al. (Dec. 1988). "Transformation of an Interleukin 3-Dependent Hematopoietic Cell Line by the Chronic Myelogenous Leukemia-Specific P210$^{bcr/abl}$ Protein," *Proc. Natl. Acad. Sci. USA* 85:9312-9316.
Dalton, W. et al. (Nov. 15, 2006). "Synopsis of a Roundtable on Validating Novel Therapeutics for Multiple Myeloma," *Clinical Cancer Research* 12(22):6603-6610.
De Vos, J. et al. (2000). "JAK2 Tyrosine Kinase Inhibitor Tyrphostin AG490 Downregulates the Mitogen-Activated Protein Kinase (MAPK) and Signal Transducer and Activator of Transcription (STAT) Pathways and Induces Apoptosis in Myeloma Cells," *British Journal Haematology* 109:823-828.
Emanuel, S. et al. (2004). "A Vascular Endothelial Growth Factor Receptor-2 Kinase Inhibitor Potentiates the Activity of the Conventional Chemotherapeutic Agents Paclitaxel and Doxorubicin in Tumor Xenograft Models," *Molecular Pharmacology* 66(3):635-647.
Ferlin, M. et al. (Nov. 2000). "Insulin-Like Growth Factor Induces the Survival and Proliferation of Myeloma Cells Through an Interleukin-6-Independent Transduction Pathway," *British Journal of Haematology* 111(2):626-634.
Ferrajoli, A. et al. (Dec. 1, 2007). "WP1066 Disrupts Janus Kinase-2 and Induces Caspase-Dependent Apoptosis in Acute Myelogenous Leukemia Cells," *Cancer Res* 67(23):11291-11299.
French, J.D. et al. (2003). "Transactivation of gp130 in Myeloma Cells," *The Journal of Immunology* 170:3717-3723.
GenBank Accession No. NP_004963, last updated on Feb. 2, 2014, located at http://www.ncbi.nlm.nih.gov/protein/NP_004963, last visited on Feb. 5, 2014, 7 pages.
Gómez-Benito, M. et al. (2007, e-pub. Dec. 8, 2006). "Mechanism of Apoptosis Induced by IFN-α in Human Myeloma Cells: Role of Jak1 and Bim and Potentiation by Rapamycin," *Cellular Signaling* 19:844-854.
Gust, R. et al. (Jan.-Feb. 2001). "Vascular Remodeling in Experimentally Induced Subacute Canine Pulmonary Hypertension," *Experimental Lung Research* 27:1-12.
Hartwig, J.F. (1998). "Transition Metal Catalyzed Synthesis of Arylamines and Aryl Ethers from Aryl Halides and Triflates: Scope and Mechanism," *Angew. Chem. Int. Ed.* 37:2046-2067.

Hata, H. et al. (Jun. 15, 1993). "Interleukin-6 Gene Expression in Multiple Myeloma: A Characteristic of Immature Tumor Cells," *Blood* 81(12):3357-3364.
Jelinek, D.F. et al. (Nov. 1, 1993). "Coexistence of Aneuploid Subclones Within a Myeloma Cell Line That Exhibits Clonal Immunoglobulin Gene Rearrangement: Clinical Implications," *Cancer Research* 53:5320-5327.
Khong, T. et al. (2008). "The Effect of Azacitidine on Interleukin-6 Signaling and Nuclear FactorκB Activation and Its In Vitro and In Vivo Activity Against Multiple Myeloma," *Haematologica* 93(6):860-869.
Klein, B. et al. (Feb. 1989). "Paracrine Rather Than Autocrine Regulation of Myeloma-Cell Growth and Differentiation by Interleukin-6," *Blood* 73(2):517-526.
Kralovics, R. et al. (Apr. 28, 2005). "A Gain-of-Function Mutation of JAK2 in Myeloproliferative Disorders," *The New England Journal of Medicine* 352(17):1779-1790.
Kumada, M. et al. (1988). "Phosphine-Nickel Complex Catalyzed Cross-Coupling of Grignard Reagents with Aryl and Alkenyl Halides: 1,2-Dibutylbenzene," *Organic Syntheses Collective* vol. 6, pp. 407-411.
Kumar, S. et al. (2005, e-pub. Jun. 16, 2005). "CD45 Expression by Bone Marrow Plasma Cells in Multiple Myeloma: Clinical and Biological Correlations," *Leukemia* 19:1466-1470.
Levine, R.L. et al. (Apr. 2005). "Activating Mutation in the Tyrosine Kinase JAK2 in Polycythemia Vera, Essential Thrombocythemia, and Myeloid Metaplasia with Myelofibrosis," *Cancer Cell* 7:387-397.
Li, J. et al. (Jan. 2010). "INCB16562, a JAK1/2 Selective Inhibitor, Is Efficacious Against Multiple Myeloma Cells and Reverses the Protective Effects of Cytokine and Stromal Cell Support," *Neoplasia* 12(1):28-38.
March, J. (1992). "Aliphatic Nucleophilic Substitution," in *Advanced Organic Chemistry: Reactions, Mechanisms, and Structure*, 4th Edition, John Wiley & Sons, New York, pp. 352-357.
Mashkovskiy, M.D. (1993). "Lekarstvennyye Sredstva," *Moscow Meditsina* Part 1, p. 8, with English Translation.
Miyaura, N. et al. (1995). "Palladium-Catalyzed Cross-Coupling Reactions of Organoboron Compounds," *Chem. Rev.* 95(7):2457-2483.
Monaghan, K. et al. (2011, e-pub. Nov. 12, 2009). "CYT997 Causes Apoptosis in Human Multiple Myeloma," *Invest New Drugs* 29:232-238.
Moreau, P. et al. (May 2004). "Patients with CD45 Negative Multiple Myeloma Receiving High-Dose Therapy Have a Shorter Survival than those with CD45 Positive Multiple Myeloma," *Haematologica* 89(5):547-551.
Moreaux, J. et al. (Apr. 15, 2004). "BAFF and APRIL Protect Myeloma Cells from Apoptosis Induced by Interleukin 6 Deprivation and Dexamethasone," *Blood* 103(8):3148-3157.
Mullighan, C.G. et al. (Jun. 9, 2009). "JAK Mutations in High-Risk Childhood Acute Lymphoblastic Leukemia," *PNAS* 106(23):9414-9418.
Negishi, E. (Jul. 1, 2002). "A Genealogy of Pd-Catalyzed Cross-Coupling," *Journal of Organometallic Chemistry* 653:34-40.
Pardanani, A. et al. (2010). "A Phase I/II Study of CYT387, an Oral JAK-1/2 Inhibitor, in Myelofibrosis: Significant Response Rates in Anemia, Splenomegaly, and Constitutional Symptoms," *Blood* (*ASH Annual Meeting Abstracts*) 116:Abstract 460.
Pedranzini, L. et al. (Oct. 1, 2006). "Pyridone 6, a Pan-Janus-Activated Kinase Inhibitor, Induces Growth Inhibition of Multiple Myeloma Cells," *Cancer Res* 66(19):9714-9721.
Perez, L.E. et al. (2008). "Bone Marrow Stroma Confers Resistance to Apo2 Ligand/TRAIL in Multiple Myeloma in Part by Regulating c-FLIP," *The Journal of Immunology* 180:1545-1555.
Puthier, D. et al. (1999). "IL-6 Up-Regulates Mcl-1 in Human Myeloma Cells Through JAK/STAT Rather Than Ras/MAP Kinase Pathway," *Eur. J. Immunol.* 29:3945-3950.
Rane, S.G. et al. (2000). "Janus Kinases: Components of Multiple Signaling Pathways," *Oncogene* 19:5662-5679.
Scott, L.M. et al. (Feb. 1, 2007). "JAK2 Exon 12 Mutations in Polycythemia Vera and Idiopathic Erythrocytosis," *The New England Journal of Medicine* 356(5):459-468.

(56) References Cited

OTHER PUBLICATIONS

Scuto, A. et al. (2011, e-pub. Dec. 17, 2010). "The Novel JAK Inhibitor AZD1480 Blocks STAT3 and FGFR3 Signaling, Resulting in Suppression of Human Myeloma Cell Growth and Survival," *Leukemia* 25:538-550.

Stille, J.K. (1986). "The Palladium-Catalyzed Cross-Coupling Reactions of Organotin Reagents with Organic Electrophiles," *Angew. Chem. Int. Ed. Engl.* 25:508-524.

Taylor, H.E. et al. (Jan. 1998, e-pub. Jan. 2, 1998). "1-Alkylcarbonyloxymethyl Prodrugs of 5-Fluorouracil (5-FU): Synthesis, Physicochemical Properties, and Topical Delivery of 5-FU," *Journal of Pharmaceutical Sciences* 87(1):15-20.

Thabard, W. et al. (Jun. 21, 2001). "IL-6 Upregulates Its Own Receptor on Some Human Myeloma Cell Lines," *Cytokine* 14(6):352-356.

Tyner, J.W. et al. (Jun. 24, 2010). "CYT387, a Novel JAK2 Inhibitor, Induces Hematologic Responses and Normalizes Inflammatory Cytokines in Murine Myeloproliferative Neoplasms," *Blood* 115(25):5232-5240.

Tyukavkina, N.A. et al. (2005). Bioorganicheskaya Khimiya, 4$^{th}$ Edition, Moscow, Drofa, pp. 83-85, with English Translation.

Vannucchi, A.M. et al. (May/Jun. 2009). "Advances in Understanding and Management of Myeloproliferative Neoplasms," *CA Cancer J Clin* 59(3):171-191.

Wheelhouse, R.T. et al. (2006). "Design, Synthesis, and Evaluation of Novel Biarylpyrimidines: A New Class of Ligand for Unusual Nucleic Acid Structures," *J. Med. Chem.* 49(17):5187-5198.

YM BioSciences Inc. (Nov. 8, 2010). "YM Biosciences Reports Significant Response Rates in Anemia, Splenomegaly, and Constitutional Symptoms from the Phase I/II Trial of Its JAK1/JAK2 Inhibitor, CYT387, in Myelofibrosis,"Results to be presented at the 52$^{nd}$ American Society of Hematology Annual Meeting, Orlando, Florida, Dec. 4-7, 2010, Press Release, retrieved from http://www.prnewswire.com/news-releases/ym-biosciences-reports-significant-response-rates-in-anemia-splenomegaly-and-constitutional-symptoms-from-the-phase-iii-trial-of-its-jak1jak2-inhibitor-cyt387-in-myelofibrosis-106893443.html, last visited on Feb. 4, 2014, 4 pages.

Zhang, X.G. et al. (Jun. 15, 1994). "Reproducible Obtaining of Human Myeloma Cell Lines as a Model for Tumor Stem Cell Study in Human Multiple Myeloma," *Blood* 83(12):3654-3663.

Non-Final Office Action mailed on Aug. 14, 2012 for U.S. Appl. No. 12/530,610, filed Mar. 19, 2010, 7 pages.

Final Office Action mailed on Dec. 13, 2012 for U.S. Appl. No. 12/530,610, filed Mar. 19, 2010, 9 pages.

Notice of Allowance mailed on Mar. 7, 2013 for U.S. Appl. No. 12/530,610, filed Mar. 19, 2010, 10 pages.

Notice of Allowance (Supplemental) mailed on Apr. 25, 2013 for U.S. Appl. No. 12/530,610, filed Mar. 19, 2010, 6 pages.

International Search Report mailed on May 15, 2008 for PCT Patent Application No. PCT/AU2008/000339, filed Mar. 12, 2008, 4 pages.

Written Opinion mailed on May 15, 2008 for PCT Patent Application No. PCT/AU2008/000339, filed Mar. 12, 2008, 9 pages.

Extended Search Report mailed on May 25, 2011 for European Patent Application No. 08714386.3, 10 pages.

Australian Office Action mailed on Oct. 24, 2011 for Australian Patent Application No. 2008226327, 4 pages.

Chinese First Office Action mailed on Sep. 22, 2011 for Chinese Patent Application No. 200880015782.9, 24 pages.

Chinese Second Office Action mailed on Jun. 12, 2012 for Chinese Patent Application No. 200880015782.9, 7 pages.

Chinese Third Office Action mailed on Dec. 17, 2012 for Chinese Patent Application No. 200880015782.9, 8 pages.

Chinese Fourth Office Action mailed on Sep. 3, 2013 for Chinese Patent Application No. 200880015782.9, 6 pages.

Chinese Fifth Office Action mailed on Nov. 21, 2013 for Chinese Patent Application No. 200880015782.9, 4 pages.

Indonesian Office Action mailed on Apr. 30, 2013 for Indonesian Patent Application No. W-00200902848, 2 pages.

Japanese Office Action mailed on Mar. 19, 2013 for Japanese Patent Application No. 2009-552972, 8 pages.

Japanese Office Action mailed on Oct. 15, 2013 for Japanese Patent Application No. 2009-552972, 3 pages.

Mexican Office Action mailed on Oct. 31, 2013 for Mexican Patent Application No. MX/a/2009/009792, 3 pages.

Russian Office Action mailed Jan. 26, 2012 for Russian Patent Application No. 2009137363/01(052832), 8 pages.

Russian Office Action mailed Dec. 11, 2012 for Russian Patent Application No. 2009137363/04(052832), 12 pages.

International Search Report mailed on Feb. 21, 2012 for PCT Patent Application No. PCT/AU2011/001551, filed Nov. 29, 2011, 7 pages.

Written Opinion mailed on Feb. 21, 2012 for PCT Patent Application No. PCT/AU2011/001551, filed Nov. 29, 2011, 8 pages.

International Search Report mailed on May 22, 2012 for PCT Patent Application No. PCT/AU2012/000462, filed May 1, 2012, 2 pages.

Written Opinion mailed on May 22, 2012 for PCT Patent Application No. PCT/AU2012/000462, filed May 1, 2012, 3 pages.

International Search Report mailed on Sep. 6, 2013 for PCT Patent Application No. PCT/AU2013/000687, filed Jun. 26, 2013, 4 pages.

U.S. Appl. No. 13/991,139, filed Nov. 15, 2013 by Smith et al.

U.S. Appl. No. 14/115,084, filed May 1, 2012 by Burns et al.

\* cited by examiner

Fig. 1

PHENYL AMINO PYRIMIDINE BICYCLIC COMPOUNDS AND USES THEREOF

CROSS-REFERENCE TO RELATED APPLICATIONS

This application claims priority from U.S. provisional application 61/666,725 filed 29 Jun. 2012. The contents of this document are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699992002100SeqList.txt, date recorded: Jun. 19, 2013, size: 10,494 bytes).

FIELD

The present invention relates to phenyl amino pyrimidine bicyclic compounds which are inhibitors of protein kinases, including JAK kinases. In particular the compounds are active against JAK1, JAK2, JAK3 and TYK2 kinases. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

BACKGROUND

JAKs are kinases which phosphorylate a group of proteins called Signal Transduction and Activators of Transcription or STATs. When phosphorylated, STATs dimerize, translocate to the nucleus and activate expression of genes which lead to, amongst other things, cellular proliferation.

The central role played by the JAK family of protein tyrosine kinases in the cytokine dependent regulation of both proliferation and end function of several important cell types indicates that agents capable of inhibiting the JAK kinases are useful in the prevention and chemotherapeutic treatment of disease states dependent on these enzymes. Potent and specific inhibitors of each of the currently known four JAK family members will provide a means of inhibiting the action of the cytokines that drive immunological and inflammatory diseases and hyperproliferine diseases such as cancer.

Myeloproliferative disorders (MPD) include, among others, polycythemia vera (PV), primary myelofibrosis, thrombocythemia, essential thrombocythemia (ET), idiopathic myelofibrosis (IMF), chronic myelogenous leukemia (CML), systemic mastocystosis (SM), chronic neutrophilic leukemia (CNL), myelodisplastic syndrome (MDS) and systemic mast cell disease (SMCD). JAK2 is a member of the JAK family of kinases in which a specific mutation (JAK2V617F) has been found in 99% of polycythemia vera (PV) patients and 50% of essential thrombocytopenia (ET) and idiopathic myelofibrosis (MF). This mutation is thought to activate JAK2, giving weight to the proposition that a JAK2 inhibitor will be useful in treating these types of diseases.

Asthma is a complex disorder characterized by local and systemic allergic inflammation and reversible airway obstruction. Asthma symptoms, especially shortness of breath, are a consequence to airway obstruction, and death is almost invariably due to asphyxiation. Airway Hyper Responsiveness (AHR), and mucus hyper secretion by goblet cells are two of the principle causes of airway obstruction in asthma patients. Intriguingly recent work in animal experimental models of asthma has underscored the importance of IL-13 as a key player in the pathology of asthma. Using a specific IL-13 blocker, it has been demonstrated that IL-13 acts independently of IL-4 and may be capable of inducing the entire allergic asthma phenotype, without the induction of IgE (i.e. in a non-atopic fashion). This and other models have pointed to an important second tier mechanism for eliciting the pathophysiology of asthma, that is not dependent on the production of IgE by resident B-cells or the presence of eosinophils. A direct induction of AHR by IL-13, represents an important process that is likely to be an excellent target for intervention by new therapies. A contemplated effect of a JAK1, JAK2 and/or TYK2 inhibitor to the lungs would result in the suppression of the local release of IL-13 mediated IgE production, and therefore reduction in histamine release by mast cells and eosinophils. This and other consequences of the absence of IL-13 indicate that many of the effects of asthma may be alleviated through administration of a JAK1, JAK2 and/or TYK2 inhibitor to the lungs.

Chronic Obstructive Pulmonary Disease (COPD) is a term which refers to a large group of lung diseases which can interfere with normal breathing. Current clinical guidelines define COPD as a disease state characterized by airflow limitation which is not fully reversible. The airflow limitation is usually both progressive and associated with an abnormal inflammatory response of the lungs to noxious particles and gases, particularly cigarette smoke and pollution. Several studies have pointed to an association between increased production of IL-13 and COPD, lending support to the proposition that the potential alleviation of asthma symptoms by use of a JAK2 inhibitor, may also be achieved in COPD. COPD patients have a variety of symptoms including cough, shortness of breath, and excessive production of sputum. COPD includes several clinical respiratory syndromes including chronic bronchitis and emphysema.

Chronic bronchitis is a long standing inflammation of the bronchi which causes increased production of mucus and other changes. The patient's symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Additionally, there is evidence of STAT activation in malignant tumors, among them lung, breast, colon, ovarian, prostate and liver cancer, as well as Hodgkins lymphoma, multiple myeloma and hepatocellular carcinoma. Chromosomal translocations involving JAK2 fusions to Tel, Bcr and PCM1 have been described in a number of hematopoietic malignancies including chronic myelogenous leukemia (CML), acute myelogenous leukemia (AML), chronic eosinophilic leukemia (CEL), myelodisplastic syndrome (MDS), myeloproliferative disease (MPD) and acute lymphocytic leukemia (ALL). This suggests treatment of hyperproliferative disorders such as cancers including multiple myeloma; prostate, breast and lung cancer; Hodgkin's Lymphoma; CML; AML; CEL; MDS; ALL; B-cell Chronic Lymphocytic Leukemia; metastatic melanoma; glioma; and hepatoma, by JAK inhibitors is indicated.

Potent inhibitors of JAK2, in addition to the above, will also be useful in vascular disease such as hypertension, hypertrophy, cardiac ischemia, heart failure (including systolic heart failure and diastolic heart failure), migraine and related cerebrovascular disorders, stroke, Raynaud's phenomenon, POEMS syndrome, Prinzmetal's angina, vasculitides, such as Takayasu's arteritis and Wegener's granulomatosis, peripheral arterial disease, heart disease and pulmonary arterial hypertension.

Pulmonary arterial hypertension (PAH) is a pulmonary vascular disease affecting the pulmonary arterioles resulting in an elevation in pulmonary artery pressure and pulmonary vascular resistance but with normal or only mildly elevated left-sided filling pressures. PAH is caused by a constellation of diseases that affect the pulmonary vasculature. PAH can be caused by or associated with collagen vascular disorders such as systemic sclerosis (scleroderma), uncorrected congenital heart disease, liver disease, portal hypertension, HIV infection, Hepatitis C, certain toxins, splenectomy, hereditary hemorrhagic teleangiectasia, and primary genetic abnormalities. In particular, a mutation in the bone morphogenetic protein type 2 receptor (a TGF-b receptor) has been identified as a cause of familial primary pulmonary hypertension (PPH). It is estimated that 6% of cases of PPH are familial, and that the rest are "sporadic." The incidence of PPH is estimated to be approximately 1 case per 1 million population. Secondary causes of PAH have a much higher incidence. The pathologic signature of PAH is the plexiform lesion of the lung which consists of obliterative endothelial cell proliferation and vascular smooth muscle cell hypertrophy in small precapillary pulmonary arterioles. PAH is a progressive disease associated with a high mortality. Patients with PAH may develop right ventricular (RV) failure. The extent of RV failure predicts outcome. The JAK/STAT pathway has recently been implicated in the pathophysiology of PAH. JAKs are kinases which phosphorylate a group of proteins called Signal Transduction and Activators of Transcription or STATs. When phosphorylated, STATs dimerize, translocate to the nucleus and activate expression of genes which lead to proliferation of endothelial cells and smooth muscle cells, and cause hypertrophy of cardiac myocytes. There are three different isoforms of JAK: JAK1, JAK2, and JAK3. Another protein with high homology to JAKs is designated Tyk2. An emerging body of data has shown that the phosphorylation of STAT3, a substrate for JAK2, is increased in animal models of PAH. In the rat monocrotaline model, there was increased phosphorylation of the promitogenic transcription factor STAT3. In this same study pulmonary arterial endothelial cells (PAECs) treated with monocrotaline developed hyperactivation of STAT3. A promitogenic agent or protein is an agent or protein that induces or contributes to the induction of cellular proliferation. Therefore, one effect of JAK2 inhibition would be to decrease proliferation of endothelial cells or other cells, such as smooth muscle cells. A contemplated effect of a JAK2 inhibitor would be to decrease the proliferation of endothelial cells or other cells which obstruct the pulmonary arteriolar lumen. By decreasing the obstructive proliferation of cells, a JAK2 inhibitor could be an effective treatment of PAH.

Additionally the use of JAK kinase inhibitors for the treatment of viral diseases and metabolic diseases is indicated.

Although the other members of the JAK family are expressed by essentially all tissues, JAK3 expression appears to be limited to hematopoetic cells. This is consistent with its essential role in signalling through the receptors for IL-2, IL4, IL-7, IL-9 and IL-15 by non-covalent association of JAK3 with the gamma chain common to these multichain receptors. Males with X-linked severe combined immunodeficiency (XSCID) have defects in the common cytokine receptor gamma chain (gamma c) gene that encodes a shared, essential component of the receptors of interleukin-2 (IL-2), IL-4, IL-7, IL-9, and IL-15. An XSCID syndrome in which patients with either mutated or severely reduced levels of JAK3 protein has been identified, suggesting that immunosuppression should result from blocking signalling through the JAK3 pathway. Gene Knock out studies in mice have suggested that JAK3 not only plays a critical role in B and T lymphocyte maturation, but that JAK3 is constitutively required to maintain T cell function. Taken together with the biochemical evidence for the involvement of JAK3 in signalling events downstream of the IL-2 and IL-4 receptor, these human and mouse mutation studies suggest that modulation of immune activity through the inhibition of JAK3 could prove useful in the treatment of T-cell and B-cell proliferative disorders such as transplant rejection and autoimmune diseases.

Although the inhibition of various types of protein kinases, targeting a range of disease states, is clearly beneficial, it has been to date demonstrated that the identification of a compound which is selective for a protein kinase of interest, and has good "drug like" properties such as high oral bioavailability, is a challenging goal. In addition, it is well established that the predictability of inhibition, or selectivity, in the development of kinase inhibitors is quite low, regardless of the level sequence similarity between the enzymes being targeted.

JAK1, in combination with JAK2 is involved in the transduction of signals downstream of the IL-6, IL-11 and IFN-γ receptors amongst others. JAK1, in combination with JAK3, is essential for signal transduction downstream of IL-2, IL-4, IL-7, IL-9 and IL-15 receptors amongst others. JAK1, in combination with TYK2, is responsible for signal transduction downstream of IL-10, IL-22 and IFN-α receptors amongst others. TYK2 is involved in the transduction of signals downstream of the IL-12 and IL-23 receptors amongst others. IFNγ production by T cells, mediated by IL-12 signalling, is highly dependent on TYK2. These cytokines and receptors are involved in pro-inflammatory responses associated with immunological diseases. Thus inhibition of JAK1 has potential for treating diseases such as rheumatoid arthritis, multiple sclerosis, psoriasis and Crohn's disease.

The challenges in developing therapeutically appropriate JAK inhibitors for use in treatment kinase associated diseases such as immunological and inflammatory diseases including organ transplants; hyperproliferative diseases including cancer and myeloproliferative diseases; viral diseases; metabolic diseases; and vascular diseases include designing a compound with appropriate specificity which also has good druglikeness.

There is therefore a continuing need to design and/or identify compounds which specifically inhibit the JAK family of kinases, and particularly compounds which are active against JAK1, JAK2, JAK3 and TYK2 kinases. There is a need for such compounds for the treatment of a range of diseases.

SUMMARY

In a first aspect, there is provided a compound of formula I

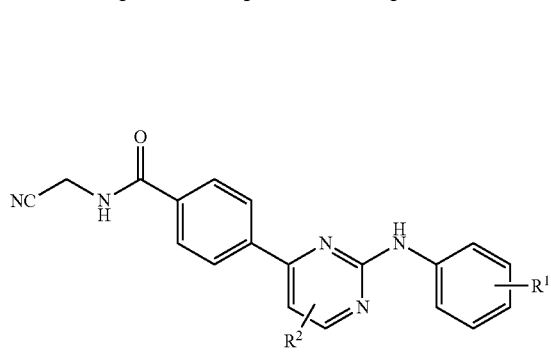

wherein
$R^1$ is a substituted or unsubstituted bicyclic heterocyclyl;
$R^2$ is selected from H, halogen, substituted or unsubstituted $C_{1-4}$ alkyl, $CF_3$ substituted or unsubstituted $C_{1-4}$ alkoxy, $CON(R)_2$, CN and $CO_2R$;
R is selected from H and substituted or unsubstituted $C_{1-4}$ alkyl,
or an enantiomer thereof, a prodrug thereof or a pharmaceutically acceptable salt thereof.

In a second aspect, there is provided a process for the preparation of the compound of formula I defined above which comprises coupling a compound of formula II

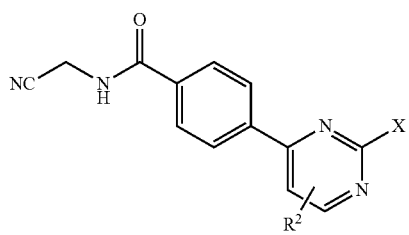

wherein
$R^2$ is defined above and X is a leaving group with a compound of formula III

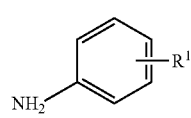

wherein
$R^1$ is defined above; and
M is B or a metal such as Sn, Zn or Mg; or coupling a compound of formula IV

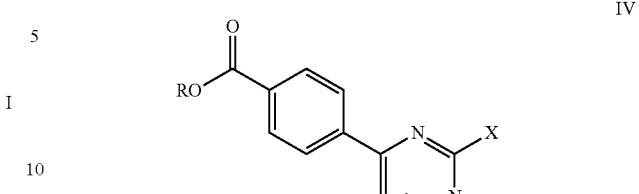

wherein
$R^2$, X and R are as defined above with a compound of formula III as defined above to prepare a compound of formula V

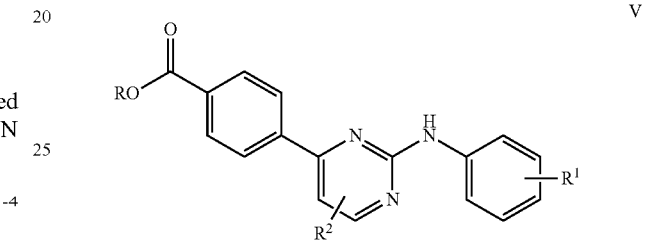

wherein
$R^1$, $R^2$, X and R are as defined above; and
coupling the compound of formula V defined above with

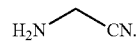

In a third aspect, there is provided the compound of formula V defined above.

The compounds of formula I are kinase inhibitors, preferably JAK inhibitors, more preferably JAK1, JAK2, JAK3 and TYK2 kinase inhibitors. These compounds are useful in the treatment of kinase associated diseases such as immunological and inflammatory diseases including organ transplants; hyperproliferative diseases including cancer and myeloproliferative diseases; viral diseases; metabolic diseases; and vascular diseases.

In a fourth aspect, there is provided a pharmaceutical agent or metabolites thereof comprising the compound of formula I defined above.

There is also provided use of the compound of formula I as a pharmaceutical agent or metabolites thereof.

There is further provided the compound of formula I defined above for use as a pharmaceutical agent or metabolites thereof.

In a fifth aspect, there is provided a kinase inhibitor comprising the compound formula I defined above.

There is also provided use of the compound of formula I defined above as a kinase inhibitor.

There is further provided the compound of formula I defined above for use as a kinase inhibitor.

In a sixth aspect, there is provided a compound of formula I defined above for use as a pharmaceutical agent or metabolites thereof, preferably a kinase inhibitor, more preferably a JAK kinase inhibitor, most preferably a JAK1, JAK2, JAK3 and TYK2 kinase inhibitor.

The compound of formula I may also be administered in the form of a pharmaceutical composition together with a pharmaceutically acceptable carrier.

In a seventh aspect, there is provided a pharmaceutical composition comprising the compound of formula I defined above and a pharmaceutically acceptable carrier.

In one embodiment, the pharmaceutical composition also comprises one or more additional therapeutic agents.

The compound of formula I may be contained within or attached to an implant, such as a drug eluting stent. For example, when the compound is used for the treatment of pulmonary arterial hypertension (PAH), the compound may be contained within or attached to a pulmonary artery stent, which may act locally, or be released from the stent into the pulmonary circulation where the compound exerts its therapeutic activity in the pulmonary vasculature.

In a eighth aspect, there is provided an implant which comprises the compound of formula I defined above.

In an ninth aspect, there is provided a method for the treatment of kinase associated diseases such as immunological and inflammatory diseases including organ transplants; hyperproliferative diseases including cancer and myeloproliferative diseases; viral diseases; metabolic diseases; and vascular diseases which comprises administering an effective amount of the compound of formula I or a pharmaceutical composition defined above to a subject in need thereof.

There is also provided use of the compound of formula I or a pharmaceutical composition as defined above in the manufacture of a medicament for the treatment of kinase associated diseases such as immunological and inflammatory diseases including organ transplants; hyperproliferative diseases including cancer and myeloproliferative diseases; viral diseases; metabolic diseases; and vascular diseases.

There is further provided use of the compound of formula I or a pharmaceutical composition as defined above in the treatment of kinase associated diseases such as immunological and inflammatory diseases including organ transplants; hyperproliferative diseases including cancer and myeloproliferative diseases; viral diseases; metabolic diseases; and vascular diseases.

There is still further provided the compound of the formula I or a pharmaceutical composition defined above for use in the treatment of kinase associated diseases such as immunological and inflammatory diseases including organ transplants; hyperproliferative diseases including cancer and myeloproliferative diseases; viral diseases; metabolic diseases; and vascular diseases.

In a tenth aspect, there is provided a method of inhibiting a kinase in a cell comprising contacting the cell with the compound of formula I defined above.

BRIEF DESCRIPTION OF THE FIGURES

Figure 1:
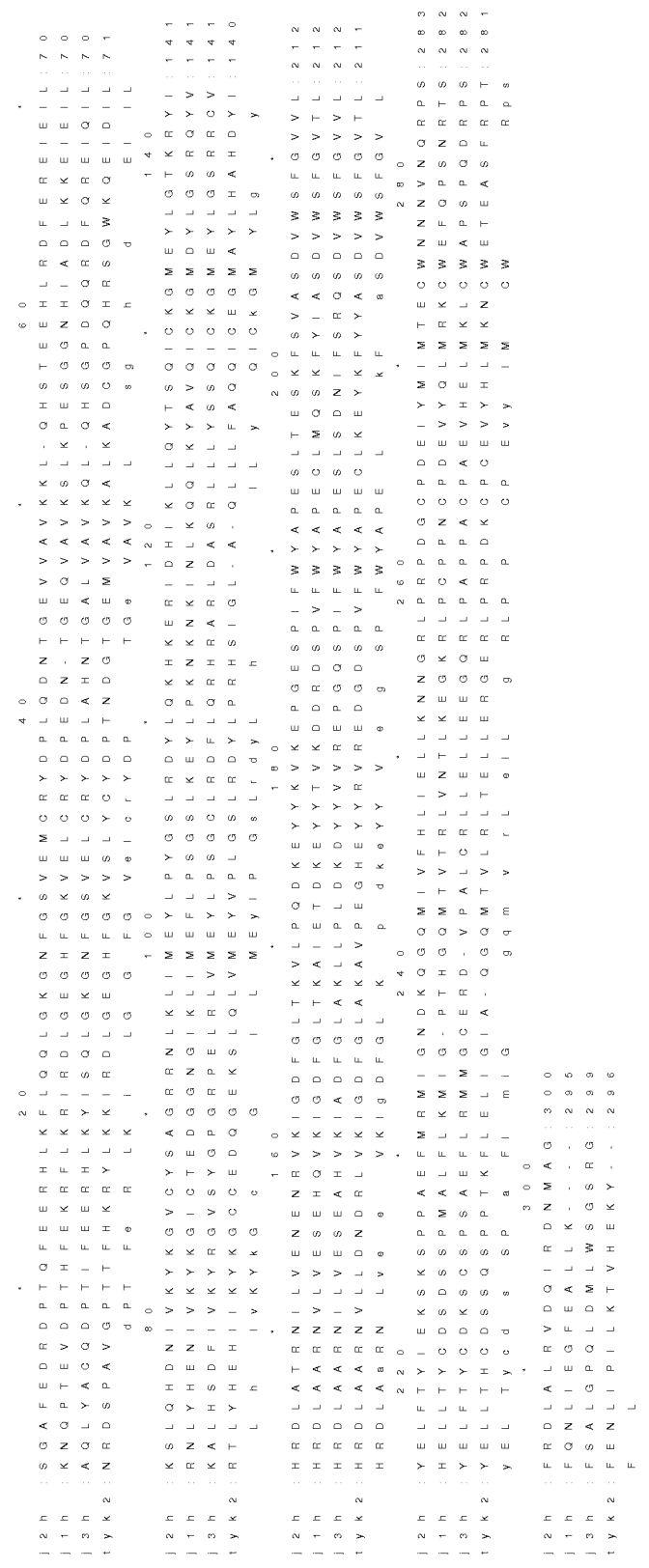

FIG. 1 shows the amino acid sequence alignment of selected JAK Kinases. The sequences shown are j2h=JAK2 (SEQ. ID. NO. 1), j1h=JAK1 (SEQ. ID, NO. 2), j3h=JAK3 (SEQ. ID. NO. 3), and tyk2=TYK2 (SEQ. ID. NO. 4). The sequences are numbered with position 1 starting at amino acid 833 of the JAK2 sequence (taken from Genbank sequence NP_004963) and ends at the C-terminal amino acid. The sequences shown correspond to the C-terminal kinase domain.

DETAILED DESCRIPTION

Figure 2:
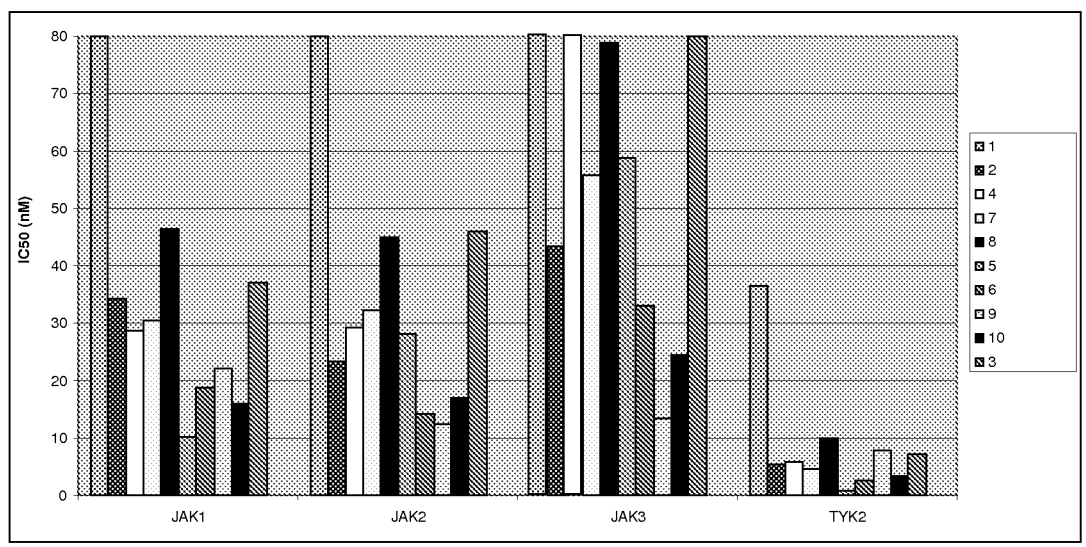
FIG. 2 is a graph showing the IC50 (nM) data for compounds 1-10.

The present invention relates to compounds of formula I which inhibit kinases, in particular JAK kinases such as JAK1, JAK2, JAK3 and TYK2 and are useful in the treatment of kinase associated diseases such as immunological and inflammatory diseases including organ transplants; hyperproliferative diseases including cancer and myeloproliferative diseases; viral diseases; metabolic diseases; and vascular diseases.

Compounds

The present invention relates to compounds of formula I.

In one embodiment, the compound of formula I has the formula Ia:

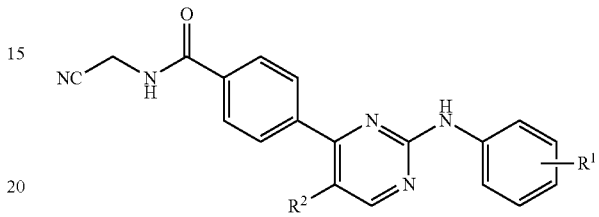

wherein, $R^1$ and $R^2$ are as defined above, or an enantiomer thereof, a prodrug thereof or a pharmaceutically acceptable salt thereof.

In another embodiment, the compound of formula Ia has the formula Ib:

Ib

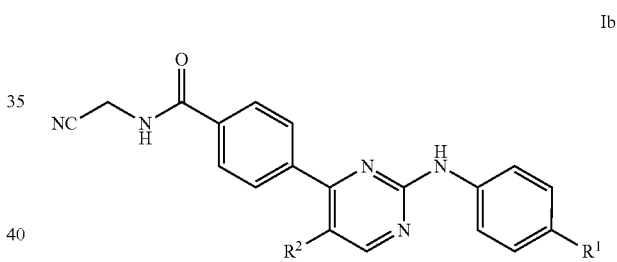

wherein, $R^1$ and $R^2$ are as defined above, or an enantiomer thereof, a prodrug thereof or a pharmaceutically acceptable salt thereof.

In one embodiment, $R^1$ is an 6 to 12 membered saturated fused or bridged bicyclic or spirocyclic heterocyclyl containing at least one heteroatom selected from N, O and/or S, preferably N in one ring and O in the other ring. Each ring of the bicyclic heterocyclyl may be 4-6 membered with the N-containing heterocyclyl including azetidine, pyrrolidine and piperidine and the O-containing heterocyclyl including oxetane, oxolane, (tetrahydrofuran) and dihydropyran or pyran. The N atom in the N-containing heterocyclyl is preferably attached to the phenyl ring of formula I or Ia. Examples of 6-12 membered N and O-containing saturated fused bicyclic heterocyclyls include 6-oxa-3-azabicyclo[3.2.0]heptane, hexahydro-2H-furo[2,3-c]pyrrole and 8-oxa-3-azabicyclo[4.2.0]octane. Examples of 6-12 membered N and O-containing saturated bridged bicyclic heterocyclyls include 6-oxa-3-aza-bicyclo[3.1.1]heptane, 8-oxa-3-azabicyclo[3.2.1]octane, 2-oxa-5-azabicyclo[2.2.1]heptane, 3-oxa-8-azabicyclo[3.2.1]octane and 3-oxa-6-azabicyclo[3.1.1]heptane. Examples of 6-12 membered N and O-containing saturated spirocyclic heterocyclyls include 1-oxa-6-azaspiro[3.3]heptane, 2-oxa-6-azaspiro[3.3]heptane, 1-oxa-6-ozaspiro[3.3]heptane, 1-oxa-6-azaspiro[3.4]octane, 1-oxa-6-azapiro[3.5]nonane and 1-oxa-7-azaspiro[3.5]nonane.

In one embodiment, $R^2$ is H, methyl Cl, Br or F, preferably H or methyl Examples of compounds of formula I or Ia include, but are not limited to, the following:

TABLE 1

| Compound Number | STRUCTURE | NAME |
|---|---|---|
| 1 | 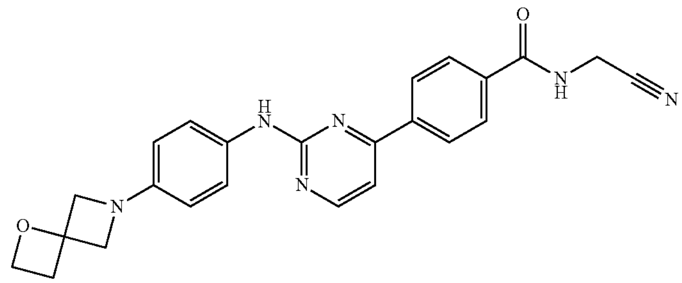 [SMILES: N#CCNC(=O)c1ccc(-c2ccnc(Nc3ccc(N4CC5(CCO5)C4)cc3)n2)cc1] | 4-(2-((4-(1-oxa-6-azaspiro[3.3]heptan-6-yl)phenyl)amino)pyrimidin-4-yl)-N-(cyanomethyl)benzamide |
| 2 | 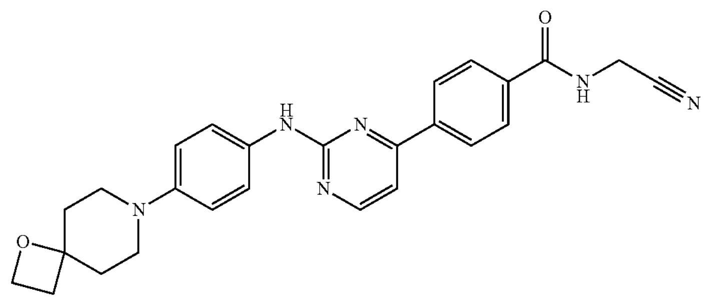 [SMILES: N#CCNC(=O)c1ccc(-c2ccnc(Nc3ccc(N4CCC5(CCO5)CC4)cc3)n2)cc1] | 4-(2-((4-(1-oxa-7-azaspiro[3.5]nonan-7-yl)phenyl)amino)pyrimidin-4-yl)-N-(cyanomethyl)benzamide |
| 3 | 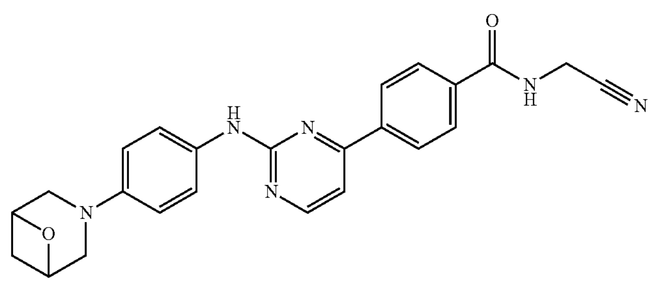 [SMILES: N#CCNC(=O)c1ccc(-c2ccnc(Nc3ccc(N4CC5CC(C4)O5)cc3)n2)cc1] | 4-(2-((4-(6-oxa-3-azabicyclo[3.1.1]heptan-3-yl)phenyl)amino)pyrimidin-4-yl)-N-(cyanomethyl)benzamide |
| 4 | 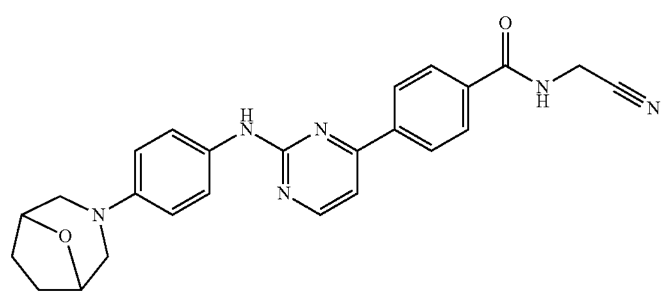 [SMILES: N#CCNC(=O)c1ccc(-c2ccnc(Nc3ccc(N4CC5CCC(C4)O5)cc3)n2)cc1] | 4-(2-((4-(8-oxa-3-azabicyclo[3.2.1]octan-3-yl)phenyl)amino)pyrimidin-4-yl)-N-(cyanomethyl)benzamide |
| 5 | 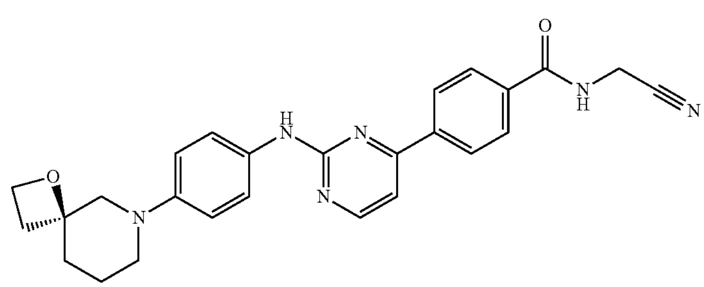 [SMILES: N#CCNC(=O)c1ccc(-c2ccnc(Nc3ccc(N4CCC[C@]5(CCO5)C4)cc3)n2)cc1] | (S)-4-(2-((4-(1-oxa-6-azaspiro[3.5]nonan-6-yl)phenyl)amino)pyrimidin-4-yl)-N-(cyanomethyl)benzamide |

TABLE 1-continued

| Compound Number | STRUCTURE | NAME |
|---|---|---|
| 6 | 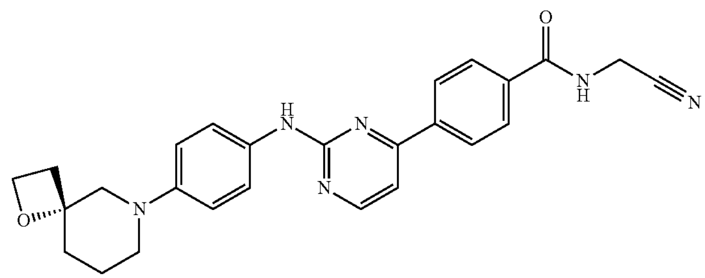 [SMILES: N#CCNC(=O)c1ccc(-c2ccnc(Nc3ccc(N4CCC[C@@]5(CCO5)C4)cc3)n2)cc1] | (R)-4-(2-((4-(1-oxa-6-azaspiro[3.5]nonan-6-yl)phenyl)amino)pyrimidin-4-yl)-N-(cyanomethyl)benzamide |
| 7 | 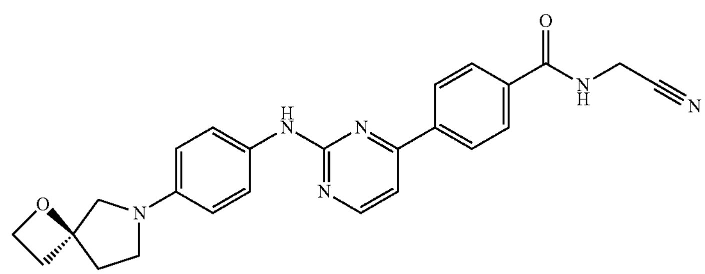 [SMILES: N#CCNC(=O)c1ccc(-c2ccnc(Nc3ccc(N4CC[C@]5(CCO5)C4)cc3)n2)cc1] | (S)-4-(2-((4-(1-oxa-6-azaspiro[3.4]octan-6-yl)phenyl)amino)pyrimidin-4-yl)-N-(cyanomethyl)benzamide |
| 8 | 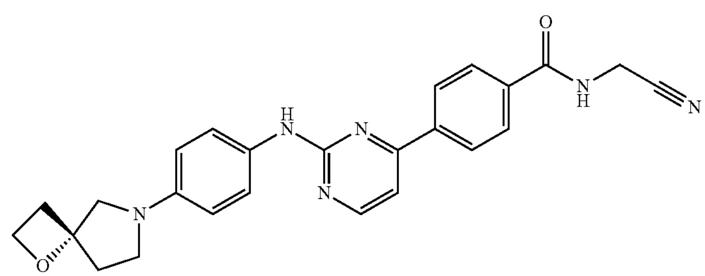 [SMILES: N#CCNC(=O)c1ccc(-c2ccnc(Nc3ccc(N4CC[C@@]5(CCO5)C4)cc3)n2)cc1] | (R)-4-(2-((4-(1-oxa-6-azaspiro[3.4]octan-6-yl)phenyl)amino)pyrimidin-4-yl)-N-(cyanomethyl)benzamide |
| 9 | 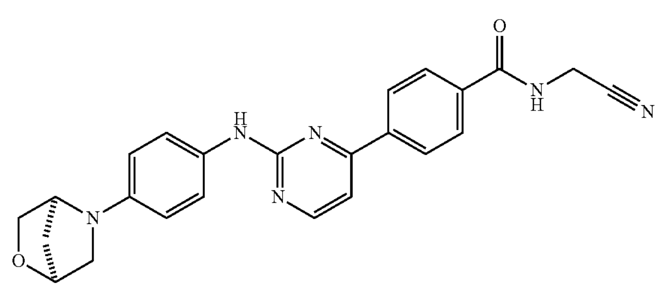 [SMILES: N#CCNC(=O)c1ccc(-c2ccnc(Nc3ccc(N4C[C@@H]5C[C@H]4CO5)cc3)n2)cc1] | 4-(2-((4-((1S,4S)-2-oxa-5-azabicyclo[2.2.1]heptan-5-yl)phenyl)amino)pyrimidin-4-yl)-N-(cyanomethyl)benzamide |
| 10 | 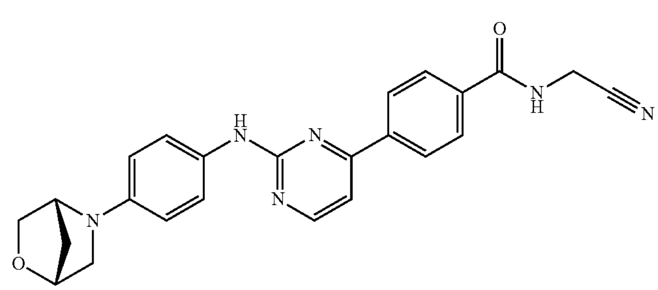 [SMILES: N#CCNC(=O)c1ccc(-c2ccnc(Nc3ccc(N4C[C@H]5C[C@@H]4CO5)cc3)n2)cc1] | 4-(2-((4-((1R,4R)-2-oxa-5-azabicyclo[2.2.1]heptan-5-yl)phenyl)amino)pyrimidin-4-yl)-N-(cyanomethyl)benzamide |

TABLE 1-continued

| Compound Number | STRUCTURE | NAME |
|---|---|---|
| 11 | 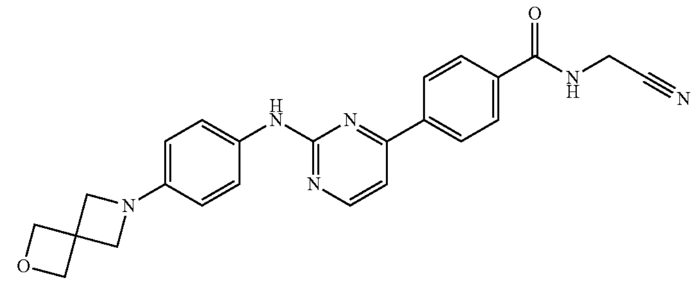 [SMILES: N#CCNC(=O)c1ccc(-c2ccnc(Nc3ccc(N4CC5(COC5)C4)cc3)n2)cc1] | 4-(2-((4-(2-oxa-6-azaspiro[3.3]heptan-6-yl)phenyl)amino)pyrimidin-4-yl)-N-(cyanomethyl)benzamide |

The term "$C_{1-4}$alkyl" refers to straight chain or branched chain hydrocarbon groups having from 1 to 4 carbon atoms. Examples include ethyl, propyl, isopropyl, butyl, isobutyl, sec-butyl and tert-butyl.

The term "$C_{1-4}$alkoxy" refers to straight chain or branched oxy-containing groups having alkyl portions of 1 to 4 carbon atoms. Examples include methoxy, ethoxy, propoxy, butoxy and tert-butoxy.

The term "bicyclic heterocyclyl" refers to compounds having two connected rings containing at least one heteroatom. The connection of the rings may occur across a bond between two adjacent atoms (fused bicylic heterocyclyl), across a sequence of atoms (bridged bicyclic heterocyclyl) or at a single atom (spirocyclic heterocyclyl).

The bicyclic heterocyclyl is a non-aromatic bicyclic ring which can be saturated or contains one or more units of unsaturation. The bicyclic ring may contain 6 to 12 ring atoms in which one or more ring carbons are replaced by a heteroatom such as N, S and/or O for example, N and/or O.

The C, N and S atoms may optionally be oxidised and the N atoms may optionally be quaternised.

Examples include bicyclo [4-6, 4-6] heterocyclyl systems such as bicyclo [4,4], [4,5], [5,4], [5,6], [6,4], [6,5] or [6,6] heterocyclyl systems.

Suitable 4-6 membered N-containing heterocyclyls include those containing one N atom such as azetidine (4-membered ring); pyrrolidine (tetrahydropyrrole), pyrroline (e.g., 3-pyrroline, 2,5-dihydropyrrole), 2H-pyrrole or 3H-pyrrole (isopyrrole, isoazole) (5-membered rings); and piperidine, dihydropyridine or tetrahydropyridine (6-membered rings); or those containing two N atoms such as imidazoline, pyrazolidine (diazolidine), imidazoline or pyrazoline (dihydropyrazole) (5-membered rings) and piperazine (6-membered ring).

Suitable 4-6 membered O-containing heterocyclyls include those containing one O atom such as oxetane (4-membered ring); oxolane (tetrahydrofuran) or oxole (dihydrofuran) (5-membered rings); and oxane (tetrahydropyran), dihydropyran or pyran (6-membered rings); those containing two O atoms such as dioxolane (5-membered ring) and dioxane (6 membered ring); or those containing three O atoms such as trioxane (6-membered ring).

Suitable 4-6 membered S-containing heterocyclyls include those containing one S atom such as thietane (4-membered ring); thiolane (tetrahydrothiophene) (5-membered ring); and thiane (tetrahydrothiopyran) (6-membered ring).

Suitable 4-6 membered N and O-containing heterocyclyls include those containing one N and one O atom such as tetrahydrooxazole, dihydrooxazole, tetrahydroisoxazole or dihydroisoxazole (5-membered rings); and morpholine, tetrahydrooxazine, dihydrooxazine or oxazine (6-membered rings); or those containing two N and one O atom such as oxadiazine (6-membered ring).

Suitable 4-6 membered N and S-containing heterocyclyls include thiazoline, thiazolidine (5-membered rings); and thiomorpholine (6-membered rings).

Suitable 4-6 membered O and S-containing heterocyclyls include oxathiole (5-membered ring); and oxathiane (thioxane) (6-membered ring).

Suitable 4-6 membered N, O and S-containing heterocyclyls include oxathiazine (6-membered ring).

In one embodiment, the bicyclic heterocyclyl contains N in one ring and O in the other ring.

The N-containing ring system may be 4-6 membered and is preferably saturated and attached directly to the phenyl ring suitably via the N atom. Examples of 4-6 membered saturated N-containing heterocyclyls include azetidine, pyrrolidine and piperidine.

The O-containing ring system may be 4-6 membered and is preferably saturated and attached to the N-containing ring across a bond between two carbon atoms to form a 6-12 membered saturated bicyclic N and O-containing fused bicyclic heterocyclyl; across a sequence of 3-4 or 3-5 carbon atoms (including the ring junction atoms) optionally replaced by one or more O atoms to form a 6-12 membered saturated N and O-containing bridged bicyclic heterocyclyl; or at a single carbon atom to form a 6-12 membered saturated N and O-containing spirocyclic heterocyclyl. Examples of 4-6 membered saturated O-containing heterocyclyls include oxetane, oxolane (tetrahydrofuran) and dihydropyran or pyran.

Suitable 6-12 membered saturated N and O-containing fused bicyclic heterocyclyls include those containing the 4-6 membered saturated N and O-containing heterocyclyls described above such as bicyclo [5,4] systems, for example 6-oxa-3-azabicyclo[3.2.0]heptane; bicyclo [5,5] systems, for example hexahydro-2H-furo[2,3-c]pyrrole; and bicyclo [6,4] systems, for example 8-oxa-3-azabicyclo[4.2.0]octane.

Suitable 6-12 membered saturated N and O-containing bridged bicyclic heterocyclyls include bicyclo [6,4] systems for example 6-oxa-3-azabicyclo[3.1.1]heptane; bicyclo [6,5] systems for example 8-oxa-3-azabicyclo[3.2.1]octane; bicyclo[5,5] systems for example 2-oxa-5-azabicyclo[2.2.1]heptane; and bicyclo [5,6] systems for example 3-oxa-8-azabicyclo[3.2.1]octane.

Suitable 6-12 membered saturated N and O-containing spirocyclic bicyclic heterocyclyls include bicyclo [4,4] systems for example 1-oxa-6-azaspiro[3.3]heptane, 2-oxa-6- azaspiro[3.3]heptane and 1-oxa-6-azaspiro[3.3]heptane; bicyclo [5,4] systems for example 1-oxa-6-azaspiro[3.4]octane; and bicyclo [6,4] systems for example 1-oxa-6-azaspiro[3.5]nonane and 1-oxa-7-azaspiro[3.5]nonane.

The term "halogen" refers to fluorine, chlorine, bromine and iodine.

The term "substituted" refers to a group that is substituted with one or more groups selected from $C_{1-6}$ alkyl, $C_{3-6}$ cycloalkyl, $C_{2-6}$ alkenyl, $C_{2-6}$ alkynyl, $C_{1-6}$ alkylaryl, aryl, heterocycylyl, halo, halo$C_{1-6}$alkyl, halo$C_{3-6}$cycloalkyl, halo$C_{2-6}$alkenyl, halo$C_{2-6}$alkynyl, haloaryl, haloheterocycylyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, oxo, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocycylylacyl, acylamino, acyloxy, aldehydro, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferred substituents are selected from the group consisting of $C_{1-4}$ alkyl, $C_{3-6}$ cycloalkyl, $C_{2-6}$ alkenyl, $C_{2-6}$ alkynyl, $C_{1-6}$ alkylaryl, aryl, heterocycylyl, halo, oxo, haloaryl, haloheterocycylyl, hydroxy, $C_{1-4}$ alkoxy, aryloxy, carboxy, amino, $C_{1-6}$alkylacyl, arylacyl, heterocyclylacyl, acylamino, acyloxy, $C_{1-6}$alkylsulphenyl, arylsulphonyl and cyano.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer, where the preferred isomer gives the desired level of potency and selectivity.

This invention also encompasses prodrugs of the compounds of formula I. The invention also encompasses methods of treating disorders that can be treated by the inhibition of protein kinases, such as JAK comprising administering drugs or prodrugs of compounds of the invention. For example, compounds of formula I having free amino, amido, hydroxy or carboxylic acid groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen and sulfur atoms in formula I.

Process

Compounds of the general formula I are prepared by coupling the compound of formula II or IV with the compound of formula III. When the compound of formula IV is used, then the compound of formula V is prepared which is then coupled with

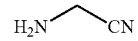

to prepare the compounds of formula I.

The compound of formula II or IV may generally be prepared by a cross-coupling reaction between a 2,4 dichloropyrimidine and a suitably functionalised coupling partner. Alternately the dichloropyrimidine may be converted to a diiodopyrimidine, which is then coupled with a suitably functionalised coupling partner. Typical coupling partners are organoboronic acids or esters (Suzuki coupling: see for example Miyaura, N. and Suzuki, *Chem. Rev.* 1995, 95 2457), organostannanes (Stille coupling: see for example Stille, J. K., *Angew. Chem., Int. Ed. Engl.,* 1986, 25, 508), Grignard reagents (Kumada coupling: Kumada, M.; Tamao, K.; Sumitani, K. *Org. Synth.* 1988, Coll. Vol. 6, 407.) or organozinc species (Negishi coupling: Negishi, E.; *J. Organomet. Chem.* 2002, 653, 34). The Suzuki coupling is the preferred coupling method and is typically performed in a solvent such as DME, THF, DMF, ethanol, propanol, toluene, acetonitrile or 1,4-dioxane, with or without added water, in the presence of a base such as sodium or potassium carbonate, lithium hydroxide, caesium carbonate, sodium hydroxide, potassium fluoride or potassium phosphate. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3/P(t-Bu)_3$.

The second step of the process involves a nucleophilic aromatic substitution reaction of the compound of formula II or IV with a suitably substituted aniline. The nucleophilic aromatic substitution is typically carried out by addition of the aniline to monohalo heterocyclic intermediate obtained from the first reaction in a solvent such as ethanol, n-propanol, isopropanol, tert-butanol, dioxane, THF, DMF, toluene or xylene. The reaction is typically performed at elevated temperature in the presence of an acid such as HCl or p-toluenesulfonic acid or in the presence of base such as a non-nucleophilic base such as triethylamine or diisopropylethylamine, or an inorganic base such as potassium carbonate or sodium carbonate.

Alternatively, the aniline substituent may be introduced through a transition metal catalysed amination reaction. Typical catalysts for such transformations include Pd(OAc)$_2$/P(t-Bu)$_3$, Pd$_2$(dba)$_3$/BINAP and Pd(OAc)$_2$/BINAP. These reactions are typically carried out in solvents such as toluene or dioxane, in the presence of bases such as caesium carbonate or sodium or potassium tert-butoxide at temperatures ranging from room temperature to reflux (e.g. Hartwig, J. F., *Angew. Chem. Int. Ed.* 1998, 37, 2046).

The anilines employed in the first step of the synthesis of these compounds may be synthesised through addition of the cicyclic amino to 1-fluoro-4-nitro-aniline and subsequent reduction of the nitro group using methods well known to those skilled in the art.

The products formed from either reaction step may be further derivatised using techniques known to those skilled in the art. Alternatively, derivatisation of the mono-halo intermediate may be undertaken prior to displacement of the halo substituent. Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, T., Wuts, P. (1999) *Protective Groups in Organic Synthesis*. Wiley-Interscience; 3rd edition.).

The leaving group in the compound of formula II or IV which is an intermediate used in the process of the present invention may be any suitable known type such as those disclosed in J. March, "Advanced Organic Chemistry: Reactions, Mechanisms and Structure" 4$^{th}$ Edition, pp 352-357, John Wiley & Sons, New York, 1992 which is incorporated herein by reference. Preferably, the leaving group is halogen, more preferably chlorine or iodine.

JAK Inhibition

The compounds of formula I have activity against protein kinases, particularly the JAK kinases and most particularly are active against JAK1, JAK2, JAK3 and TYK2. A JAK2 inhibitor is any compound that selectively inhibits the activity of JAK2. One activity of JAK2 is to phosphorylate a STAT protein. Therefore an example of an effect of a JAK2 inhibitor is to decrease the phosphorylation of one or more STAT proteins. The inhibitor may inhibit the phosphorylated form of JAK2 or the non-phosphorylated form of JAK2.

The present invention also provides the use of the compound of formula I as kinase inhibitors such as JAK kinase inhibitors, in particular JAK1, JAK2, JAK3 and TYK2 inhibitors.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly I the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorhexidine and thickening agents such as hypromellose may also be included.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents. Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) rectally or intravaginally, e.g. as a pessary, cream or foam.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: endothelin receptor antagonists (eg ambrisentan, bosentan, sitaxsentan), PDE-V inhibitors (eg sildenafil, tadalafil, vardenafil), Calcium channel blockers (eg amlodipine, felodipine, varepamil, diltiazem, menthol), prostacyclin, treprostinil, iloprost, beraprost, nitric oxide, oxygen, heparin, warfarin, diuretics, digoxin, cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABA's such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

Methods of Treatment

The compounds of formula I may be used in the treatment of kinase associated diseases including JAK kinase associated diseases such as immunological and inflammatory diseases including organ transplants; hyperproliferative diseases including cancer and myeloproliferative diseases; viral diseases; metabolic diseases; and vascular diseases.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The term "kinase associated diseases" refers to a disorder or disorders that directly or indirectly result from or are aggravated by aberrant kinase activity, in particular JAK activity and/or which are alleviated by inhibition of one or more of these kinase enzymes.

In a preferred embodiment the kinase associated disease state involves one or more of the JAK kinases, JAK1, JAK2, JAK3 or TYK2. In a particularly preferred embodiment, the disease involves JAK2 kinase. Such diseases include, but are not limited to, those listed in the Table below.

| Activation of the JAK/STAT pathway in various pathologies | | | | |
|---|---|---|---|---|
| Disease Type | Cell Types Involved | Cytokines involved | JAK Kinase Involved | Characteristics |
| Atopy | | | | |
| Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |
| CMI | | | | |
| Allergic Contact Dermatitis, hypersensitivity pneumonitis | T-cells, B-cells, macrophages, neutrophils | IL-2, IL-4, IL-5, IL-6, IL-10, IFNγ, TNF, IL-7, IL-13, | JAK1, JAK2, JAK3, Tyk2 | B cell and/or $T_{DH}$ cell activation Macrophage/granulocyte activation |
| AutoImmune and Inflammatory Diseases | | | | |
| Multiple sclerosis, Glomerulonephritis Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis Transplantation | B-Cells, T cells, monocytes, Macrophages, Neutrophils, Mast Cells, Eosinophils, | IL-2, IL-4, IL-5, IL-6, IL-7, IL-10, IL-13, IFNγ, TNF, GM-CSF; G-CSF, | JAK1, JAK2, JAK3, Tyk2 | Cytokine Production (e.g. TNFα/β, IL-1, CSF-1, GM-CSF), T-cell Activation, B cell activation, JAK/STAT activation |
| Allograft Rejection GvHD | T cells, B cells, macrophages | IL-2, IL-4, IL-5, IL-7, IL-13, TNF | JAK1, JAK2, JAK3, | Macrophage/T cell mediated necrosis, Tc cell mediated apoptosis, and B cell/Ig mediated opsonization/necrosis of foreign graft |
| Viral Diseases | | | | |
| Epstein Barr Virus (EBV) | Lymphocytes | Viral Cytokines, IL-2, | JAK1, JAK2, JAK3 | JAK/STAT Mediation |
| Hepatitis B | Hepatocytes | | | |
| Hepatitis C | Hepatocytes | | | |
| HIV | Lymphocytes | | | |
| HTLV 1 | Lymphocytes | | | |
| Varicella-Zoster Virus (VZV) | Fibroblasts | | | |
| Human Papilloma Virus (HPV) | Epithelial cells | | | |

| Disease Type | Cell Types Involved | Cytokines involved | JAK Kinase Involved | Characteristics |
|---|---|---|---|---|
| *Activation of the JAK/STAT pathway in various pathologies* | | | | |
| Hyperproliferative diseases-cancer | | | | |
| Leukemia | Leucocytes | Various Autocrine cytokines, Intrinsic Activation | JAK1, JAK2, JAK3 | Cytokine production, JAK/STAT Activation |
| Lymphoma | Lymphocytes | | | |
| Multiple Myeloma | various | | | |
| prostate cancer | various | | | |
| breast cancer | various | | | |
| hodgkins lympohoma | various | | | |
| B-cell chronic lymphocytic leukemia | various | | | |
| lung cancer | various | | | |
| hepatoma | various | | | |
| metastatic melanoma | various | | | |
| glioma | various | | | |
| Myeloproliferative Diseases | | | | |
| Polycythemia vera (PV), primary myelofibrosis, thrombocythemia, essential thrombocythemia (ET), idiopathic myelofibrosis, chronic myelogenous leukemia, systemic mastocystosis (SM), chronic neutrophilic leukemia (CNL), myelodisplastic syndrome (MDS), systemic mast cell disease (SMCD) | Hematopoietic | Interleukin-3, erythropoietin, thrombopoietin | JAK2 mutation | JAK/STAT activation |
| Vascular Disease | | | | |
| Hypertension, Hypertrophy, Heart Failure, Ischemia, Pulmonary arterial hypertension | Endothelial cells, smooth muscle cells including pulmonary artery smooth muscle cells, cardiac myocytes, fibroblasts, endothelial cells | IL6, angiotensin II, LIF, TNFalpha, serotonin, caveolin1 | JAK1, JAK2, TYK2 | JAK/STAT activation |
| Metabolic disease | | | | |
| Obesity, metabolic syndrome | Adipocytes, pituitary cells, neurons, monocytes | Leptin | JAK2 | JAK/STAT activation |

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease (COPD), pulmonary fibrosis, cystic fibrosis, inflammatory bowl disease, irritable bowl syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Motor Neurone Disease (Lou Gehrig's disease), Paget's disease, sepsis, conjunctivitis, nasal catarrh, chronic arthrorheumatism, systemic inflammatory response syndrome (SIRS), polymyositis, dermatomyositis (DM), Polaritis nodoa (PN), polymyalgia rheumatica, mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfrorna (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma]), fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphoma; Skin: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myeloproliferative diseases such as polycythemia vera (PV), primary myelofibrosis, thrombocythemia, essential thrombocythemia (ET), agnoneic myeloid metaplasia (AMM), also referred to as idiopathic myelofibrosis (IMF), chronic myelogenous leukemia (CML), systemic mastocystosis (SM), chronic neutrophilic leukemia (CNL), chronic myelomonocytic leukemia (CMML), myelodisplastic syndrome (MDS) and systemic mast cell disease (SMCD).

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

Preferred diseases for JAK2 inhibitors include immunological and inflammatory diseases such as auto-immune diseases for example atopic dermatitis, asthma, rheumatoid arthritis, Crohn's disease, psoriasis, Crouzon syndrome, achondroplasia, systemic lupus erythematosus, scleroderma, mixed connective tissue disease, vasculitis, thanatophoric dysplasia and diabetes; hyperproliferative disorders such as cancer for example prostate cancer, colon cancer, breast cancer, liver cancer such as hepatoma, lung cancer, head and neck cancer such as glioma, skin cancer such as metastatic melanoma, leukemia, lymphoma, multiple myeloma and myeloproliferative diseases such as polycythemia vera (PV), myelofibrosis, thrombocythemia, essential thrombocythemia (ET), agnogenic myeloid metaplasia (AMM), also referred to as idiopathic myelofibrosis (IMF) and chronic myelogenous leukemia (CML); and vascular diseases such as hypertension, hypertrophy, stroke, Raynaud's phenomenon, POEMS syndrome, angina, ischemia, migraine, peripheral arterial disease, heart failure, restenosis, atherosclerosis and pulmonary arterial hypertension.

Preferred diseases for JAK1 and TYK2 inhibitors include immunological and inflammatory diseases such as autoimmune diseases for example rheumatical arthritis, multiple sclerosis, psorlasis, Crohn's disease and inflammatory bowel disease. JAK1 inhibitors can also be used to treat hyperproliferative disorders such as cancer for example prostate cancer, colon cancer, breast cancer, liver cancer such as hepatoma, lung cancer, head and neck cancer such as glioma, skin cancer such as metastatic melanoma, leukemia, lymphoma, multiple myeloma and myeloproliferative diseases such as polycythemia vera (PV), myelofibrosis, thrombocythemia, essential thrombocythemia (ET), agnoneic myeloid metaplasia (AMM), also referred to as idiopathic myelofibrosis (IMF) and chronic myelogenous leukemia (CML).

Preferred diseases for JAK3 inhibitors are immunological and inflammatory diseases including autoimmune diseases such as systemic lupus erythematosus, mixed connective tissue disease, scleroderma, multiple sclerosis, autoimmune neuritis, rheumatoid arthritis, psoriasis, insulin resistance, Type I diabetes and complications from diabetes, metabolic syndrome, asthma, atopic dermatitis, autoimmune throid disorders, ulcerative colitis, Crohn's disease, Alzheimer's disease, and other indications where immunosuppression may be desirable such as organ transplants and graft vs host disease. Furthermore specific inhibitors of JAK3 may find application for therapeutic treatments for hyperproliferative diseases such as leukaemia and lymphoma where JAK3 is hyperactivated.

Dosages

The term "therapeutically effective amount" refers to the amount of the compound of formula I and II that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In embodiments, a compound of the present invention is administered for the treatment of "myeloproliferative disease" and "myeloproliferative neoplasms (MPN)" most notably polycythemia vera (PV), essential thrombocythemia (ET) and primary myelofibrosis (PMF). An international working group for myeloproliferative neoplasms research and treatment (IWG-MRT) has been established to delineate and define these conditions (see for instance Vannucchi et al, CA Cancer J. Clin., 2009, 59:171-191), and those disease definitions are to be applied for purposes of this specification. Subjects "at risk for" a particular form of MPN are subjects having an early stage form of the disease, and may for instance include subjects having a genetic marker thereof, such as the JAK2V617F allele which is associated with PV (>95%), with ET (60%) and with PMF (60%). Subjects are also considered to be "at risk for" a form of MFN if they already manifest symptoms of an earlier stage form. Thus, subjects presenting with MFN are at risk for post-PV and post-ET, both of which develop following MPN. For the treatment of such subjects, a compound of the present invention can be administered in tablet form in a unit dose within the range from 50 mg to 500 mg, including particularly 150 mg or 300 mg, and at a dosing frequency of from 1 to 4 times daily, such as once or twice daily. Such subjects can also be treated in combination with other drugs useful in the treatment of the particular condition, including such drugs as thalidomide, lenalidomide, other JAK2 or JAK1/2 kinase inhibitors, hydroxyurea or anagrelide, or in combination with bisphosphonates to decrease bone marrow fibrosis. As well, such patients can also undergo radiation therapy or allogeneic bone marrow transplantation, as part of the overall therapy that includes dosing with a present compound.

In another embodiment, a compound of the present invention is administered for the treatment specifically of myelodysplastic syndrome (MDS). Myelodysplastic syndrome (MDS) is a term used to describe a group of diseases characterized by ineffective hematopoiesis leading to blood cytopenias and hypercellular bone marrow. MDS has traditionally been considered to be synonymous with 'preleukemia' because of the increased risk of transformation into acute myelogenous leukemia (AML). Evolution to AML and the clinical consequences of cytopenias are main causes of morbidity and mortality in MDS. Debilitating symptoms of MDS include fatigue, pallor, infection, and bleeding. Anemia, neutropenia, and thrombocytopenia are also common clinical manifestations of MDS. For the treatment of such subjects, a compound of the present invention can be administered in tablet form in a unit dose within the range from 50 mg to 500 mg, including particularly 150 mg or 300 mg, and at a dosing frequency of from 1 to 4 times daily, such as once or twice daily.

In other embodiments, a compound of the present invention is administered for the treatment of anemia, including anemia associated with myeloproliferative disease, to achieve an effective anemia response. By "anemia response" is meant an increase in the patient's hemoglobin level or a patient who was transfusion dependent becoming transfusion independent. Desirably, a minimum increase in hemoglobin of 2.0 g/dL lasting a minimum of 8 weeks is achieved, which is the level of improvement specified in the International Working Group (IWG) consensus criteria. However, smaller, but still medically significant, increases in hemoglobin are also considered to be within the scope of the present invention. Anemic subjects that would benefit from treatment with a present compound include subjects that have undergone or are undergoing chemotherapy or radiation therapy, such as cancer patients. A wide variety of chemotherapeutic agents are known to have the consequence of reducing the level of functioning red blood cells. As well, subjects that are treatment candidates are those afflicted with blood disorders including blood cancers that result in, or are associated with, a reduction in red blood cell count. In embodiments, the subjects to be treated are subjects having anemia associated with or resulting from such blood conditions as myelodysplastic syndrome. In other embodiments, the subjects to be treated are subjects having anemia associated with or resulting from such other blood conditions as anemias associated with other hematologic malignancies, aplastic anemia, anemia of chronic disease that affect red blood cells and the like. Anemia of chronic disease is associated with such diseases as certain cancers including lymphomas and Hodgkin's disease; autoimmune diseases such as rheumatoid arthritis, systemic lupus erythematosis, inflammatory bowel disease and polymyalgia rheumatica; long term infections such as urinary tract infection, HIV and osteomyelitis; heart failure; and chronic kidney disease. In addition, patients with anemia resulting from conditions associated with increased destruction, shortened red blood cell survival and splenic sequestration could also benefit from treatment with a present compound. In certain embodiments, the subject to be treated is an anemic subject experiencing thalassemia. In other embodiments, the subject to be treated is a subject other than a subject experiencing thalassemia. Patients afflicted with these conditions thus can be treated to improve upon their state of declining or deficient hemoglobin. For the treatment of such subjects, a compound of the present invention can be administered in tablet form in a unit dose within the range from 50 mg to 500 mg, including particularly 150 mg or 300 mg, and at a dosing frequency of from 1 to 4 times daily, such as once or twice daily. For treatment of anemic subjects, a present compound may be administered in combination with an anemia treatment drug, compound or modality selected from blood transfusion, iron supplements, erythropoietin or darbapoietin therapy, and the like.

In another embodiment, a compound of the present invention is administered for the treatment of multiple myeloma (MM), including particularly MM cells that have a CD45 negative (CD45−) phenotype, and/or MM cells that are considered IL-6 non-responsive. MM cells are the disease cells that form plasmacytoma tumours that are the hallmark of multiple myeloma. "CD45− phenotype" refers to a MM cell that tests negative or dim, as distinct from intermediate to bright, for surface expression of the protein marker known as CD45, which is a well-known marker of all hematopoietic cells. The CD45− phenotype is also ascribed herein with reference to a population of MM cells in which the prevalence of CD45− cells within that population exceeds at least about 10% of that population, such as at least about 15%, or 20%, or 25%, or 30%, or 35%, or 40%, or 45% or at least about 50% of that population. Detection of CD45 on the cellular surface is readily achieved using fluorescence-labeled CD45 monoclonal antibody and established techniques of fluorescence-activation cell sorting (FACS) or any related means for identifying cells that bind the CD45 antibody. Reference can be made for instance to the articles published by Moreau et al, Haematologica, 2004, 89(5):547, and by Kumar et al, Leukemia, 2005, 19:1466, the disclosures of which are incorporated herein by reference.

MM cells that are "IL-6 non-responsive" are identified as cells that do not rely for survival on the presence of interleukin-6 (IL-6). Thus, a MM cell that is IL-6 non-responsive shows insubstantial response, in terms such as IL-6 receptor stimulation or downstream signalling events, when incubated with an otherwise stimulatory amount of IL-6. Such MM cells can particularly include those MM cells that are resident in the bone marrow environment, and which thus grow in the same environment as bone marrow stromal cells, but they also include MM cells in circulation that are not exposed to the marrow environment.

Within the realm of MM and its progression and development, CD45 represents an early marker of the disease MM cells. As the disease progresses, a shift occurs in CD45 phenotype of those cells, in which the predominance of CD45+ cells wanes, and the population of disease plasma cells becomes predominantly CD45− (see Kumar et al, Leukemia, 2005, 19(8):1466). A shift also occurs in the number of IL-6 non-responsive cells, with this cell form becoming predominant in the later stages of disease. In the present method, the use of the present compounds is proposed for the treatment of MM cells, and plasmacytoma tumours that arise therefrom, that have acquired the CD45− and/or IL-6 non-responsive phenotype. For the treatment of such subjects, a compound of the present invention can be administered in tablet form in a unit dose within the range from 50 mg to 500 mg, including particularly 150 mg or 300 mg, and at a dosing frequency of from 1 to 4 times daily, such as once or twice daily. For treatment of MM subjects, a present compound may be administered in combination with another MM treatment drug, compound or modality such as melphalan and bortezomib, and the like.

In order to exemplify the nature of the present invention such that it may be more clearly understood, the following non-limiting examples are provided.

EXAMPLES

Compound Synthesis

The compounds of the invention may be prepared by methods well known to those skilled in the art, and as described in the synthetic and experimental procedures shown below for selected compounds.

DEFINITIONS

DMAP 4-dimethylaminopyridine
DLM dichloromethane
TEA triethylamine
DIPEA or DIEA diisopropylethylamine
DMSO dimethylsulfoxide
THF tetrahydrofuran
KHMDS potassium hexamethyl disilazide
TBAF tetrabutyl ammonium fluoride
TBSCL terbutyl dimethylsilyl chloride
TMSOI trimethylsulfoxonium iodide Example 1

Synthesis of Compound 1

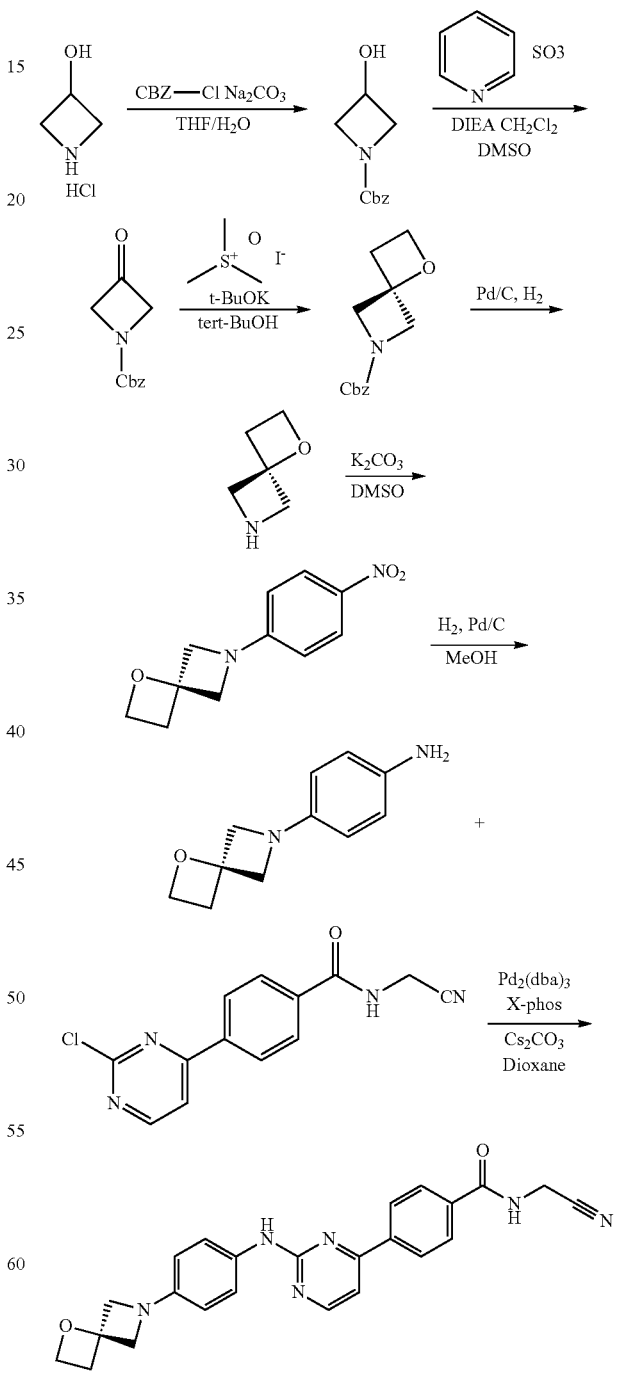

Compound 1

Synthesis of 1-1

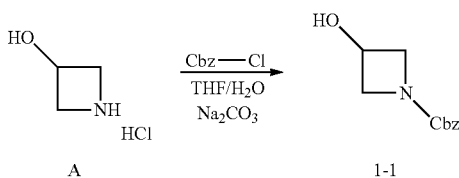

To a stirred solution of intermediate A (10.00 g, 91 mmol,) in H$_2$O and THF (200 mL) was added Na$_2$CO$_3$ (19.5 g 0.18 mol), followed by Cbz-Cl (18.40 g, 0.11 mol.). The resulting mixture was stirred at rt for 1 h. The reaction mixture was quenched by addition of 1M aq HCl. The aqueous layer was extracted twice with CH$_2$Cl$_2$ and the combined organic layers were washed with brine and dried (Na$_2$SO$_4$), filtered and concentrated. The crude product was purified by column chromatography (EtOAc/Pet ether 1:4) to obtain compound 1-1 (13.60 g, 72%) as a white solid. The structure was confirmed by LC-MS spectra. TLC: Rf=0.3 (silica gel, EA:PE=1:2, v/v) LC-MS: [M+1]$^+$=208; [M+Na]=230.

Synthesis of 1-2

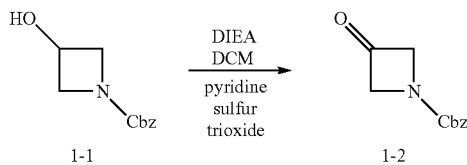 [SMILES: O=C(OCc1ccccc1)N1CC(O)C1 ; "DIEADCM" ; O=C1CN(C(=O)OCc2ccccc2)C1 ; "1-1" ; "1-2"]

To a stirred solution of intermediate 1-1 (13.60 g, 66 mmol) in DCM (100 mL) at 0° C. was added DIPEA (57.5 mL 0.33 mol) dropwise, followed by pyridine sulfur trioxide (24.20 g, 0.15 mol) in DMSO (70 mL). The resulting mixture was stirred at 0° C. for 1 h. The mixture was then poured into ice-water and the aqueous layer extracted twice with DCM. The combined organic layers were washed with brine and dried (Na$_2$SO$_4$), filtered and concentrated. The crude product was purified by column chromatography (EtOAc/Pet.ether 1:2) to obtain compound 1-2 (6.50 g 48%) as yellow solid. The structure was confirmed by H-NMR spectra. TLC: Rf=0.7 (silica gel, EA:PE=1:1, v/v). $^1$H-NMR (400 MHz, CDCl$_3$) δ (ppm): 7.38 (m, 5H), 5.17 (s, 2H), 4.76 (s, 4H).

Synthesis of 1-3

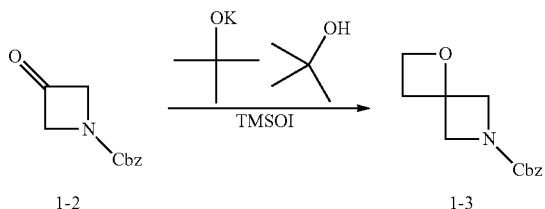

To a stirred solution of trimethylsulfoxonium iodide (4.20 g, 20.5 mmol) in t-BuOH (100 mL) was added KOtBu (11.00 g 50.0 mmol) and the reaction heated at 50° C. for 1 h. 1-2 (4.80 g, 42.8 mmol) was added and the resulting mixture was stirred at 50° C. for a further 48 h, then quenched by addition of saturated NH$_4$Cl and EA. The aqueous layer was extracted twice with EA and the combined organic layers were then washed with brine, dried (Na$_2$SO$_4$) and concentrated. The crude product was purified by flash chromatography (EA/PE, 1:2) to obtain compound D (530 mg, 11%) as yellow oil.
TLC: Rf=0.36 (silica gel, EA:PE=1:2, v/v)
LC-MS: [M+1]$^+$=234; [M+Na]=256
$^1$H-NMR (400 MHz, CDCl$_3$) δ (ppm): 7.36-7.32 (m, 5H), 5.08 (s, 2H), 4.51 (t, J=7.5 Hz, 2H), 4.23-4.14 (m, 4H), 2.83 (t, J=7.5 Hz, 2H).

Synthesis of 1-4

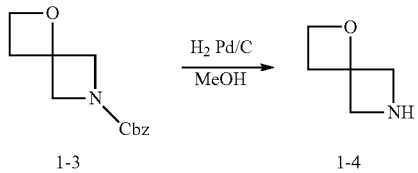

To a stirred solution of intermediate 1-3 (860 mg, 3.7 mmol) in MeOH (40 mL) was added 10% Pd/C (100 mg) and the reaction stirred under H$_2$ (50 psi) at 60° C. for 3 days. The reaction was filtered through a pad of Ceilte and washed with MeOH. The filtrate was concentrated under reduced pressure to obtain compound 1-4 (360 mg, 98%) as an oil. It was used for the next step without further purification. The structure was confirmed by LC-MS spectra.
TLC: Rf=0.04 (silica gel, EA:PE=1:2, v/v)
LC-MS: [M+1]$^+$=100

Synthesis of 1-5

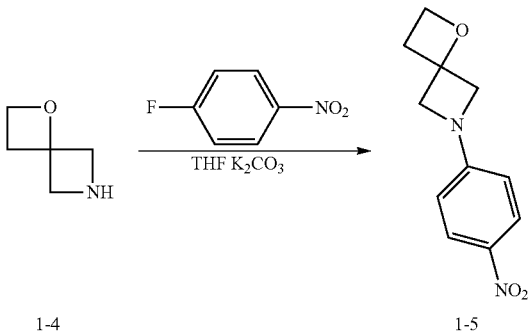

To a stirred solution of intermediate 1-4 (430 mg, 4.34 mmol) in THF (50 mL) was added K$_2$CO$_3$ (720 mg 5.21 mmol), followed by 1-fluoro-4-nitrobenzene (612 mg, 34.34 mmol). The resulting mixture was stirred at 80° C. for 5 h. The reaction was cooled to room temperature and poured into water. The aqueous layer was extracted twice with EtOAc and the combined organic layers were washed with brine, dried (Na$_2$SO$_4$), filtered and concentrated. The crude product was purified by flash chromatography (EtOAc/Pet.ether=1:2) to give 1-5 (226 mg 28%) as yellow solid. The structure was confirmed by LC-MS spectra.
TLC: Rf=0.4 (silica gel, EA:PE=1:2, v/v)
LC-MS: [M+H]$^+$=221, [M+Na]=243

Synthesis of 1-6

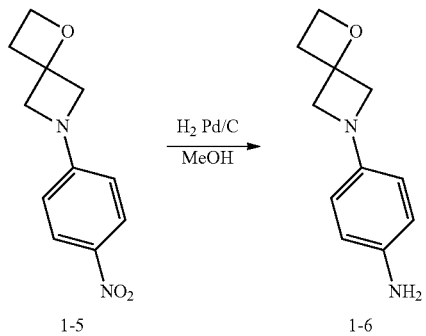

To a stirred solution of intermediate F (226 mg, 1.0 mmol., 1.0 eq) in MeOH (20 mL) was added 10% Pd/C (20 mg) and the reaction stirred under 1 atm $H_2$ at 50° C. for 3 days. The reaction mixture was filtered through a pad of Ceilte and washed with MeOH. The filtrate evaporated under reduced pressure to give 1-6 (192 mg, 98%) as red solid. The structure was confirmed by LC-MS spectra and used for the next step without further purification.

TLC: Rf=0.25 (silica gel, EA:PE=1:1, v/v)

LC-MS: $[M+1]^+$=191

Synthesis of Compound 1

To a stirred solution of intermediate 1-6 (192 mg, 1.0 mmol) in dioxane (40 mL) was added $Cs_2CO_3$ (658 mg 2.0 mmol) and X-phos (48 mg 0.1 mmol), followed by $Pd_2(dba)_3$ (92 mg 0.1 mmol). The resulting mixture was heated at 100° C. for 6 h under $N_2$. The reaction mixture was cooled to room temperature and filtered through a pad of Ceilte and washed with EtOAc. The filtrate was poured into water and the aqueous layer extracted twice with EtOAc. The combined organic layers were then washed with brine, dried ($Na_2SO_4$), filtered and evaporated. The crude product was purified by flash chromatography (MeOH/DCM=1:50) to give analogue 1 (41 mg 10%) as yellow solid. The structure was confirmed by LC-MS and $^1$H-NMR spectra.

TLC: Rf=0.4 (silica gel, MeOH/DCM=1:20, v/v)

LC-MS: $[M+1]^+$=427

$^1$H-NMR (400 MHz, MeOD) δ (ppm): 8.42 (d, J=5.2 Hz, 1H), 8.25 (d, J=8.5 Hz, 2H), 7.98 (d, J=8.5 Hz, 2H), 7.52 (d, J=8.8 Hz, 2H), 7.28 (d, J=5.2 Hz, 1H), 6.55 (t, J=5.9 Hz, 2H), 4.59 (t, J=7.6 Hz, 2H), 4.36 (s, 2H), 4.12 (d, J=9.5 Hz, 2H), 3.90 (d, J=9.6 Hz, 2H), 2.96 (t, J=7.6 Hz, 2H).

Example 2

Synthesis of Compound 2

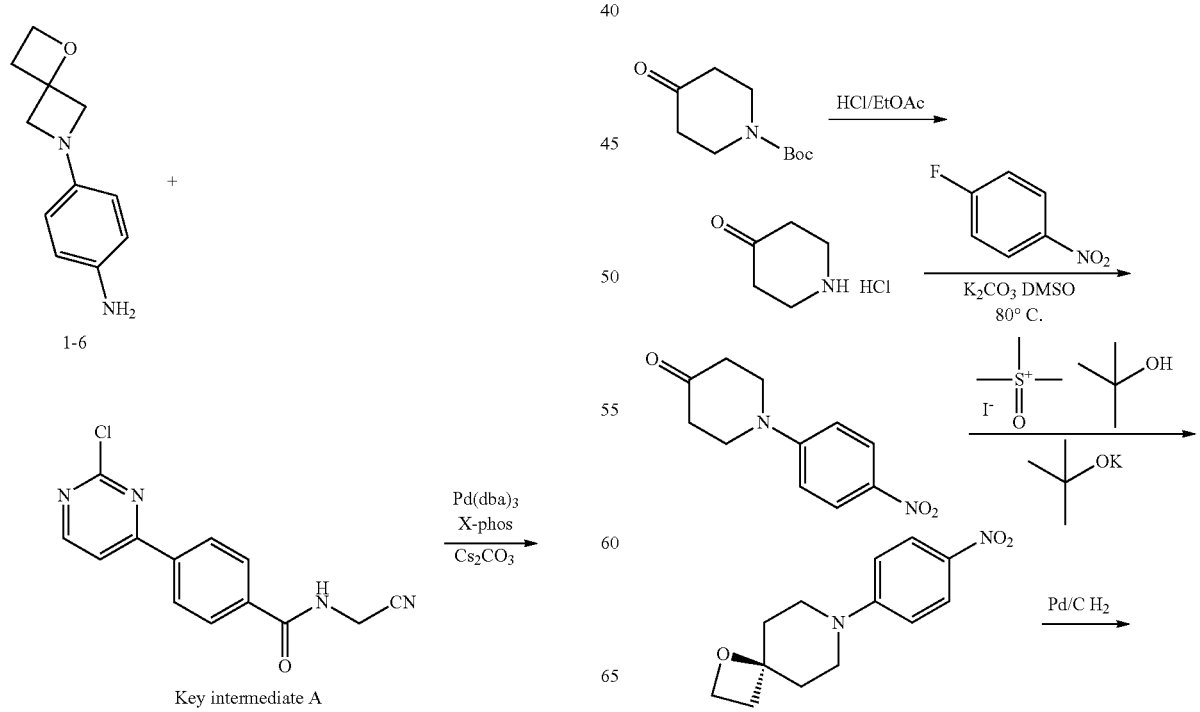

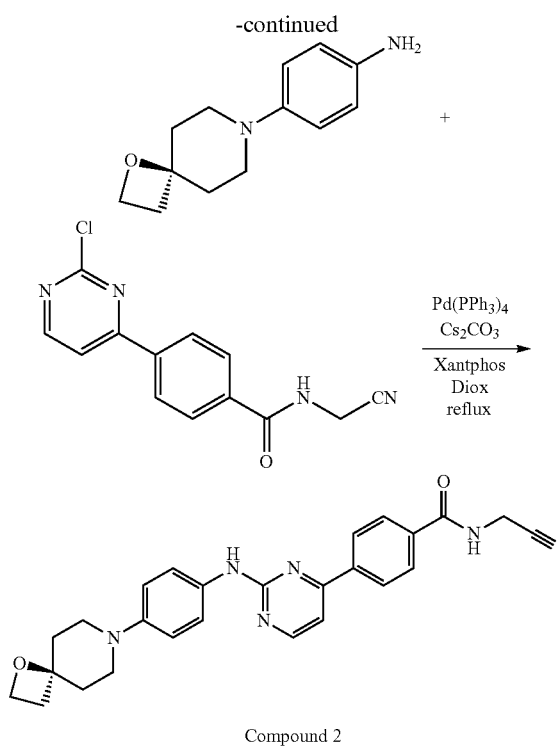

Compound 2

Synthesis of 2-2 and 2-3

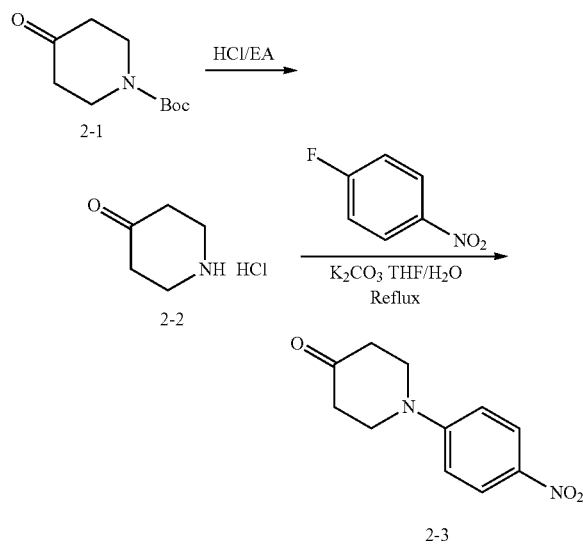

To a solution of 2-1 (5.00 g, 25.1 mmol) in EtOAc (10 mL) was added 4 M HCl-EtOAc (20 mL) and the mixture was stirred at room temperate for 2 h. The solid precipitate was collected by filtration and washed with EtOAc. The filter cake was dried under reduced pressure to give a white solid (3.40 g, 100%). It was used for the next step without further purification.

To a solution of 2-2 (3.40 g, 25 mmol) in THF/H$_2$O (50 mL/50 mL) was added 1-fluoro-4-nitrobenzene (3.54 g, 25 mmol) and K$_2$CO$_3$ (7.60 g, 55 mmol) and the mixture heated to reflux overnight. The mixture was allowed to cool to room temperature and extracted with EtOAc (200 mL×3). The organic layers were combined and washed with brine (150 mL), dried (MgSO$_4$), filtered and concentrated. The crude residue obtained was washed with EtOAc (10 mL) to give a yellow solid (4.6 g, 83%). The structure was confirmed by LC-MS spectra. It was used for the next step without further purification.

TLC: Rf=0.20 (silica gel, EtOAc/Pet ether=1/1, v/v)

LC-MS: [M+1]$^+$=221

Synthesis of 2-4

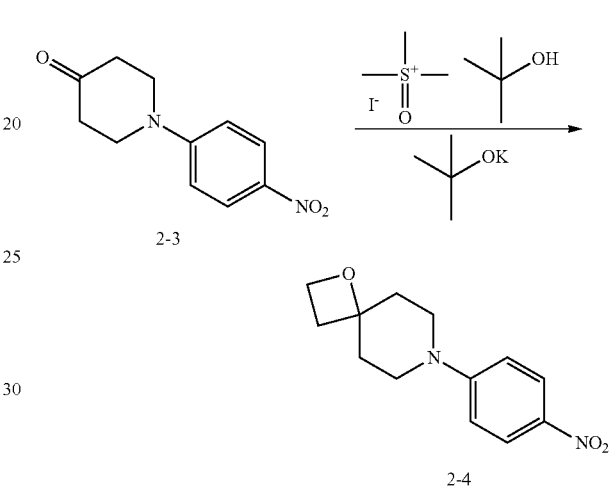

To a solution of trimethylsulfoxonium iodide (11.50 g, 52 mmol) in t-BuOH (100 mL) was added t-BuOK (5.00 g, 52 mmol) and the reaction stirred at 50° C. for 1.5 h. 2-3 (4.60 g, 21 mmol) was added and the reaction mixture was stirred at 50° C. for a further 48 h. The mixture was poured into H$_2$O (300 mL) and extracted with EtOAc (200 mL×3). The organic layers were combined and washed with brine (200 mL), dried (MgSO4), filtered and concentrated. The residue obtained was washed with EtOAc (20 mL) and the yellow solid obtained dried under reduced pressure to afford the product (2.30 g, 44%). The structure was confirmed by LC-MS spectra. It was used for the next step without further purification.

TLC: Rf=0.20 (silica gel, EtOAc/Pet ether=1/1, v/v)

LC-MS: [M+1]$^+$=249

Synthesis of 2-5

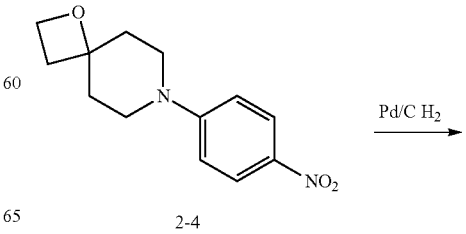

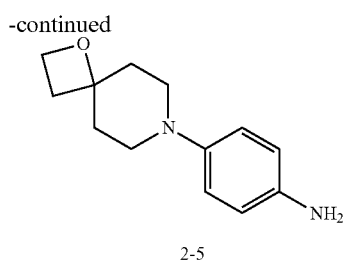

2-5

To a solution of 2-4 (2.30 g, 9.3 mmol) in CH₃OH (30 ml) was added 10% Pd/C (230 mg) and the reaction stirred under a hydrogen atmosphere overnight. The catalyst was removed by filtration through a pad of Celite and washed with MeOH. The filtrate was concentrated and the residue purified by silica gel column chromatography with (CH₂Cl₂/CH₃OH=80/1-20/1) to give 2-5 (320 mg, 16%) as red solid. The structure was confirmed by LC-MS and H-NMR spectra.
TLC: Rf=0.3 (silica gel, EA:PE=1:2, v/v)
LC-MS: [M+1]⁺=219

Synthesis of Compound 2

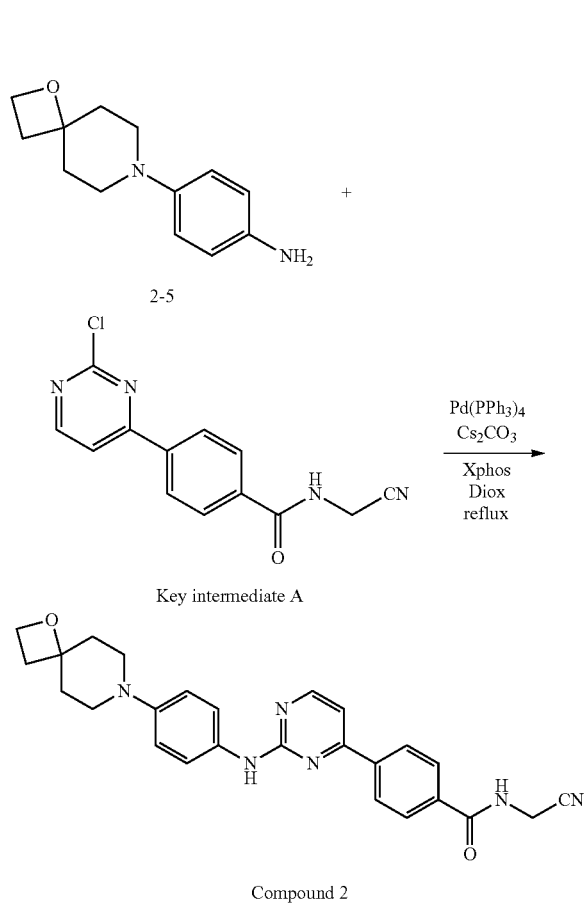

To a solution of 2-5 (160 mg, 0.73 mmol) and Key intermediate A (200 mg, 0.73 mmol) in dioxane (30 mL) under N₂, was added Pd(PPh₃)₄ (84 mg, 0.073 mmol), Cs₂CO₃ (587 mg, 1.46 mmol) and Xphos (35 mg, 0.073 mmol). The mixture was heated to reflux for 3 h. The reaction was allowed to cool to room temperature and poured into H₂O (50 mL). the Aqueous layer was extracted with EtOAc (50 mL×2) and the combined organic layers washed with brine (30 mL), dried (MgSO₄), filtered and concentrated. The crude residue obtained was purified by silica gel column chromatography with (CH₂Cl₂/CH₃OH=40/1-40/3) to give analogue 2 (80 mg, 24%) as pale yellow solid. The structure was confirmed by LC-MS and H-NMR spectra.

TLC: Rf=0.32 (silica gel, MeOH/CH₂Cl₂=1/40, v/v)

LC-MS: [M+1]⁺=455

¹H-NMR (400 MHz, d₆-DMSO) δ (ppm): 9.49 (s, 1H), 9.37 (d, J=4.9 Hz, 1H), 8.53 (d, J=5.0 Hz, 1H), 8.27 (d, J=8.2 Hz, 2H), 8.02 (d, J=8.2 Hz, 2H), 7.63 (d, J=8.6 Hz, 2H), 7.40 (d, J=5.1 Hz, 1H), 6.93 (d, J=8.7 Hz, 2H), 4.46-4.31 (m, 4H), 3.19 (dd, J=8.5, 3.8 Hz, 2H), 2.98 (dd, J=4.8, 2.5 Hz, 2H), 2.37 (t, J=7.6 Hz, 2H), 1.87 (dd, J=13.7, 6.9 Hz, 4H).

Example 3

Synthesis of Compound 3

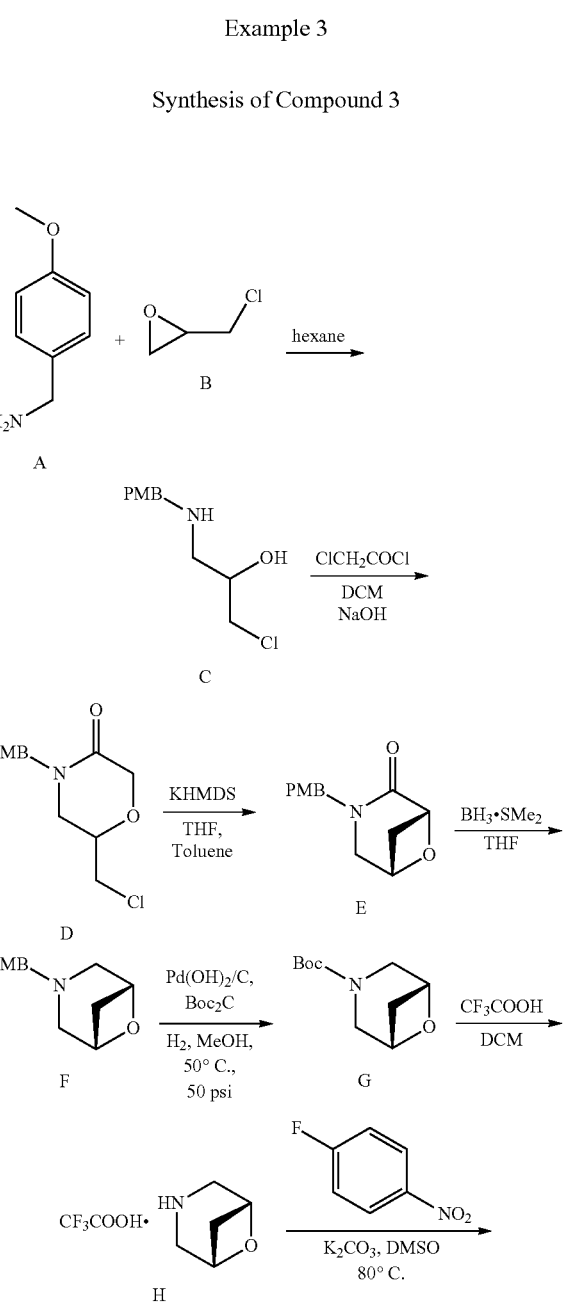

-continued

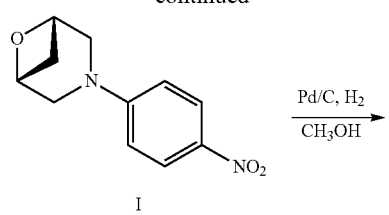

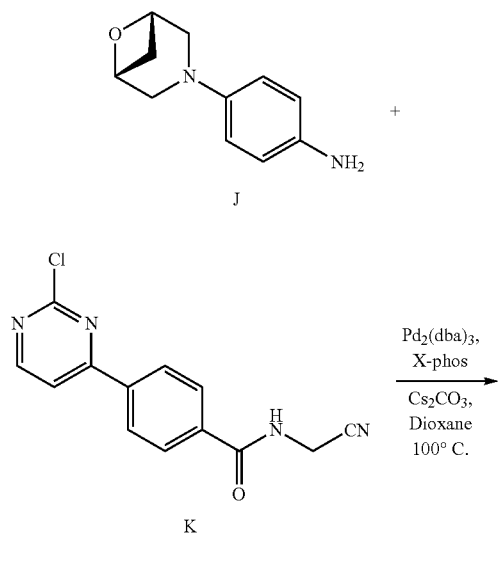

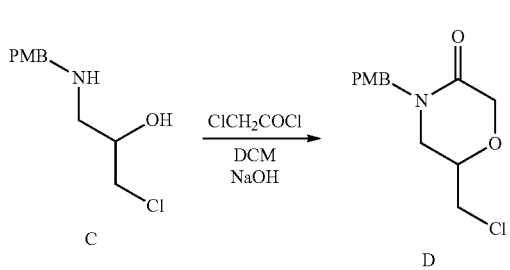

and MTBE to give the desired product (40 g, 48%) as a white solid. LC-MS: 229.9 ([M+1]⁺).

Synthesis of 6-Chloromethyl-4-(4-methoxy-benzyl)-morpholin-3-one

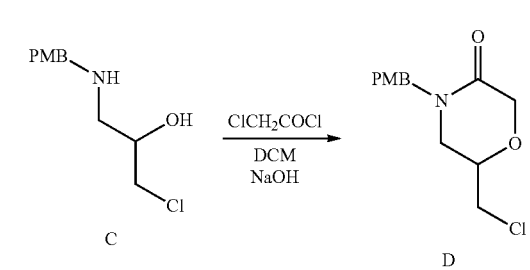

To a solution of C (18 g, 78.4 mmol) in DCM (200 mL) was added 1.0 M aq NaOH (85 mL) and the solution cooled 0° C. A solution of ClCH₂COCl (8.5 mL, 112.9 mmol) in DCM (50 mL) was added dropwise and the reaction stirred at 0° C. for 1 h. The reaction was warmed to RT and 10.0 M aq NaOH (60 mL) was added, the mixture was stirred for a further 4 h, then diluted with water and the layers were separated. The aqueous layer was extracted with DCM and the combined organic layers washed with water, dried (Na₂SO₄), filtered and concentrated to give crude product, which was purified on silica gel with Pet ether/EtOAc (10:1 to 4:1) to give the desired product (11 g, 52%) as a light yellow oil. LC-MS: 291.8 ([M+Na]⁺).

Synthesis of 3-(4-Methoxy-benzyl)-6-oxa-3-aza-bicyclo[3.1.1]heptan-2-one

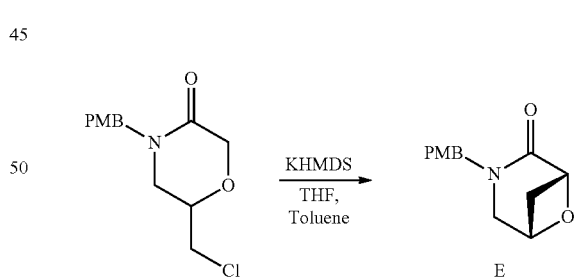

Synthesis of 1-Chloro-3-(4-methoxy-benzylamino)-propan-2-ol

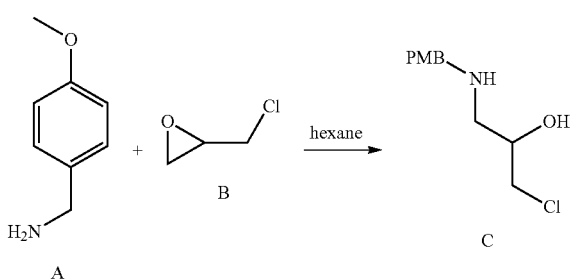

A mixture of A (50 g, 364.5 mmol) and B (34 g, 367.5 mmol) in hexane (80 mL) was stirred at RT overnight. The mixture was filtered and the filter cake washed with hexane To a stirred solution of D (8 g, 29.7 mmol) in THF (140 mL) and toluene (140 mL) at 0° C. was added dropwise a solution of KHMDS (1.0 M in THF 50 mL) and the reaction stirred for 1 h. The reaction was quenched by addition of aq NH₄Cl (150 mL), and for 20 minutes at 0° C. The mixture was filtered and the filter cake was washed with EtOAc. The layers was separated and the aqueous layer extracted with EtOAc, the combined organic layers were washed with water, dried (MgSO₄), filtered and concentrated to give crude product (7.5 g, 100%)

Synthesis of 3-(4-Methoxy-benzyl)-6-oxa-3-aza-bicyclo[3.1.1]heptane

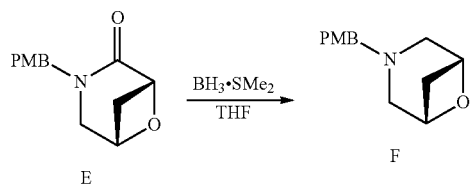

To a solution of E (5.6 g, 24 mmol) in THF (130 mL) was added dropwise 2.0 M BH$_3$ in Me$_2$S (30.9 mL) at 0° C. The reaction was then warmed to RT and stirred overnight. The reaction was quenched by addition of MeOH and stirred at RT for 30 minutes. Aqueous K$_2$CO$_3$ was added and the mixture heated at 60° C. for 30 minutes. The mixture was cooled to RT and the mixture extracted with EtOAc, the combined organic layers were dried (Na$_2$SO$_4$), filtered and evaporated to give crude product which was purified on silica gel with Pet ether/EtOAc (8:1 to 1:1) to give F (2.5 g, 47%) as a colorless oil. LC-MS: 220.0 ([M+1]$^+$).

Synthesis of 6-Oxa-3-aza-bicyclo[3.1.1]heptane-3-carboxylic acid tert-butyl ester

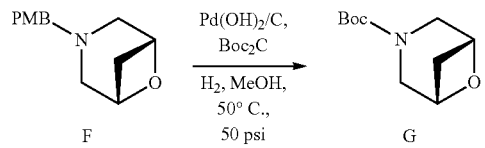

To a solution of F (1.0 g, 4.6 mmol) in MeOH (60 mL) was added Boc$_2$O (2.0 g, 9.3 mmol) and Pd(OH)$_2$ on activated carbon (1.0 g, 10%) and the mixture stirred at 50° C. under a H$_2$ atmosphere (50 psi) overnight. LCMS showed the reaction was complete. The mixture was filtered and the filter cake was washed with MeOH. The filtrate was concentrated to give the crude product (1.1 g, 100%) as a colorless oil without any purification. LC-MS: 222.0 ([M+Na]$^+$).

Synthesis of 6-Oxa-3-aza-bicyclo[3.1.1]heptane

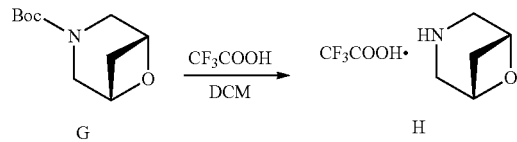

To a solution of G (900 mg, 4.5 mmol) in DCM (20 mL) was added dropwise a solution of CF$_3$COOH (6.0 g) in DCM (10 mL) at 0° C. The reaction was stirred at RT for 3 h. LCMS showed the reaction was complete. The solvent was removed in vacuo to give the crude product (1.3 g, 100%) as colorless oil which was used directly in the next step. LC-MS: 99.8 ([M+1]$^+$).

Synthesis of (1S,5R)-3-(4-nitrophenyl)-6-oxa-3-aza-bicyclo[3.1.1]heptane

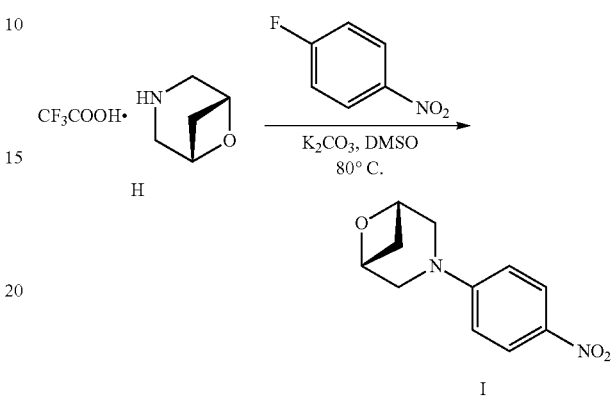

To a stirred mixture of H (720 mg, 3.41 mmol) in DMSO (20 mL) was added 1-fluoro-4-nitrobenzene (481 mg, 3.41 mmol) and K$_2$CO$_3$ (1.89 g, 13.64 mmol). The mixture was heated to 90° C. and stirred for 4 h. TLC showed the reaction was complete. The mixture was poured into water (50 mL) and extracted with EtOAc. The combined organic layers were washed with brine, dried (MgSO$_4$), filtered and concentrated. A precipitate was formed during evaporation of the solvent and it was collected to get 130 mg of the product. The filtrate was concentrated and purified by silica gel column (Pet ether/EtOAc=5/1) to get a further 50 mg of the desired product (total yield 180 mg 24%). LC-MS: 220.9 ([M+1]$^+$).

Synthesis of 4-((1S,5R)-6-oxa-3-aza-bicyclo[3.1.1]heptan-3-yl)benzenamine

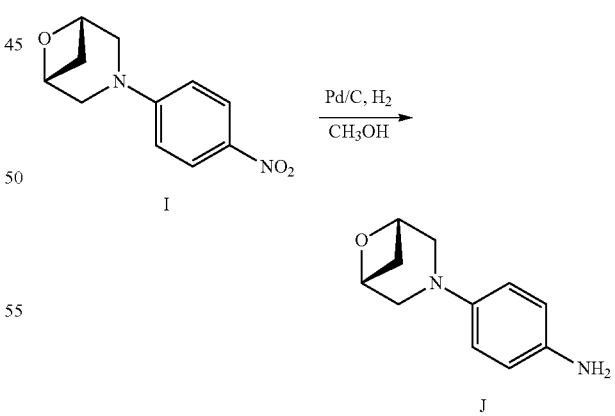

To a solution of I (180 mg, 0.82 mmol) in CH$_3$OH (30 mL) was added Pd/C (10%, 18 mg) and the mixture was stirred under a H$_2$ atmosphere at RT for 3 h. The mixture was filtered through a pad of Celite and the filter cake was washed with CH$_3$OH. The filtrate was concentrated to give the desired product (140 mg, 90%) as a brown solid. LC-MS: 191.0 ([M+1]$^+$).

45

Synthesis of 4-(6-(4-((1S,5R)-6-oxa-3-aza-bicyclo[3.1.1]heptan-3-yl)phenylamino)pyrimidin-4-yl)-N-(cyanomethyl)benzamide

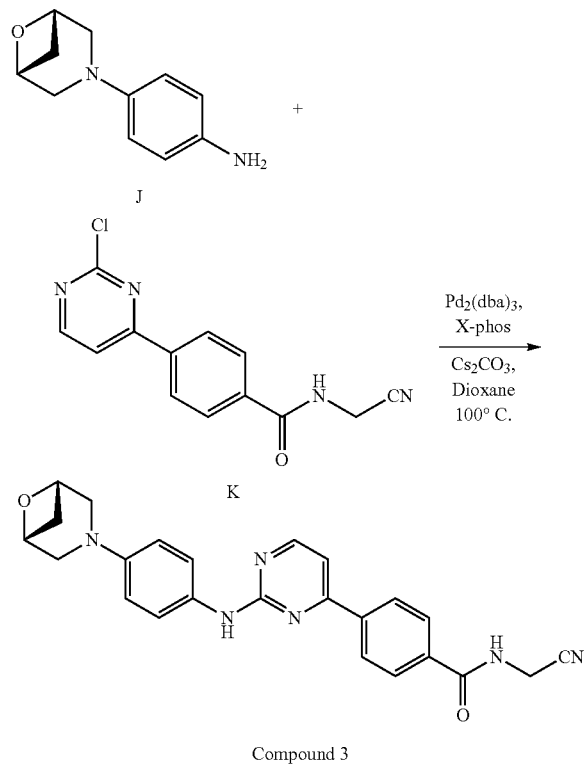

Compound 3

To a solution of J (140 mg, 0.74 mmol) and K (202 mg, 0.74 mmol) in dioxane (20 mL) was added Pd$_2$(dba)$_3$ (64 mg, 0.07 mmol), X-phos (33 mg, 0.07 mmol) and Cs$_2$CO$_3$ (531 mg, 1.63 mmol) at RT under N$_2$. The mixture was heated to 100° C. and stirred for 5 h. The mixture was cooled to RT and filtered; to the filtrate was added H$_2$O (50 mL). The product was extracted with EtOAc and the combined organic layers dried (Na$_2$SO$_4$), filtered and evaporated to give crude product which was purified by silica gel chromatography (PE/EA=1/1-CH$_2$Cl$_2$/CH$_3$OH=50/1) to get the desired product (100 mg, 32%). LC-MS: 426.2 ([M+1]$^+$), 1H-NMR (400 MHz, DMSO-d$_6$) δ 9.38 (s, 1H), 9.34 (t, J=5.6 Hz, 1H), 8.50 (d, J=5.2 Hz, 1H), 8.26 (d, J=8.4 Hz, 2H), 8.01 (d, J=8.4 Hz, 2H), 7.63 (d, J=8.8 Hz, 2H), 7.36 (d, J=5.2 Hz, 1H), 6.72 (d, J=8.8 Hz, 2H), 4.70 (d, J=6.4 Hz, 2H), 4.34 (d, J=5.6 Hz, 2H), 3.54 (d, J=11.2 Hz, 2H), 3.34 (d, J=11.2 Hz, 2H), 3.10 (q, J=6.8 Hz, 1H), 1.94 (d, J=8.4 Hz, 1H).

Example 4

Synthesis of Compound 4

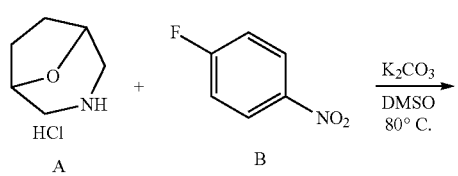

46

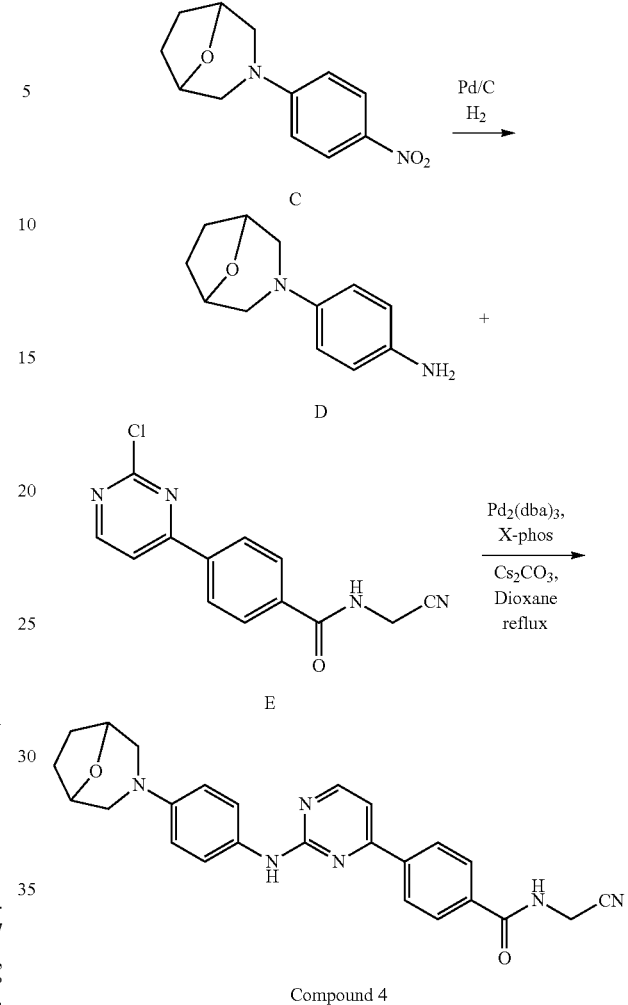

Compound 4

Synthesis of 3-(4-nitrophenyl)-8-oxa-3-azabicyclo[3.2.1]octane

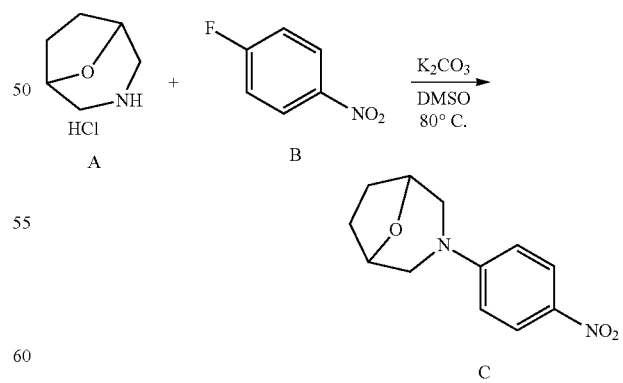

To a solution of A (200 mg, 1.34 mmol) and B (226 mg, 1.60 mmol) in DMSO (20 mL) was added K$_2$CO$_3$ (221 mg, 1.60 mmol) and the mixture was stirred at 80° C. overnight. To the mixture was added H$_2$O (50 mL) and the product was extracted with EtOAc (50 mL). The organic phase was washed with brine (50 mL), dried (MgSO₄), filtered and concentrated to give the crude product which was washed with 2-methoxy-2-methylpropane (15 mL) to give the product (240 mg, 76%) as a yellow solid. LC-MS: [M+1]+234.9.

Synthesis of 4-(8-oxa-3-azabicyclo[3.2.1]octan-3-yl)aniline

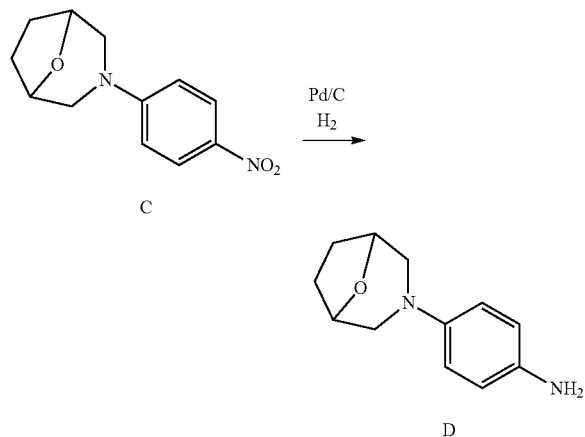

To a solution of C (550 mg, 2.2 mmol) in CH₃OH (30 mL) was added Pd/C (10%, 55 mg) and the mixture was stirred under an H₂ atmosphere at room temperature for 3 h. The mixture was filtered through a pad of celite and the filtrate was concentrated to give the crude product (480 mg) as a brown solid which was used in the next step without purification. LC-MS: 205.1 ([M+1]⁺).

Synthesis of 4-(2-((4-(8-oxa-3-azabicyclo[3.2.1]octan-3-yl)phenyl)amino)pyrimidin-4-yl)-N-(cyanomethyl)benzamide

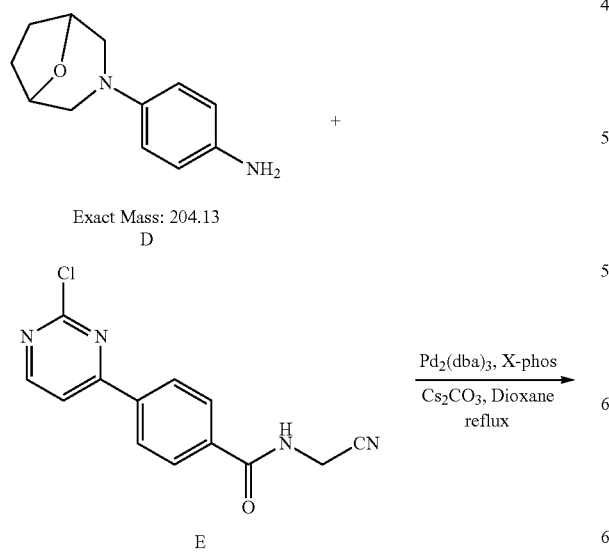

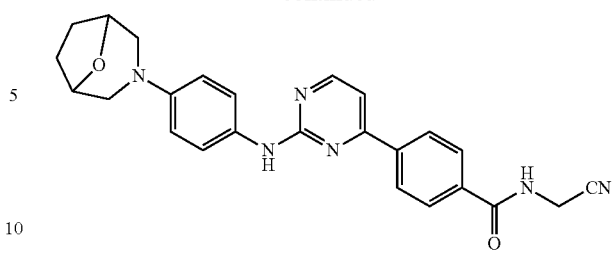

Compound 4

To a solution of D (220 mg, 1.08 mmol) and E (294 mg, 1.08 mmol) in dioxane (30 mL) was added Pd₂(dba)₃ (100 mg, 0.11 mmol), X-phos (52.4 mg, 0.11 mmol) and Cs₂CO₃ (870 mg, 2.16 mmol) under N₂. The mixture was stirred at 80° C. for 8 h. To the mixture was added H₂O (50 mL) and the product was extracted with CH₂Cl₂ (50 mL×3). The organic layer was washed with brine (100 mL), dried (MgSO₄), filtered and concentrated to get the crude product, which was purified by column chromatography (silica gel, CH₂Cl₂/CH₃OH=50/1-30/1) to afford the product (72 mg, 15%) as a yellow solid. LC-MS: 441.2 ([M+1]⁺), ¹H-NMR: 8.46 (d, J=5.2 Hz, 1H), 8.14 (d, J=8.4 Hz, 2H), 7.89 (d, J=8.4 Hz, 2H), 7.51 (d, J=8.8 Hz, 2H), 7.11 (d, J=5.2 Hz, 2H), 7.07 (s, 1H), 6.84 (d, J=9.2 Hz, 2H), 6.60 (t, J=5.6 Hz, 1H), 4.50 (s, 2H), 4.42 (d, J=6.0 Hz, 2H), 3.31 (d, J=11.2 Hz, 2H), 3.01 (dd, J1=2.4 Hz, J2=11.6H, 2H), 1.97 (s, 4H)

Example 5

Synthesis of Compound 5

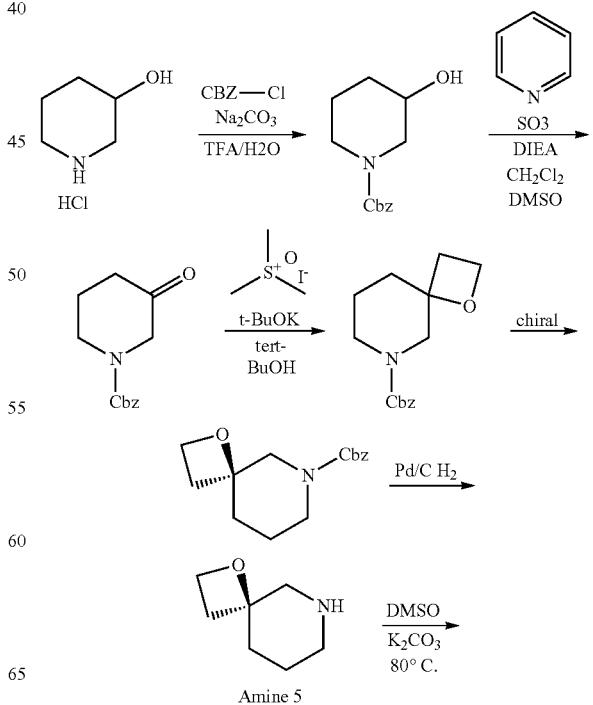

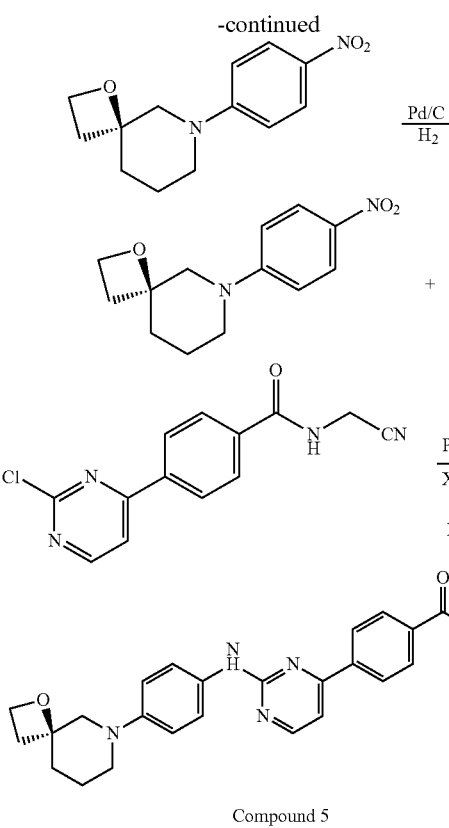

Compound 5

Synthesis of 5-B

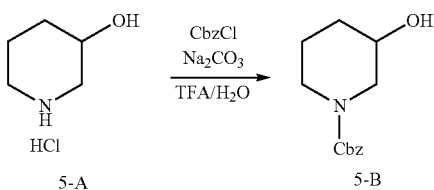 [SMILES: OC1CCCNC1 ; Cl ; O=C(OCc1ccccc1)N1CCCC(O)C1]

To a solution 5-A (10.00 g, 73 mmol) in THF/H$_2$O (50 mL/50 mL), was added Na$_2$CO$_3$ (23.10 g, 218 mmol). CbzCl (14.90 g, 87 mmol) was added dropwise and the reaction stirred at rt for 5 h. The mixture was extracted with EtOAc (100 mL×3) and the combined the organic layers washed with brine, dried (MgSO$_4$), filtered and concentrated. The residue obtained was purified by silica gel column chromatography with EtOAc/Pet ether=1/100~1/4 to give 5-B (16.50 g 96%) as a colorless oil. TLC: Rf=0.65 silica gel EtOAc/Pet ether=1/1 v/v Synthesis of 5-C

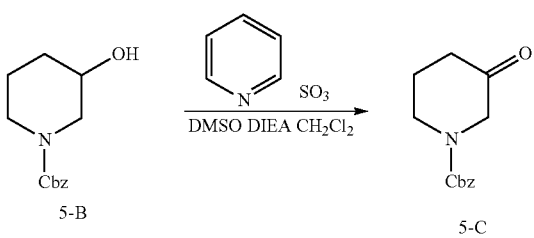

A stirred mixture of 5-B (16.50 g, 70 mmol) in CH2Cl2 (90 mL) was cooled to 0 and DIPEA (45.30 g, 0.35 mol) was added. Pyridine sulfur trioxide (25.70 g, 0.16 mol) in DMSO (100 mL) was added dropwise at that temperature and the reaction mixture stirred at 0 for 2 h. The mixture was poured into to 4M HCl and extracted with CH$_2$Cl$_2$ (100 mL×3). The organic layers were combined and washed with brine, dried (MgSO$_4$), filtered and concentrated. The residue obtained was purified by silica gel column chromatography with EtOAc/Pet ether=1/100~1/6 to give (14.90 g. 90%) as off-white solid. The structure was confirmed by LC-MS spectra. LC-MS: [M+1]$^+$=234

Synthesis of 5-D

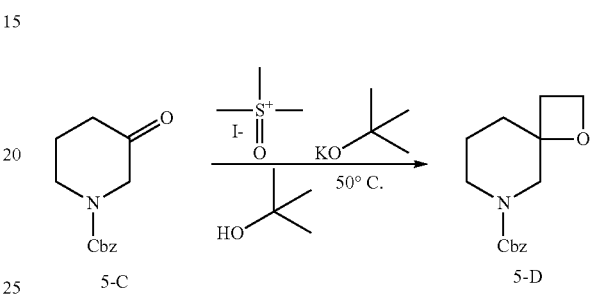

To a suspension of trimethylsulfoxonium iodide (35.20 g, 0.16 mol) in t-BuOH (150 mL) was added t-BuOK (17.95 g, 0.16 mol) at 50° C., the mixture turned to a cloudy suspension. The mixture was stirred at the same temperature for 1.5 h. Compound 5-C (14.90 g, 64 mmol) was then added at that temperature and the mixture stirred at 50° C. for another 48 h. The reaction mixture was cooled to room temperature and partitioned between saturated aqueous NH$_4$Cl and EtOAc. The organic phase was separated, dried (MgSO$_4$), filtered and concentrated under reduce pressure. The residue obtained was purified silica gel column chromatography (EtOAc/Pet ether=1/6) to give (2.0 g, 11%) as colorless oil. The structure was confirmed by LC-MS and H-NMR spectra.

TLC: Rf=0.52 silica gel EtOAc/Pet ether=1/1

LC-MS: 262 ([M+1]$^+$),

H-NMR: 7.33 (m, 5H), 5.14 (s, 2H), 4.66-4.43 (m, 2H), 3.82 (d, J=13.0 Hz, 1H), 3.67-3.07 (m, 3H), 2.37 (m, 2H), 1.99-1.35 (m, 4H).

Separated with Chiral HPLC

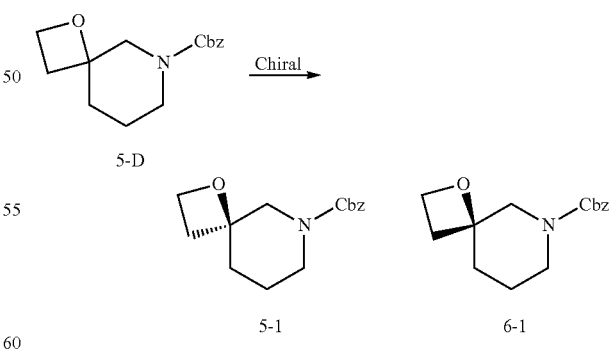

Racemic benzyl 1-oxa-6-azaspiro[3.5]nonane-6-carboxylate was submitted to preparative chromatography for enantiomeric separation using a CHIRALPAK ADH column (0.46 cm I.D.×15 cm L) and 100% EtOH as eluent (Flowrate: 0.5 mL/min). Concentration in vacuo to afforded peak 1 (0.90 g) as an oil and peak 2 (0.76 g) as an oil.

Synthesis of 5-2

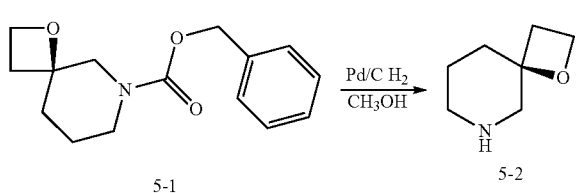

To a solution of 5-1 (900 mg, 3.44 mmol) in CH₃OH (15 mL) was added 10% Pd/C (180 mg) and the reaction stirred under a hydrogen atmosphere (45 psi) at 80° C. for 5 hours. The reaction mixture was filtered through a pad of Celite and washed with EtOAc. The filtrate was concentrated to give 5-2 (438 mg, 100%) which was used for the next step without further purification. The structure was confirmed by LC-MS spectra. LC-MS: [M+1]$^+$=128, [2M+1]$^+$=255.

Synthesis of 5-3

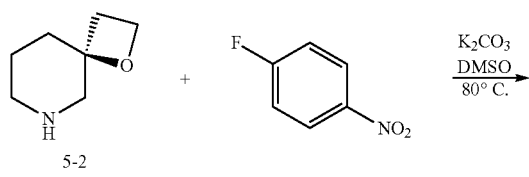

To a solution of 5-2 (438 mg, 3.05 mmol) in DMSO (15 mL) was added 1-fluoro-4-nitrobenzene (430 mg, 3.05 mmol) and K₂CO₃ (506 mg, 3.66 mmol). The mixture was stirred at 80° C. for 5 hours. The reaction mixture was allowed to cool to room temperature. Water was added and the aqueous layer extracted with EtOAc. The organic layers were combined, washed with brine, dried (MgSO4), filtered and concentrated. The crude residue was purified by column chromatography (Pet ether/EtOAc, 6:1~4:1) to give 5-3 (469 mg, 62%).

TLC: R$_f$=0.37 (silica gel, Petrol ether: EtOAc=1:1, v/v)

LC-MS: [M+1]$^+$=249, [M+Na]=271.

Synthesis of 5-4

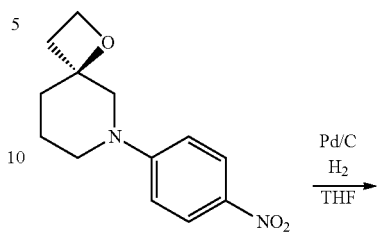

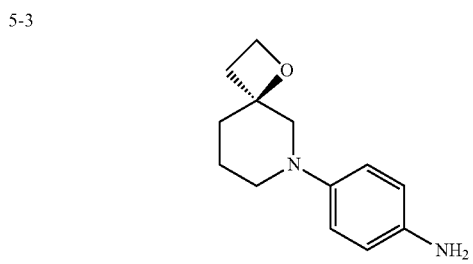

To a solution of 5-3 (360 mg, 1.45 mmol) in THF (20 mL) was added 10% Pd/C (53 mg) and the reaction stirred under a hydrogen atmosphere overnight. The catalyst was removed by filtration through a pad of Celite and washed with EtOAc. The filtrate was concentrated under reduce pressure to give 5-4 (317 mg, 100%), which was used for the next step without further purification. The structure was confirmed by LC-MS spectra.

TLC: R$_f$=0.30 (silica gel, Petrol ether: EtOAc=1:1, v/v)

LC-MS: [M+1]$^+$=219.

Synthesis of Compound 5

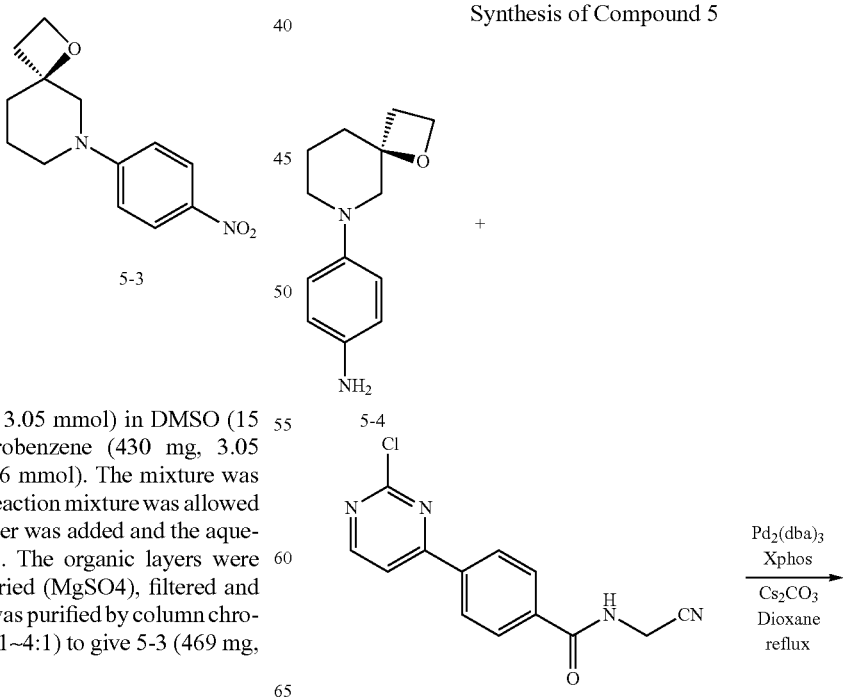

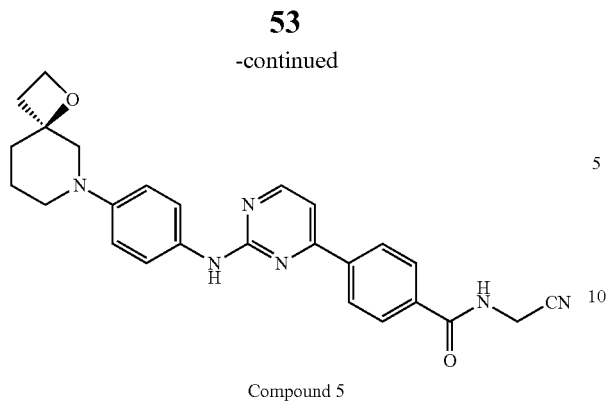

Compound 5

To a solution of 5-4 (250 mg, 1.14 mmol), Key intermediate A (312 mg, 1.14 mmol) and Cs$_2$CO$_3$ (750 mg, 2.28 mmol) in dioxane (15 mL) was added Xphos (55 mg. 0.114 mmol) and Pd2(dba)3 (105 mg, 0.114 mmol). The reaction mixture was stirred under a nitrogen atmosphere at 100° C. for 7 hours. The reaction was allowed to cool to room temperature, filtered through a pad of Celite and washed with EtOAc. The mixture was partitioned between EtOAc and H$_2$O and the aqueous layer was extracted with EtOAc. The combined organic layers were washed with brine, dried (MgSO$_4$), filtered and concentrated under reduce pressure. The residue obtained was purified by column chromatography (Pet ether/EtOAc=5:1~1:1 then CH$_2$Cl$_2$:CH$_3$OH=50:1) to give a pale yellow solid. The solid obtained was suspended in methanol (5 mL) and stirred for 30 min, filtered, washed with MTBE and dried under reduce pressure to give analogue 5 (65 mg, 8%) as pale yellow solid. The structure was confirmed by LC-MS and H-NMR spectra.

TLC: R$_f$=0.13 (silica gel, Petrol ether:EtOAc=1:1, v/v)
LC-MS: [M+1]$^+$=455
$^1$H NMR (400 MHz, CDCl$_3$) δ (ppm): 8.47 (d, J=5.1 Hz, 1H), 8.13 (d, J=8.3 Hz, 2H), 7.89 (d, J=8.3 Hz, 2H), 7.53 (d, J=8.9 Hz, 2H), 7.18-7.05 (m, 2H), 7.00 (d, J=8.8 Hz, 2H), 6.66 (t, J=5.3 Hz, 1H), 4.61 (d, J=3.3 Hz, 2H), 4.42 (d, J=5.7 Hz, 2H), 3.44 (d, J=11.6 Hz, 1H), 3.21-3.12 (m, 1H), 3.07 (d, J=11.5 Hz, 1H), 2.89 (m, 1H), 2.48 (m, 2H), 2.03-1.62 (m, 4H).

Example 6

Synthesis of Compound 6

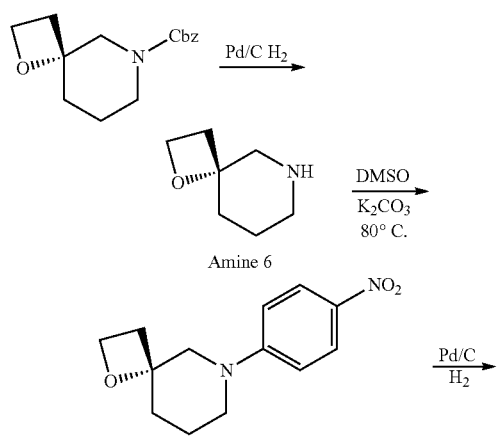

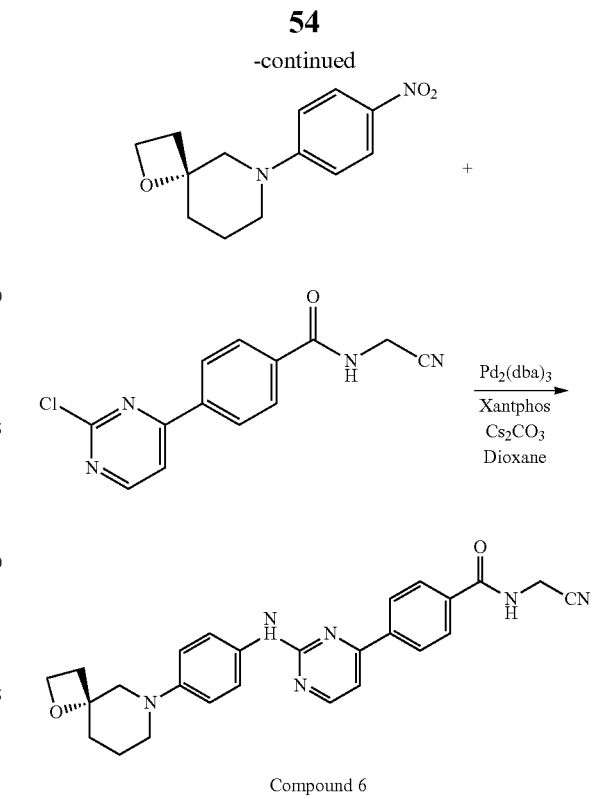

Compound 6

Synthesis of 6-2

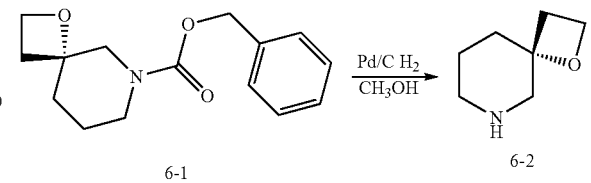

To a solution of 6-1 (766 mg, 2.93 mmol) in CH$_3$OH (15 mL) was added 10% Pd/C (180 mg) and the reaction stirred at 80° C. under an atmosphere of hydrogen for 5 hours. The reaction mixture was allowed to cool to room temperature and the catalyst removed by filtration through a pad of Celite. The filtrate was concentrated to give 6-2 (372 mg, 100%) of crude product which was used for the next step without further purification. The structure was confirmed by LC-MS spectra.
LC-MS: [M+1]=128

Synthesis of 6-3

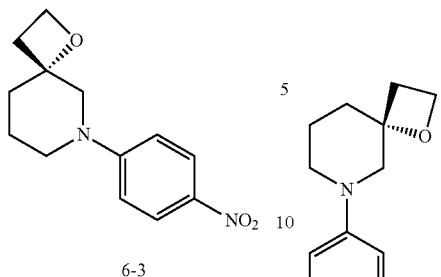

6-3

A solution of 6-2 (330 mg, 2.59 mmol) in DMSO (15 mL) was added 1-fluoro-4-nitrobenzene (370 mg, 2.59 mmol) and $K_2CO_3$ (429 mg, 3.11 mmol). The mixture was stirred at 80° C. for 5 hours then allowed to cool to room temperature. Water was added and the aqueous layer extracted with EtOAc. The organic layers were combined and washed with brine, dried (MgSO4), filtered and concentrated under reduce pressure. The residue obtained was purified by column chromatography (Pet ether:EtOAc=6:1~4:1) to give 6-2 (318 mg, 49%). The structure was confirmed by LC-MS spectra. TLC: $R_f$=0.37 (silica gel, Petrol ether:EtOAc=1:1, v/v)

LC-MS: [M+1]=249.

Synthesis of 6-4

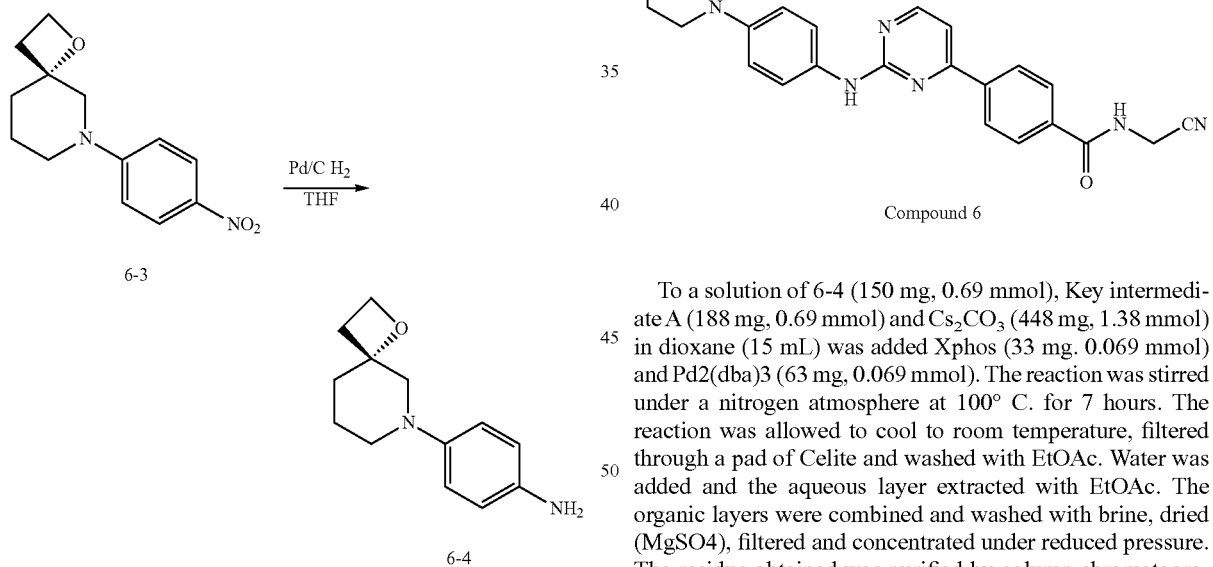

6-3

6-4

To a solution of 6-3 (318 mg, 1.28 mmol) in THF (20 mL) was added 10% Pd/C (32 mg) and the reaction stirred at room temperature under a hydrogen atmosphere overnight. The catalyst was removed by filtration through a pad of Celite and the filter pad washed with EtOAc. The filtrate was concentrated under reduce pressure to give 6-4 (280 mg, 100%) of crude product, which was used for the next step without further purification. The structure was confirmed by LC-MS spectra. TLC: $R_f$=0.30 (silica gel, Petrol ether:EtOAc=1:1, v/v)

LC-MS: [M+1]$^+$=219

Synthesis of Compound 6

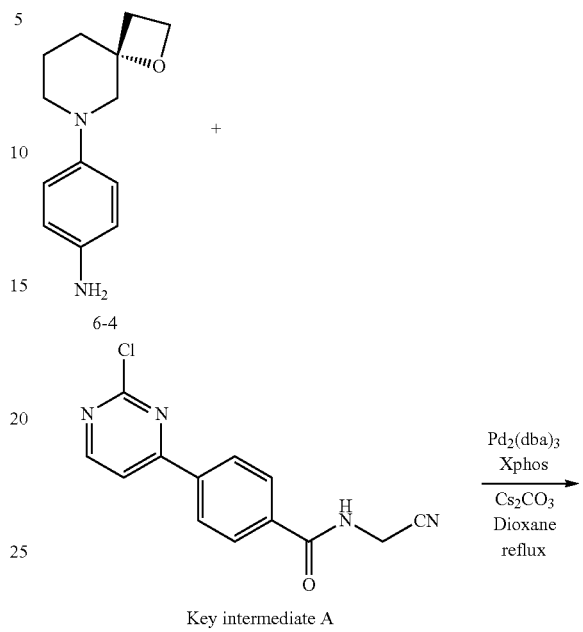

6-4

Key intermediate A

Compound 6

To a solution of 6-4 (150 mg, 0.69 mmol), Key intermediate A (188 mg, 0.69 mmol) and $Cs_2CO_3$ (448 mg, 1.38 mmol) in dioxane (15 mL) was added Xphos (33 mg. 0.069 mmol) and Pd2(dba)3 (63 mg, 0.069 mmol). The reaction was stirred under a nitrogen atmosphere at 100° C. for 7 hours. The reaction was allowed to cool to room temperature, filtered through a pad of Celite and washed with EtOAc. Water was added and the aqueous layer extracted with EtOAc. The organic layers were combined and washed with brine, dried (MgSO4), filtered and concentrated under reduced pressure. The residue obtained was purified by column chromatography (Pet ether/EtOAc=5:1~1:1 then $CH_2Cl_2$:$CH_3OH$=80:1) to afford a pale yellow solid. The solid was suspended in methanol (2 mL) and stirred for 30 min and collected by filtration, washing with MTBE. The solid was dried under reduced pressure to give analogue 5 (83 mg, 26%) as pale yellow solid. The structure was confirmed by LC-MS and H-NMR spectra. TLC: $R_f$=0.13 (silica gel, Petrol ether: EtOAc=1:1, v/v)

LC-MS: [M+1]$^+$=455

$^1$H NMR (400 MHz, $CDCl_3$) δ (ppm): 8.44 (d, J=5.1 Hz, 1H), 8.08 (d, J=8.4 Hz, 2H), 7.86 (d, J=8.4 Hz, 2H), 7.51 (d, J=8.8 Hz, 2H), 7.16 (s, 1H), 7.08 (d, J=5.2 Hz, 1H), 6.96 (m, 2H), 4.67-4.53 (m, 2H), 4.40 (d, J=5.7 Hz, 2H), 3.39 (d, J=11.6 Hz, 1H), 3.11 (m, 2H), 2.93 (m, 1H), 2.57-2.38 (m, 2H), 2.01-1.66 (m, 4H).

Example 7

Synthesis of Compound 7

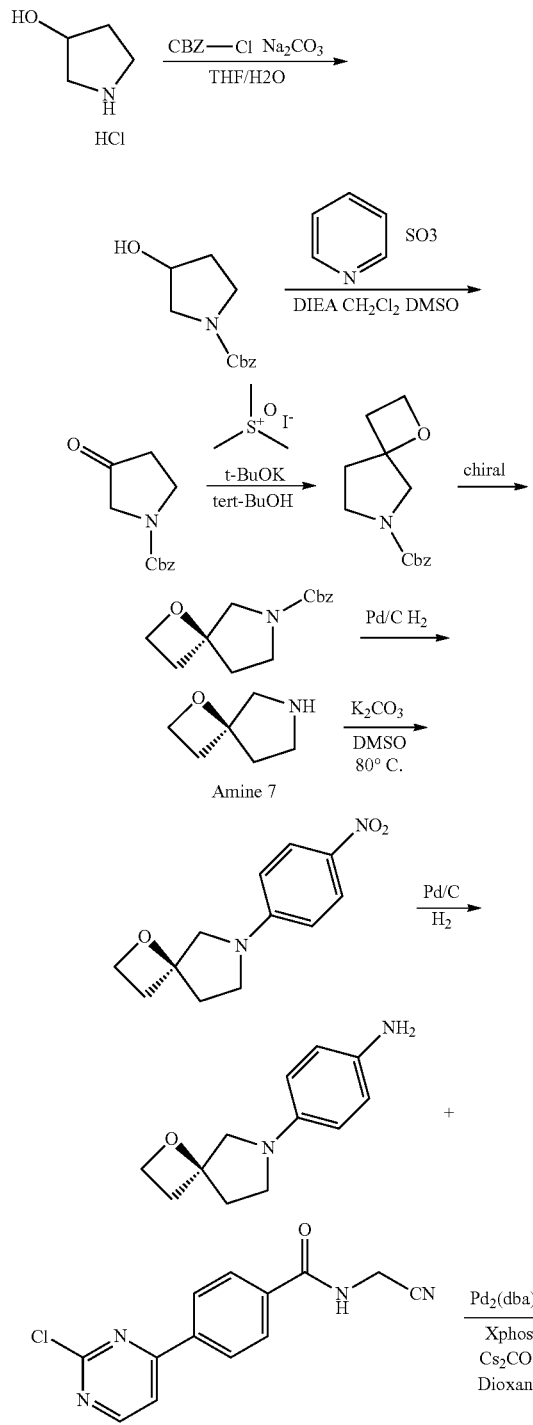

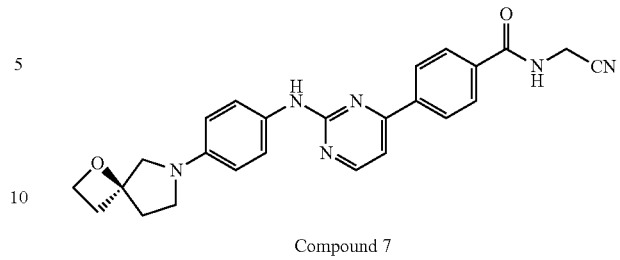

Compound 7

Synthesis of B

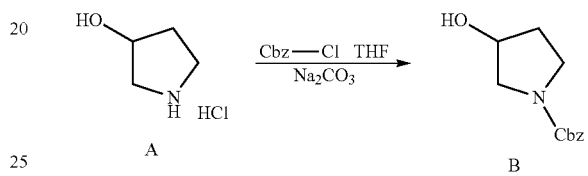

To a stirred solution of intermediate A (10.00 g, 81 mmol) in H₂O/THF=1/1 (200 mL) was added Na₂CO₃ (24.30 g 0.23 mol) and Cbz-Cl (23.50 g, 0.14 mol). The resulting mixture was stirred at r.t for 1 h. The reaction was quenched by addition of 1M HCl and the aqueous layer extracted twice with DCM. The combined organic layers were then washed with brine, dried (Na₂SO₄) filtered and concentrated. The crude product was purified by flash chromatography (EtOAc/Pet ether=1:4) to give B (15.50 g 87%) as white solid. The structure was confirmed by LC-MS spectra. TLC: Rf=0.3 (silica gel, EA:PE=1:2, v/v)

LC-MS: [M+H]⁺=222; [M+23]=244.

Synthesis of C

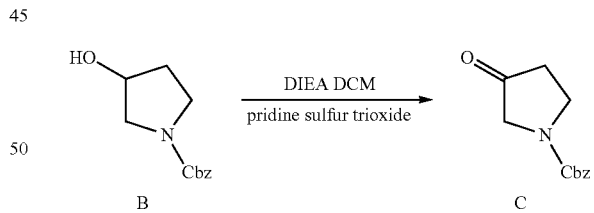

To a stirred solution of intermediate B (15.50 g, 0.07 mol) in DCM (100 mL) was added DIPEA (35.2 mL 0.21 mol) at 0° C. A solution of pyridine sulfur trioxide (25.2 g, 0.16 mol) in DMSO (70 mL) was added dropwise and the resulting mixture stirred at 0° C. for 1 h. The reaction was quenched by addition of H₂O and the aqueous layer was extracted twice with DCM. The combined organic layers were washed with brine, dried (Na₂SO₄), filtered and concentrated. The crude product obtained was purified by flash chromatography (EtOAc/Pet ether=1:2) to give compound C (13.80 g, 90%) as yellow solid. It's structure was confirmed by LC-MS spectra. TLC: Rf=0.7 (silica gel, EA:PE=1:1, v/v)

LC-MS: [M+23]=242.

Synthesis of D

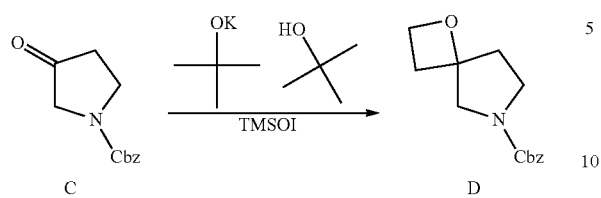

To a stirred solution of trimethylsulfoxonium iodide (32.70 g, 0.15 mol) in t-BuOH (100 mL) was added t-BuOK (14.30 g 0.13) and the reaction stirred at 50° C. for 1 h. Intermediate C (13.00 g 60 mmol) was then added and the resulting mixture was stirred at 50° C. for a further 48 h. The reaction mixture was quenched by addition of saturated $NH_4Cl$ solution and partitioned against EtOAc. The aqueous layer was extracted twice with EtOAc and the combined organic layers were then washed with brine, dried ($Na_2SO_4$), filtered and concentrated. The crude product was purified by flash chromatography (EtOAc/Pet ether=1:2) to give D (2.70 g 18%) as yellow oil. The structure was confirmed by LC-MS and H-NMR spectra.

TLC: Rf=0.36 (silica gel, EA:PE=1:2, v/v)

LC-MS: $[M+H]^+$=248; [M+Na]=270

H-NMR (400 MHz, $CDCl_3$) δ (ppm): 7.37 (m, 5H), 5.14 (d, 2H), 4.53 (m, 2H), 3.85-3.47 (m, 4H), 2.67 (m, 2H), 2.38-1.98 (m, 2H).

Separated with Chiral HPLC

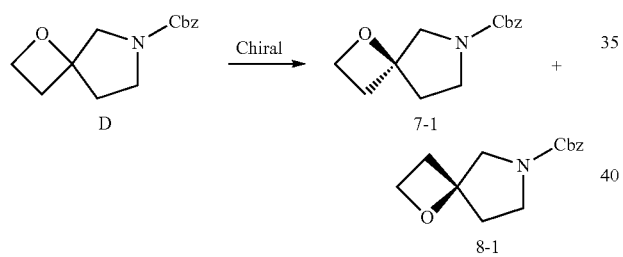

Racemic benzyl 1-oxa-6-azaspiro[3.4]octane-6-carboxylate was submitted to preparative chromatography for using a CHIRALPAK AYH column (0.46 cm I.D.×15 cm L). Hexane/EtOH=50/50 was used as eluent (Flowrate: 1 mL/min). Concentrated in vacuo gave peak 1 (1.12 g) as an oil and peak 2 (1.33 g) as an oil.

Synthesis of 7-2

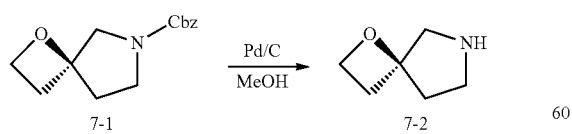

To a stirred solution of intermediate 7-1 (1.10 g, 4.5 mmol) in MeOH (20 mL) was added 10% Pd/C (110 mg) and the reaction heated at reflux under a hydrogen atmosphere for 2 days. The reaction was allowed to cool to room temperature and then filtered through a pad of Celite. The filter pad was washed with MeOH and the filtrate concentrated under reduced pressure to give 7-2 (490 mg, 97%) as an oil. The structure was confirmed by LC-MS. It was used for the next step without further purification.

TLC: Rf=0.04 (silica gel, EA:PE=1:2, v/v)

LC-MS: $[M+1]^+$=114.

Synthesis of 7-3

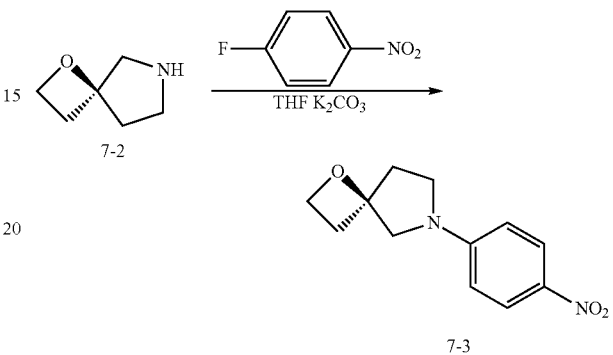

To a stirred solution of 7-2 (490 mg, 4.3 mmol) in THF (50 mL) was added $K_2CO_3$ (718 mg, 5.2 mmol), followed by 1-fluoro-4-nitrobenzene (612 mg, 4.3 mmol). The resulting mixture was stirred at 80° C. for 5 h. The reaction was allowed to cool to room temperature and poured into water. The aqueous layer was extracted with EtOAc and the combined organic layers washed with brine, dried ($Na_2SO_4$), filtered and concentrated. The crude product obtained was purified by flash chromatography (EtOAc/Pet ether=1:2) to give 7-3 (560 mg 55%) as yellow solid. The structure was confirmed by LC-MS.

TLC: Rf=0.4 (silica gel, EA:PE=1:2, v/v)

LC-MS: $[M+H]^+$=235; [M+Na]=257

Synthesis of 7-4

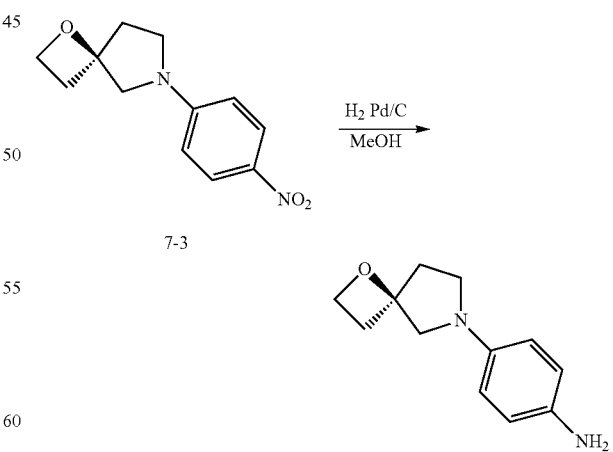

To a stirred solution of 7-3 (560 mg, 2.4 mmol) in MeOH (20 mL) was added 10% Pd/C (50 mg) and the reaction stirred under a hydrogen atmosphere overnight. The catalyst was removed by filtration through Celite and the filtrate was concentrated under reduced pressure to give 7-4 (486 mg, 99%) as red solid. The structure was confirmed by LC-MS. It was used for the next step without further purification.

TLC: Rf=0.25 (silica gel, EA:PE=1:1, v/v)

LC-MS: [M+H]$^+$=205.

Synthesis of Compound 7

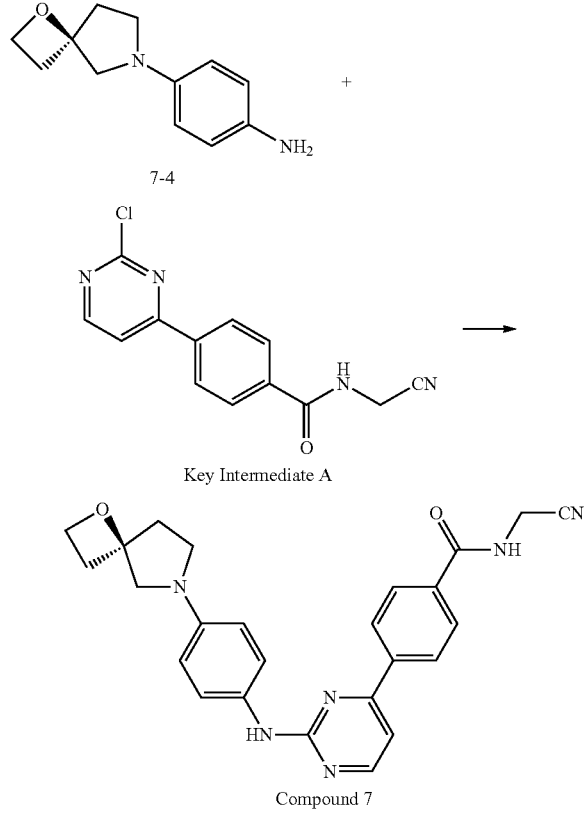

Compound 7

To a stirred solution of 7-4 (243 mg, 1.19 mmol) in dioxane (40 mL) was added Cs$_2$CO$_3$ (775 mg 2.38 mmol) and X-phos (57 mg 0.119 mmol), followed by Pd$_2$(dba)$_3$ (109 mg, 0.119 mmol). The resulting mixture was heated at 100° C. for 6 h under N$_2$. The reaction was filtered through a pad of celite and the filter pad washed with EtOAc. The filtrate was partitioned against water and the aqueous layer extracted twice with EtOAc. The combined organic layers were washed with brine, dried (Na$_2$SO$_4$), filtered and concentrated. The crude product obtained was purified by flash chromatography (MeOH/DCM=1:50) to give analogue 7 (165 mg, 31%) as a yellow solid. The structure was confirmed by LC-MS and H-NMR spectra.

TLC: Rf=0.4 (silica gel, MeOH/DCM=1:20, v/v)

LC-MS: [M+H]$^+$=441

H-NMR (400 MHz, d4-DMSO) δ (ppm): 9.36 (s, 2H), 8.51 (d, J=4.2 Hz, 1H), 8.26 (d, J=7.8 Hz, 2H), 8.01-7.98 (m, 2H), 7.66-7.52 (m, 2H), 7.37 (d, J=4.4 Hz, 1H), 6.60-6.48 (m, 2H), 4.50-4.31 (m, 4H), 3.58-3.52 (m, 1H), 3.29-3.22 (m, 2H), 2.81-2.62 (m, 2H), 2.39-2.11 (m, 2H).

Example 8

Synthesis of Compound 8

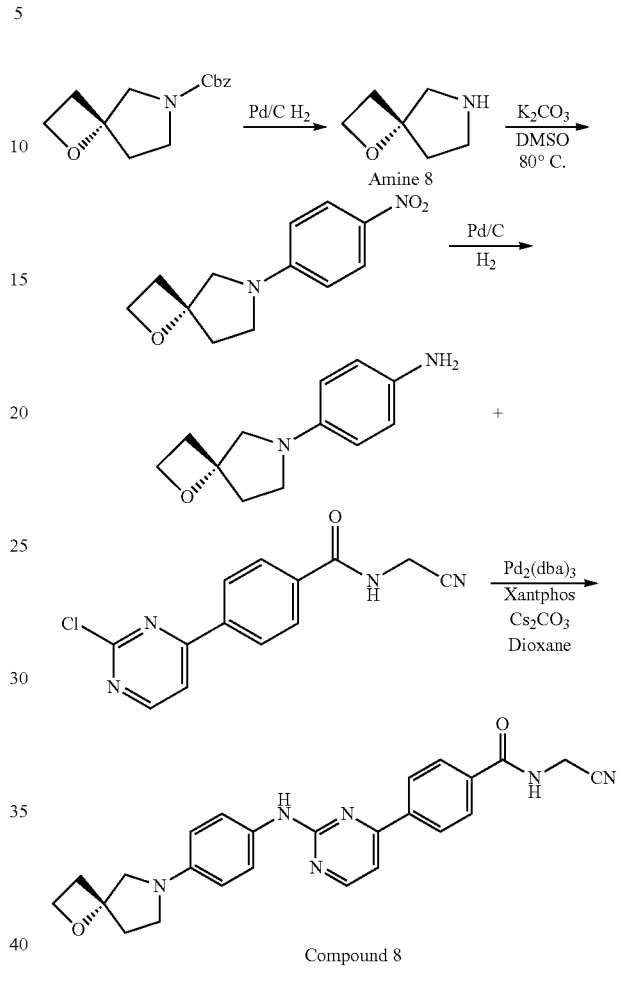

Compound 8

Synthesis of 8-2

To a stirred solution of 8-1 (1.33 g, 5.4 mmol) in MeOH (20 mL) was added 10% Pd/C (130 mg) and the reaction heated at 80° C. under a hydrogen atmosphere for 2 days. The catalyst was removed by filtration through a pad of Celite and the filter pad washed with MeOH. The filtrate was evaporated under reduced pressure to give 8-2 (608 mg 100%) as an oil. The structure was confirmed by LC-MS spectra. It was used for the next step without further purification.

TLC: Rf=0.04 (silica gel, EA:PE=1:2, v/v)

LC-MS: [M+1]$^+$=114.

Synthesis of 8-3

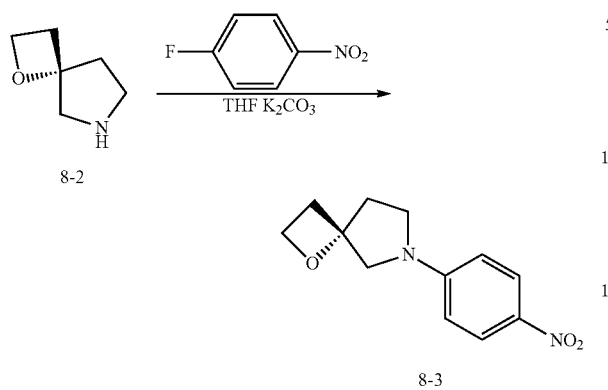

To a stirred solution of 8-2 (623 mg, 5.5 mmol) in THF (50 mL) was added K$_2$CO$_3$ (914 mg 6.6 mmol), followed by 1-fluoro-4-nitrobenzene (777 mg, 5.5 mmol). The resulting mixture was stirred at 80° C. for 5 h. The reaction mixture was allowed to cool to room temperature and poured into water. The aqueous layer was extracted twice with EtOAc and the combined organic layers were then washed with brine, dried (Na$_2$SO$_4$), filtered and evaporated to afford the crude product which was purified by flash chromatography (EtOAc/Pet.ether=1:2) to give 8-3 (677 mg, 52%) as yellow solid. The structure was confirmed by LC-MS spectra.

TLC: Rf=0.4 (silica gel, EA:PE=1:2, v/v)

LC-MS: [M+H]$^+$=235, [M+Na]=257.

Synthesis of 8-4

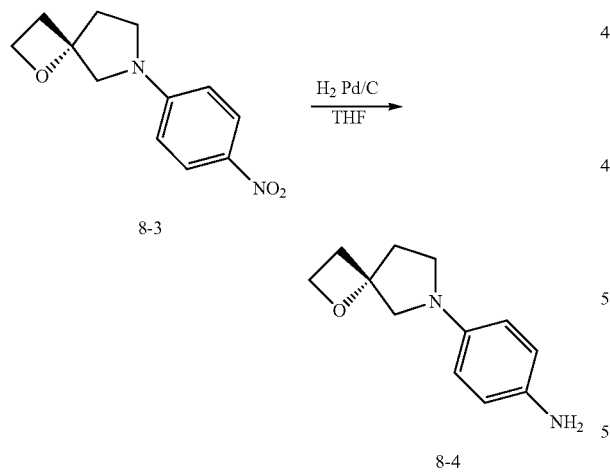

To a stirred solution of 8-3 (677 mg, 2.9 mmol) in MeOH (50 mL) was added 10% Pd/C (60 mg) and the reaction stirred under a hydrogen atmosphere overnight. The catalyst was removed by filtration through a pad of Celite and the filter pad washed with MeOH. The filtrate was concentrated under reduced pressure to give 8-4 (554 mg, 93%) as red solid.

The structure was confirmed by LC-MS spectra. TLC: Rf=0.25 (silica gel, EA:PE=1:1, v/v)

LC-MS: [M+1]$^+$=205.

Synthesis of Compound 8

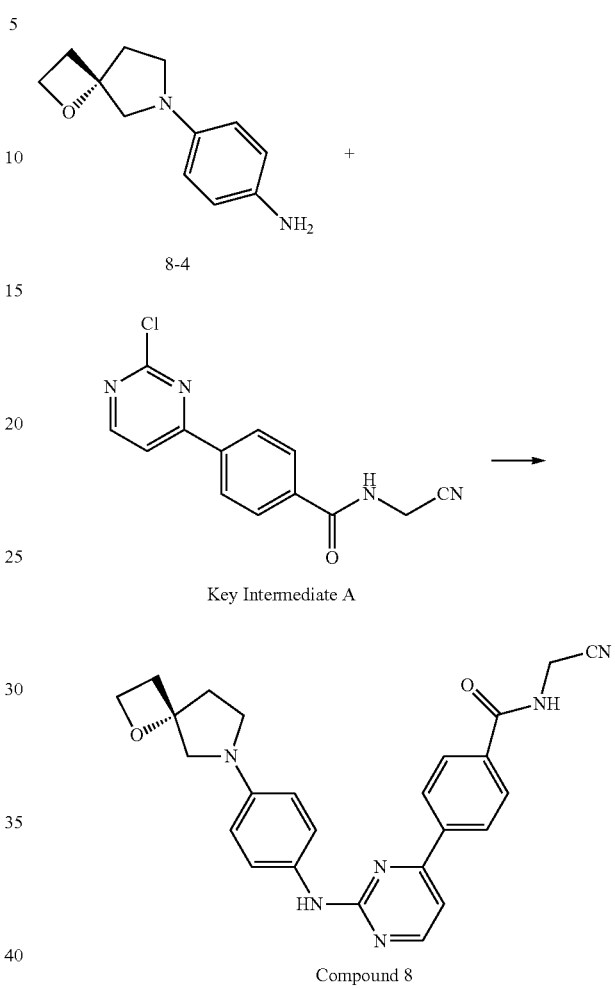

To a stirred solution of 8-4 (286 mg, 1.4 mmol) in dioxane (40 mL) was added Cs$_2$CO$_3$ (912 mg 2.8 mmol) and X-phos (67 mg 0.14 mmol), followed by Pd$_2$(dba)$_3$ (128 mg, 0.14 mmol). The resulting mixture was heated at 100° C. for 6 h under a nitrogen atmosphere. The catalyst was removed by filtration through a pad of celite and the pad washed with EtOAc. The filtrate was partitions against water and extracted twice with EtOAc. The combined organic layers were then washed with brine, dried (Na$_2$SO$_4$), filtered and concentrated under reduced pressure. The crude product was purified by flash chromatography (MeOH/DCM=1:50) to give analogue 8 (167 mg, 27%) as yellow solid. The structure was confirmed by LC-MS and H-NMR spectra.

TLC: Rf=0.4 (silica gel, MeOH/DCM=1:20, v/v).

LC-MS: 441 ([M+1]$^+$).

H-NMR (400 MHz, d6-DMSO) δ (ppm): 9.36 (s, 2H), 8.51 (d, J=4.2 Hz, 1H), 8.26 (d, J=7.8 Hz, 2H), 8.09-7.98 (m, 2H), 7.66-7.52 (m, 2H), 7.37 (d, J=4.4 Hz, 1H), 6.60-6.48 (m, 2H), 4.50-4.31 (m, 4H), 3.58-3.52 (m, 2H), 3.29-3.22 (m, 2H), 2.81-2.62 (m, 2H), 2.39-2.11 (m, 2H).

Example 9
Synthesis of Compound 9
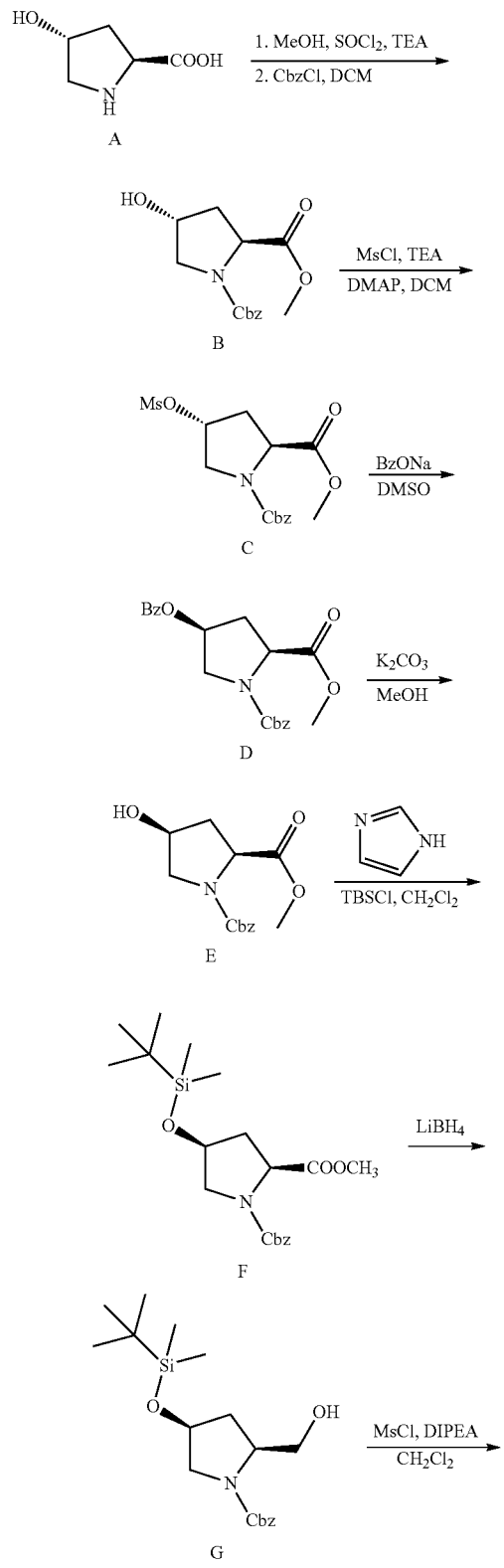
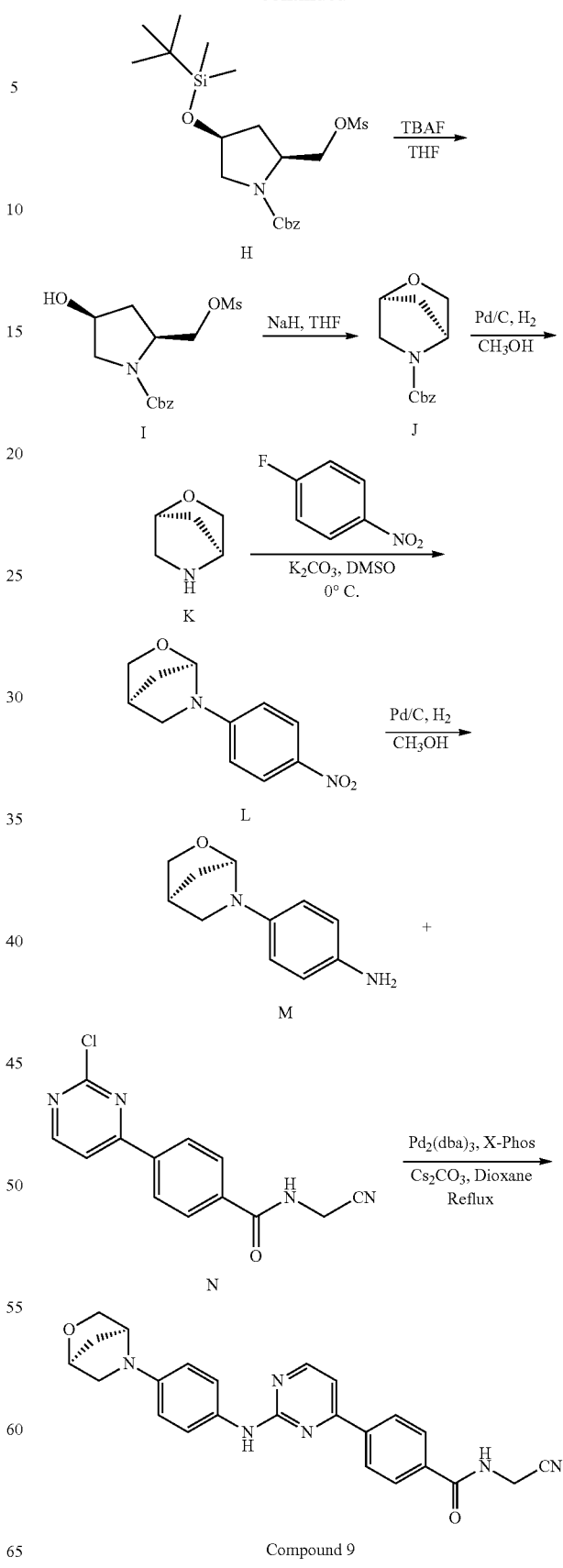
Compound 9

Synthesis of (2S,4R)-1-benzyl 2-methyl 4-hydroxypyrrolidine-1,2-dicarboxylate

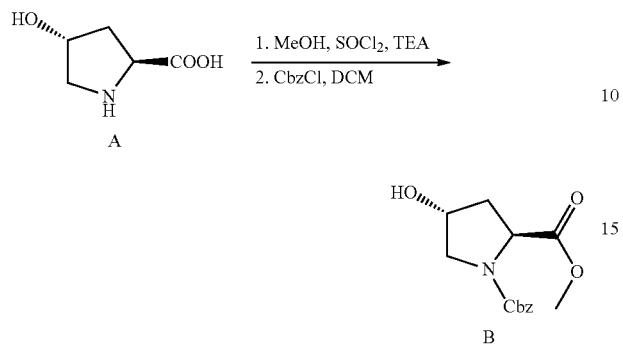

To a solution of A (50 g, 381.6 mmol) in MeOH (350 mL) was added SOCl$_2$ (30 mL) at room temperature. The reaction mixture was stirred for 1 h and then heated to 65° C. overnight. The solvent was evaporated and the residue was dissolved in CH$_2$Cl$_2$ (800 mL). The mixture was cooled to 0° C., TEA (130 mL) was added and then CbzCl (62.2 mL) was added dropwise. After stirring at 0° C. for 30 minutes, the reaction was quenched by pouring into an aqueous solution of citric acid (10%, 800 mL) and the product was extracted with CH$_2$Cl$_2$. The combined organic layers were dried (Na$_2$SO$_4$), filtered and concentrated to give crude product (64 g, 60%) as light yellow oil, which was used in the next step without further purification. LC-MS: 301.8 ([M+Na]$^+$).

Synthesis of (2S,4R)-1-benzyl 2-methyl 4-(methylsulfonyloxy)pyrrolidine-1,2-dicarboxylate

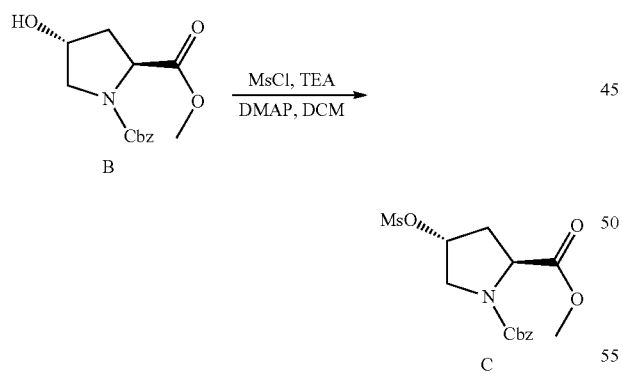

To a solution of B (50 g, 179 mmol) in DCM (1500 mL) was added dropwise TEA (29 mL) at 0° C., followed by MsCl (18.8 mL). A catalytic amount of DMAP (6.8 g) was added and the mixture was stirred at 0° C. for 1 h, then at room temperature for 2 h. The reaction mixture was poured into ice water and the product was extracted with EtOAc. The combined organic layers were washed with 10% aq HCl, 5% aq NaHCO$_3$ and water, dried (Na$_2$SO$_4$), filtered and concentrated to give crude product (65 g, 100%) as colorless oil. LC-MS: 379.8 ([M+Na]$^+$).

Synthesis of (2S,4S)-1-benzyl 2-methyl 4-(benzoyloxy)pyrrolidine-1,2-dicarboxylate

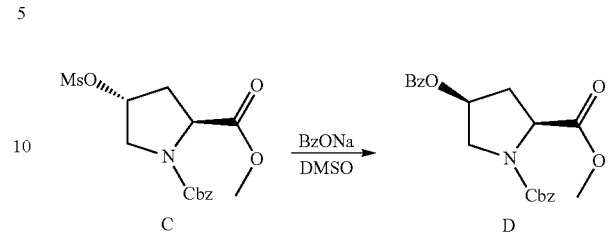

To a solution of C (60.00 g, 0.16 mol) in DMSO (600 mL) was added BzONa (49.00 g, 0.34 mol) at room temperature and the reaction mixture heated at 90° C. overnight. The reaction mixture was poured into water and EtOAc. The organic phase was separated and the aqueous layer was extracted with EtOAc. The combined organic layers were dried (Na$_2$SO$_4$), filtered, concentrated and purified by column chromatography (Pet ether/EtOAc=10:1 to 5:1) to give the product (28 g, 46%) as a white solid. LC-MS: 383.9 ([M+1]$^+$).

Synthesis of (2S,4S)-1-benzyl 2-methyl 4-hydroxypyrrolidine-1,2-dicarboxylate

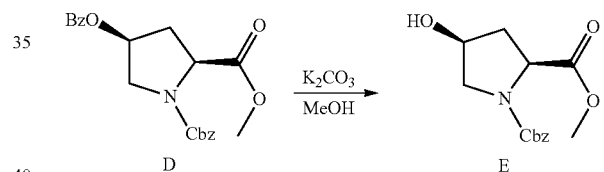

To a solution of D (23 g, 65.8 mmol) in MeOH (100 mL) was added K$_2$CO$_3$ (9.1 g, 65.8 mmol) at 0° C., and the mixture was stirred at room temperature for 1 h. TLC showed the reaction was complete. The mixture was filtered, the filtrate was concentrated in vacuo to remove MeOH, the residue was dissolved in EtOAc, washed with water, brine, dried (MgSO$_4$) filtered and concentrated to give crude product which was purified by chromatography on silica gel (Pet Ether/EtOAc=4/1-1/1) to get the desired product (12.6 g, 70%) as light yellow oil.

Synthesis of (2S,4S)-1-benzyl 2-methyl 4-(tert-butyldimethylsilyloxy)pyrrolidine-1,2-dicarboxylate

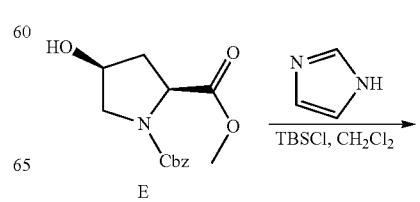

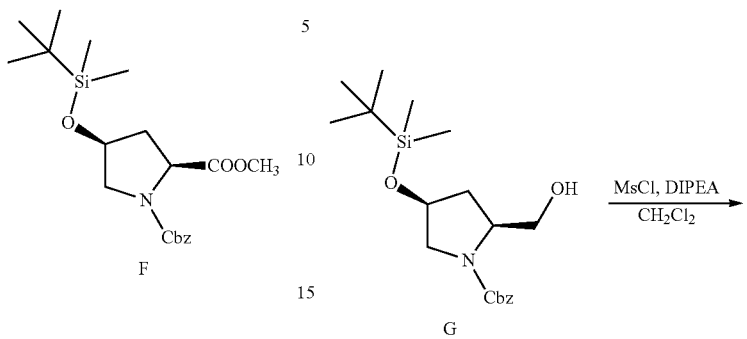

F

To a solution of E (11.50 g, 41 mmol) in $CH_2Cl_2$ (170 mL) was added imidazole (5.60 g, 82 mmol) and TBSCl (11.2 g, 74 mmol). The reaction mixture was stirred at room temperature for 1.5 h. The reaction mixture was poured into water and EtOAc, the organic layer was separated, washed with water, dried ($Na_2SO_4$), filtered and concentrated to give desired product (15.9 g, 99%) as colorless oil.

Synthesis of (2S,4S)-benzyl 4-(tert-butyldimethylsilyloxy)-2-(hydroxymethyl)pyrrolidine-1-carboxylate

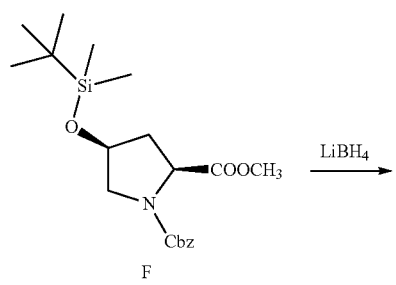

To a solution of F (15.0 g, 38 mmol) in THF (50 mL) was added $LiBH_4$ (1.9 g, 87 mmol) at 0° C., the mixture was warmed to RT and stirred at room temperature for 4 h, TLC showed the reaction was complete and water was added. The product was extracted with EtOAc and the organic layer was washed with brine, dried ($Na_2SO_4$), filtered and concentrated to give crude product (13.2 g, 95%) as colorless oil, which was used directly in the next step.

Synthesis of (2S,4S)-benzyl 4-(tert-butyldimethylsilyloxy)-2-((methylsulfonyloxy)methyl)pyrrolidine-1-carboxylate

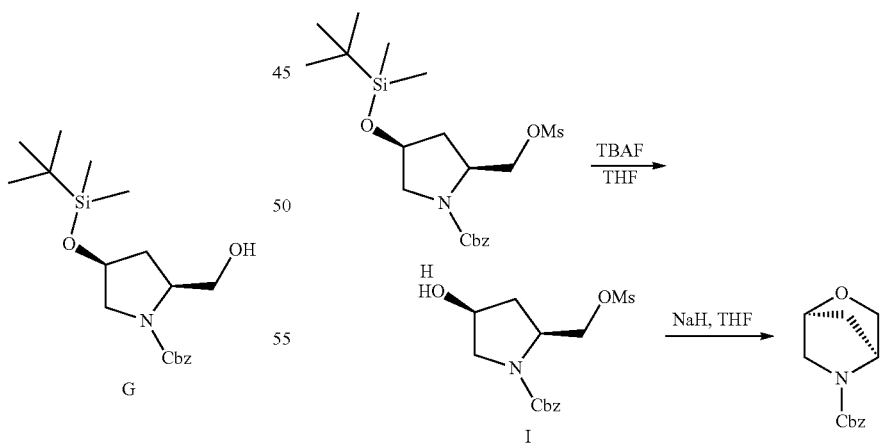

A solution of G (13.0 g, 35.6 mmol) and DIPEA (12.5 mL) in $CH_2Cl_2$ (150 mL) was treated with MsCl (4.2 mL) at 0° C. The reaction mixture was stirred at 0° C. for 15 minutes, then at room temperature for another 30 minutes. The reaction was diluted with $CH_2Cl_2$, washed with water, dried ($Na_2SO_4$), filtered and concentrated to give crude product (16.5 g, 100%) as light yellow oil that was used in the next step without any purification. LC-MS: 465.7 ($[M+Na]^+$).

Synthesis of (1S,4S)-benzyl 2-oxa-5-azabicyclo[2.2.1]heptane-5-carboxylate

A solution of H (15.6 g, 35.2 mmol) in THF (400 mL) was treated with TBAF (30.0 g, 114.7 mmol). The reaction mixture was stirred at room temperature for 30 minutes, then cooled to 0° C. and NaH (1.5 g, 62.5 mmol) was added. Stirring at room temperature was continued for 24 h. The reaction was quenched by pouring the mixture into water and the product was extracted with EtOAc. The organic layer was dried (Na$_2$SO$_4$), filtered and evaporated in vacuo to give crude product purified by flash chromatography (silica gel, pet ether/EtOAc=10:1-3:1) to give the desired product (6.2 g, 76%) as light yellow oil. LC-MS: 255.8 ([M+Na]$^+$).

Synthesis of (1S,4S)-2-oxa-5-aza-bicyclo[2.2.1]heptane

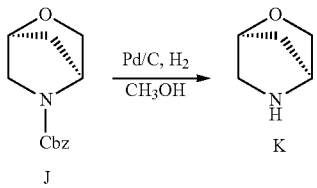

A solution of G (1.80 g, 7.7 mmol) in MeOH (50 mL) was hydrogenated in the presence of Pd/C (10%, 0.9 g) under a H$_2$ atmosphere at 50° C. The reaction mixture was stirred overnight. The mixture was filtered through a pad of Celite and the solvent removed in vacuo to give the crude product (1.3 g, 100%) as oil, which was used directly in the next step without any purification. LC-MS: 99.9 ([M+1]$^+$).

Synthesis of (1S,4S)-2-(4-nitrophenyl)-5-oxa-2-aza-bicyclo[2.2.1]heptane

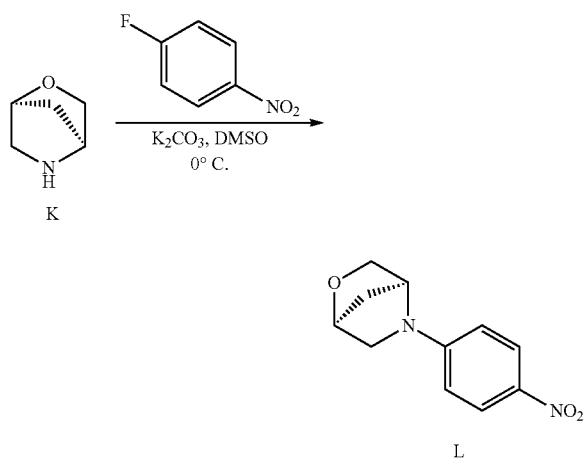

A mixture of K (1.3 g, 13.1 mmol), 1-fluoro-4-nitrobenzene (2.2 g, 15.7 mmol) and K$_2$CO$_3$ (2.16 g, 15.7 mmol) in DMSO (40 mL) was heated at 80° C. for 4 h. The reaction mixture was cooled to RT, water was added and stirred for 10 minutes. The product was extracted with EtOAc and the organic layer washed with water dried (Na$_2$SO$_4$), filtered and evaporated to give crude product that was washed with MTBE to give the desired product (1.2 g, 42%) as a yellow solid. LC-MS: 221 ([M+1]$^+$).

Synthesis of 4-((1S,4S)-2-oxa-5-azabicyclo[2.2.1]heptan-5-yl)aniline

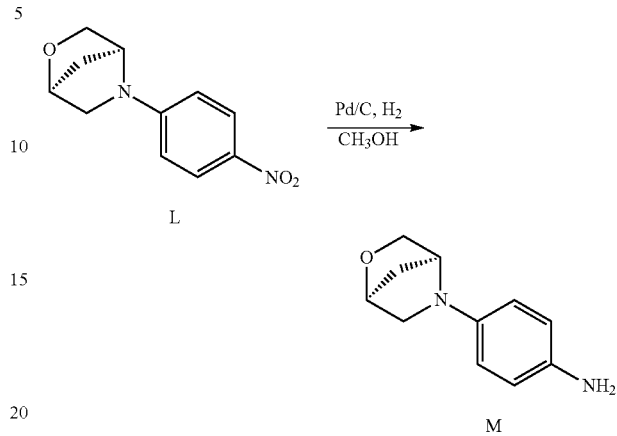

To a solution of L (600 mg, 2.7 mmol) in CH$_3$OH (50 mL) was added Pd/C (60 mg) and the mixture was stirred under a H$_2$ atmosphere at room temperature for 4 h. The mixture was filtered through Celite to remove the catalyst and the filtrate concentrated to give the desired product (500 mg, 96%) as a red solid. LC-MS: 191.0 ([M+1]$^+$).

Synthesis of 4-(2-((4-((1S,4S)-2-oxa-5-azabicyclo[2.2.1]heptan-5-yl)phenyl)amino)pyrimidin-4-yl)-N-(cyanomethyl)benzamide Compound 9

To a solution of M (315 mg, 1.66 mmol) and N (450 mg, 1.66 mmol) in dioxane (50 mL), was added Pd$_2$(dba)$_3$ (150 mg, 0.17 mmol), X-phos (78 mg, 0.16 mmol) and Cs₂CO₃ (1.21 g, 3.7 mmol) at room temperature under N₂. The mixture was heated to reflux and stirred for 5 h. The mixture was cooled to room temperature and filtered through filter paper; the filtrate was partitioned against water (50 mL). The aqueous layer was extracted with EtOAc, the combined organic layers were dried (Na₂SO₄), filtered and evaporated to give crude product which was purified by silica gel (PE/EA=1/1 then CH₂Cl₂/CH₃OH=50/1) to get the desired product (70 mg, 10%) as a yellow solid. LC-MS: 441.2 ([M+1]⁺), ¹H NMR (400 MHz, DMSO) δ 9.39 (s, 1H), 9.36 (t, J=6.0 Hz), 8.51 (d, J=5.1 Hz, 1H), 8.27 (d, J=8.5 Hz, 2H), 8.03 (d, J=8.4 Hz, 2H), 7.59 (d, J=9.0 Hz, 2H), 7.38 (d, J=5.2 Hz, 1H), 6.62 (d, J=8.9 Hz, 2H), 4.60 (s, 1H), 4.51 (s, 1H), 4.36 (d, J=5.3 Hz, 2H), 3.72 (ABq, J=7.0 Hz, Δv=21.2 Hz, 2H), 3.51 (d, J=7.9 Hz, 1H), 2.94 (d, J=9.4 Hz, 1H), 1.95-1.82 (m, 1H).

Example 10

Synthesis of Compound 10

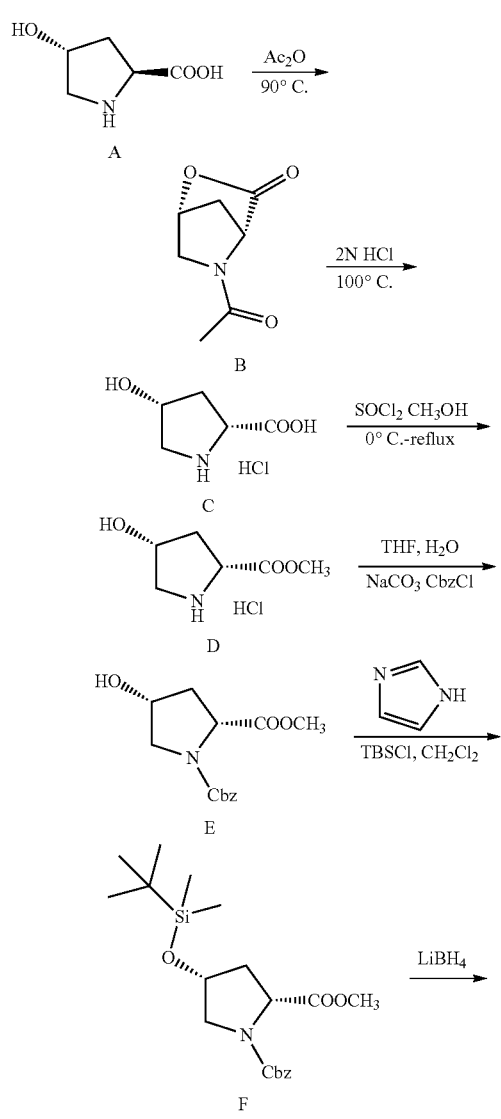

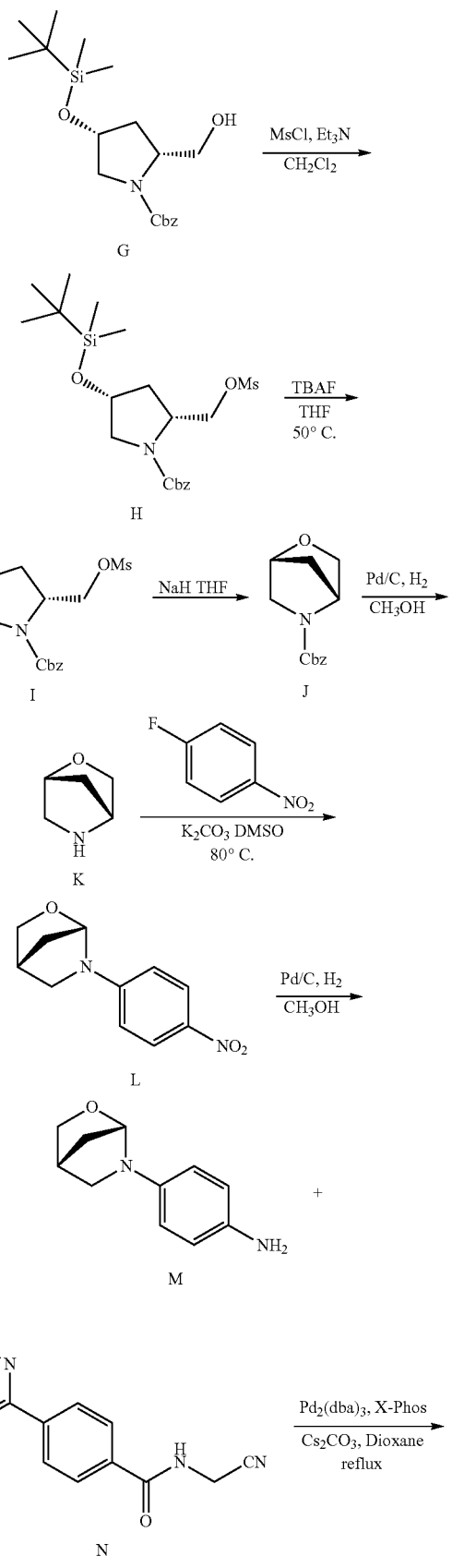

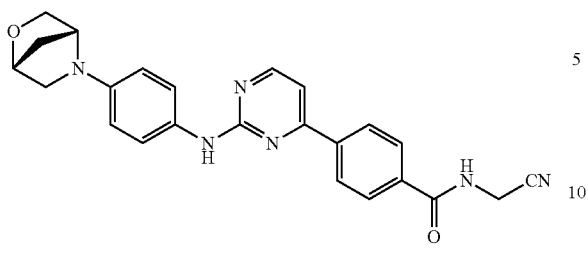

Compound 10

Synthesis of (1R,4R)-5-acetyl-2-oxa-5-azabicyclo[2.2.1]heptan-3-one

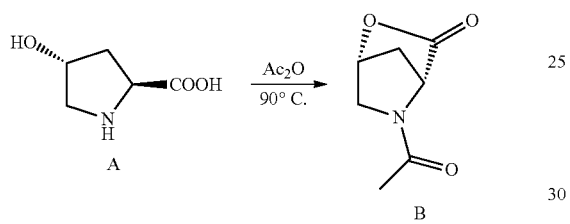

A stirred mixture of A (50 g, 381.6 mmol) and Ac₂O (305 mL) was heated to 90° C. for 16 h under N₂, the solvent was evaporated under reduced pressure, the residue was dissolved in EtOAc and washed with water. The aqueous layer was further extracted with CHCl₃ and the combined organic layers dried (Na₂SO₄), filtered and evaporated. The residue obtained was recrystallized from EtOAc to obtain the product (24 g, 40%) as a white solid.

Synthesis of (2R,4R)-4-hydroxypyrrolidine-2-carboxylic acid hydrochloride

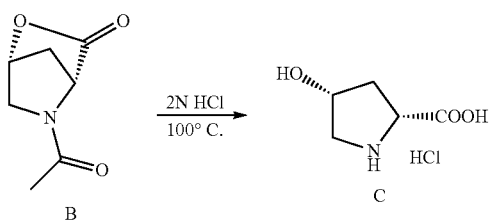

The mixture of B (14 g, 90.3 mmol) in 2N HCl (160 mL) was stirred overnight at 100° C., LCMS showed the reaction was complete, the solvent was removed in vacuo and the residue was recrystallized in EtOAc to give the desired product as a white solid. LC-MS: 205.1 ([M+1]⁺).

Synthesis of (2R,4R)-methyl 4-hydroxypyrrolidine-2-carboxylate hydrochloride

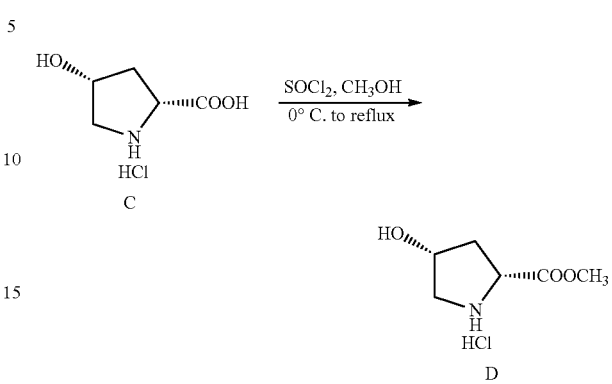

To a solution of A (16.56 g, 98.8 mmol) in CH₃OH (150 mL) was added SOCl₂ (35.26 g, 296.4 mmol) at room temperature and the mixture was heated to reflux for 3 h. The solvent was removed in vacuo and the off-white solid obtained was used in next step without further purification.

Synthesis of (2R,4R)-1-benzyl 2-methyl 4-hydroxypyrrolidine-1,2-dicarboxylate

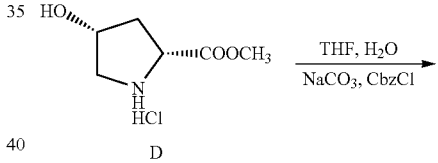

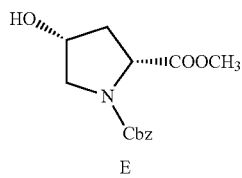

To a solution of D (17.94 g, 98.8 mmol) and Na₂CO₃ (10.5 g, 98.8 mmol) in THF/H₂O (150 mL/50 mL) was added CbzCl (20.2 g, 118.56 mmol) at 0° C. and the mixture was stirred at room temperature for 2 h. The mixture was filtered through filter paper and the filtrate was concentrated. Water (200 mL) was added and the product was extracted with EtOAc (100 mL×3). The combined organic layers were washed with brine, dried (MgSO₄), filtered, and concentrated. The residue was purified by column chromatography (silica gel, Pet Ether/EtOAc=5/1-2/1) to get the desired product (7.4 g, 27%) as a light yellow oil. LC-MS: 279.9 ([M+1]⁺).

Synthesis of (2R,4R)-1-benzyl 2-methyl 4-((tert-butyldimethylsilyl)oxy)pyrrolidine-1,2-dicarboxylate

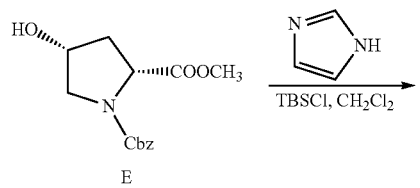

To a solution of E (7.4 g, 26.5 mmol) in dichloromethane (70 mL) was added imidazole (3.6 g, 53 mmol). TBSCl in CH$_2$Cl$_2$ (30 mL) was added to the solution at 0° C. and the reaction mixture was stirred at room temperature overnight. The reaction mixture was washed with water (200 mL), brine (200 mL) and the organic layer dried (MgSO$_4$), filtered and concentrated to get the crude product (10.4 g) as light yellow oil, which was used in the next step without purification. LC-MS: 415.9 ([M+23]$^+$).

Synthesis of (2R,4R)-benzyl 4-(tert-butyldimethylsilyloxy)-2-(hydroxymethyl)pyrrolidine-1-carboxylate

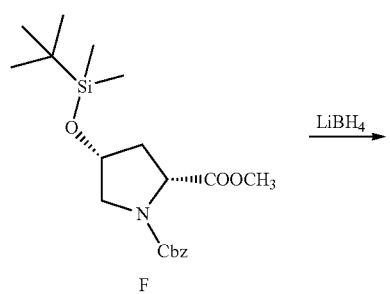

To a solution of F (10.4 g, 26.5 mmol) in anhydrous THF (150 mL) was added LiBH$_4$ (0.92 g, 42.4 mmol) at 0° C., the mixture was stirred at room temperature for 3 h. The reaction was partitioned against H$_2$O (100 mL) and the product was extracted with EtOAc (100 mL×3). The combined organic layers were washed with brine (100 mL), dried (MgSO$_4$), concentrated and the residue obtained purified by silica gel column (pet. ether/EtOAc=100/0-60/10) to get desired product (8.84 g, 91%) as light yellow oil. LC-MS: 365.9 ([M+1]$^+$).

Synthesis of (2R,4R)-benzyl 4-(tert-butyldimethylsilyloxy)-2-((methylsulfonyloxy)methyl)pyrrolidine-1-carboxylate

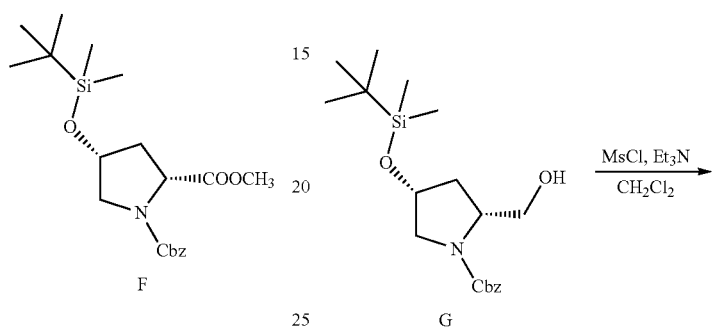

To a solution of G (8.32 g, 22.8 mmol) in CH$_2$Cl$_2$ (200 mL) and Et$_3$N (4.6 g, 45.6 mmol) at 0° C., was added MsCl (3.13 g, 27.3 mmol) and the mixture was stirred at room temperature for 2 h. The reaction was then partitioned against H$_2$O (200 mL), extracted with CH$_2$Cl$_2$ (100 mL×3), and the combined organic layers washed with brine (100 mL), dried (MgSO$_4$), filtered and concentrated to give the crude product (10.11 g, 100%), which was directly used in next step. LC-MS: 443.8 ([M+1]$^+$).

Synthesis of (1R,4R)-benzyl 2-oxa-5-azabicyclo[2.2.1]heptane-5-carboxylate

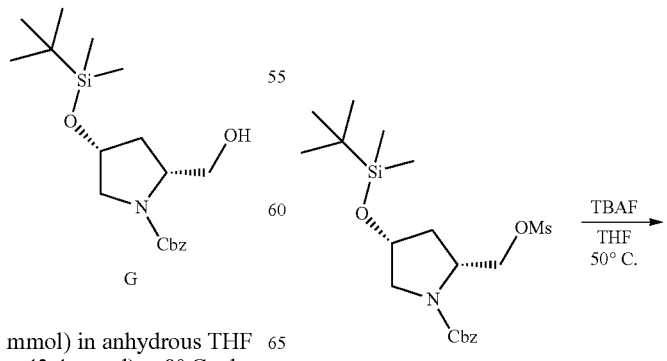

-continued

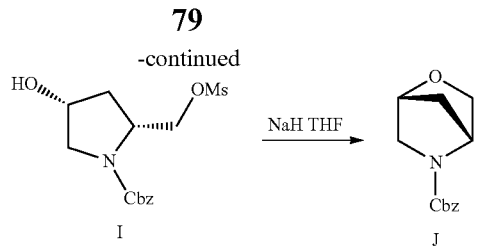

To a solution of H (10.11 g, 22.8 mmol) in THF (200 mL) was added TBAF (23.8 g, 91.2 mmol), and the mixture was heated at 50° C. for 3 h. NaH (1.37 g, 34.2 mmol) was added and the mixture was stirred at room temperature for 2 h. The mixture was concentrated to remove THF, then was diluted with EtOAc and partitioned against water. The aqueous layer was extracted with EA (100 mL×3) and the combined organic layers washed with brine (100 mL), dried (MgSO$_4$), filtered, concentrated and purified by silica gel column (Pet. Ether/EtOAc=10:1 to 5:1) to get the product (4.3 g, 81%) as light yellow oil. LC-MS: 233.9 ([M+1]$^+$).

Synthesis of (1R,4R)-2-oxa-5-azabicyclo[2.2.1]heptane

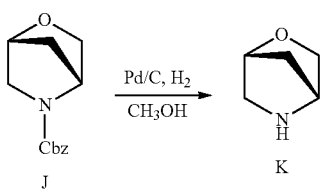

To a solution of J (2 g, 8.6 mmol) in CH$_3$OH (20 mL) was added Pd/C (0.2 g), the mixture was stirred under H$_2$ balloon at 50° C. for 4 h. The catalyst was removed by filtration through a pad of Celite and the filtrate concentrated to get the crude product (1.1 g, 100%) as colorless oil, which was used in next step without purification. LC-MS: 100.5 ([M+1]$^+$).

Synthesis of (1R,4R)-2-oxa-5-azabicyclo[2.2.1]heptane

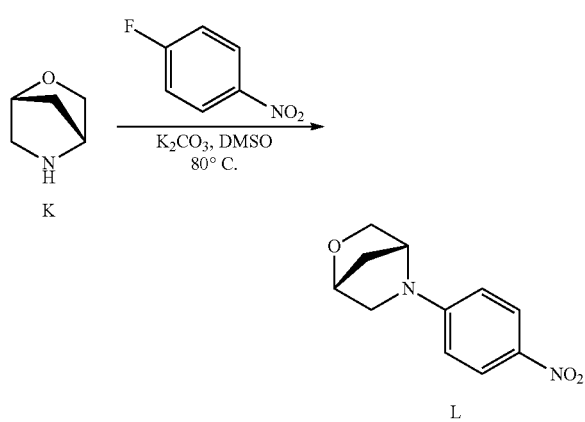

To a solution of K (0.85 g, 8.6 mmol) in DMSO (30 mL) was added 1-fluoro-4-nitrobenzene (1.46 g, 10.32 mmol) and potassium carbonate (1.43 g, 10.32 mmol), the mixture was heated to 80° C. and stirred for 4 h. The mixture was cooled to room temperature, and H$_2$O (50 mL) was added, the mixture was extracted with EA (50 mL×3), and the combined organic layers washed with brine, dried (MgSO$_4$), filtered and concentrated to get a yellow solid, which was washed with 2-methoxy-2-methylpropane (10 mL) to get the product (1.4 g, 74% from J) as a yellow solid. LC-MS: 221 ([M+1]$^+$).

Synthesis of 4-((1R,4R)-2-oxa-5-azabicyclo[2.2.1]heptan-5-yl)aniline

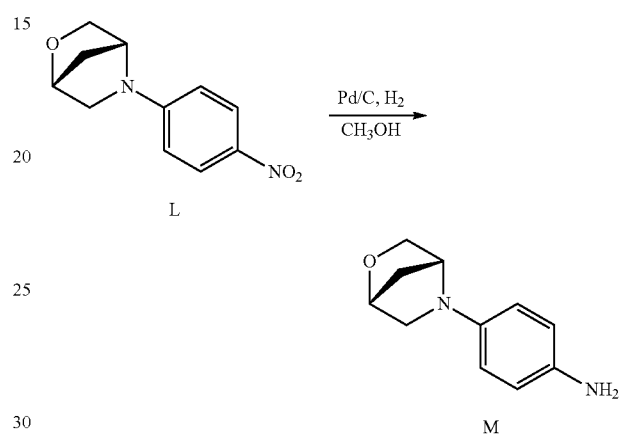

To a solution of L (1.31 g, 6.0 mmol) in CH$_3$OH (30 mL) was added Pd/C (10%, 0.13 g), the mixture was stirred under a H$_2$ atmosphere for 4 h. The catalyst was removed by filtration through a pad of Celite and the filtrate concentrated to get crude product (1.01 g, 88.6%) as a brown solid, it was used in next step without purification. LC-MS: 191.0 ([M+1]$^+$).

Synthesis of 4-(6-((4-((1R,4R)-2-oxa-5-azabicyclo[2.2.1]heptan-5-yl)phenyl)amino)pyrimidin-4-yl)-N-(cyanomethyl)benzamide

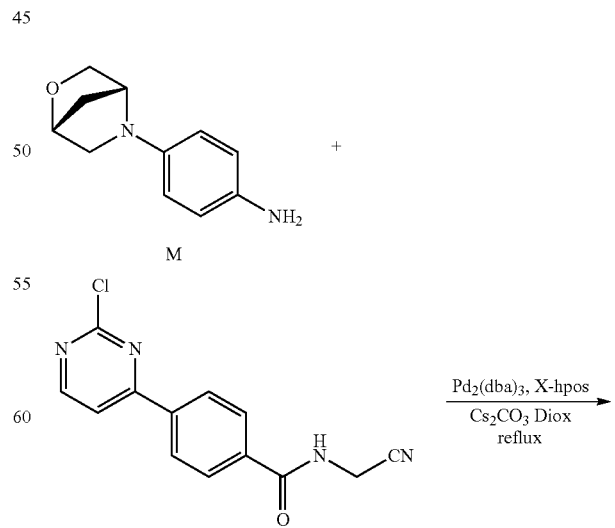

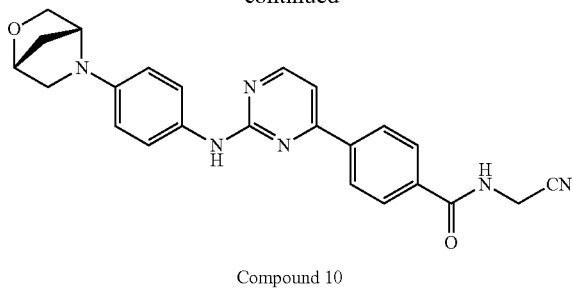

Compound 10

To a solution of M (293 mg, 2.2 mmol) and N (420 mg, 2.2 mmol) in Dioxane (60 mL), was added Pd$_2$(dba)$_3$ (200 mg, 0.22 mmol), X-phos (104 mg, 0.22 mmol) and Cs$_2$CO$_3$ (1.61 g, 4.4 mmol) under N$_2$, the mixture was heated to 100° C. and stirred for 6 h. The reaction was cooled to room temperature, and EA (50 mL) was added. The resultant mixture was filtered through filter paper to remove the solid and the filtrate partitioned against water H$_2$O (100 mL). The aqueous layer was extracted with EA (50 mL×3) and the combined organic layers washed with brine, dried (MgSO$_4$), filtered and concentrated and purified by silica gel column (Pet Ether/EtOAc=1/1-CH$_2$Cl$_2$/CH$_3$OH=50/1) to get the desired product (123 mg, 13.1%) as a yellow solid. LC-MS: 441.2 ([M+1]$^+$)

1H-NMR (400 MHz, DMSO-d$_6$) δ 9.37 (s, 1H), 9.34 (t, J=5.2 Hz, 1H), 8.50 (d, J=5.2 Hz, 1H), 8.25 (d, J=8.4 Hz, 2H), 8.01 (d, J=8.4 Hz, 2H), 7.57 (d, J=8.8 Hz, 1H), 7.36 (d, J=5.2 Hz, 2H), 6.61 (d, J=8.8 Hz, 2H), 4.58 (s, 1H), 4.49 (s, 1H), 4.35 (d, J=5.2 Hz, 2H), 3.70 (Abq, J=7.2 Hz, Δv=22 Hz, 2H), 3.49 (dd, J1=1.2 Hz, J2=9.2 Hz, 1H), 2.92 (d, J=9.6 Hz, 1H), 1.93-1.80 (m, 2H).

Example 11

Synthesis of Compound 11

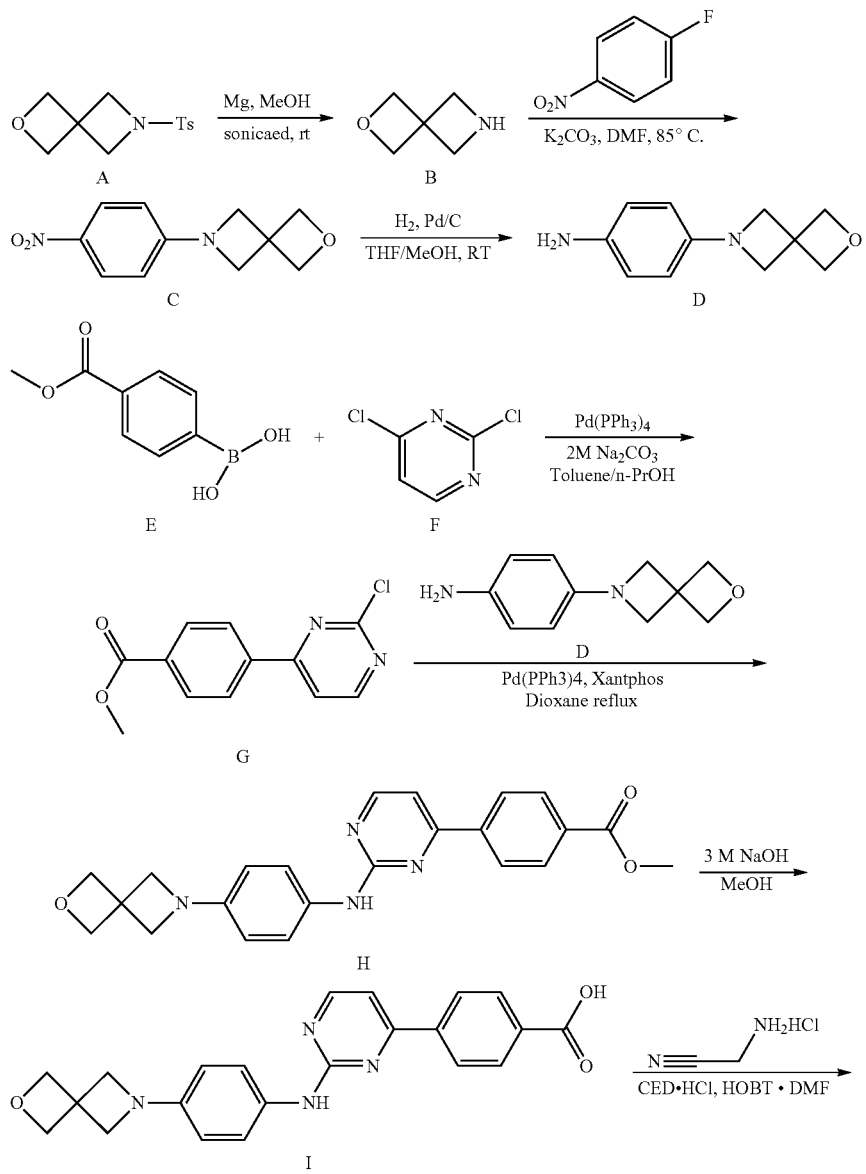

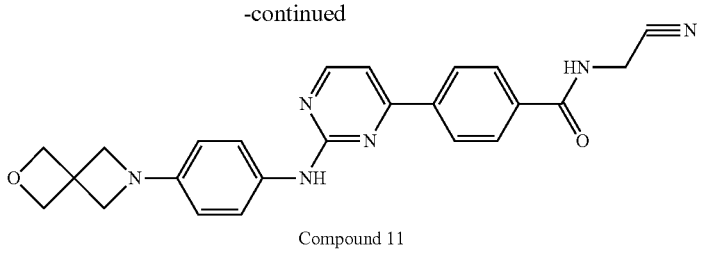

Compound 11

Synthesis of B

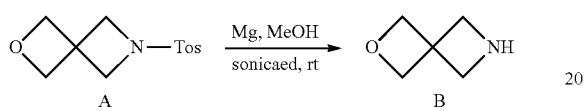

Mg (4.84 g, 0.20 mol) was added to a mixture of compound A (7.3 g, 28.8 mmol) in MeOH (500 mL) and was sonicated for 1 h. Almost all solvent was removed under reduce pressure from the grey reaction mixture to give a viscous grey residue which was diluted with ether (500 mL) and stirred for 1 h. Sodium sulfate decahydrate (15.00 g) was added and the resulting light grey mixture stirred vigorously for 30 mins. The solids were removed by filtration and the filter cake washed with ether, the filtrate was concentrated to give an oil (1.50 g, 53%). It was used for the next step without further purification.

TLC: $R_f$=0.02 (silica gel, ethyl acetate:pet ether=1:1, v/v)

Synthesis of C

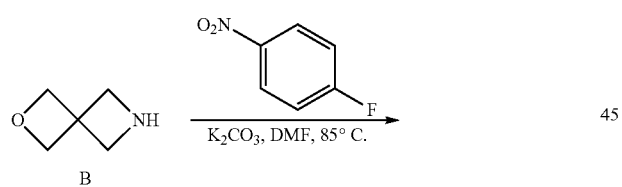

A solution of B (1.5 g, 15.1 mmol), 1-fluoro-4-nitrobenzene (2.10 g, 15.1 mmol) and $K_2CO_3$ (2.50 g, 18 mmol) in dry THF (30 mL) was heated to reflux for 2 h. TLC showed 1-fluoro-4-nitrobenzene was completely consumed. The reaction mixture was allowed to cool to rt and concentrated under reduce pressure. The residue was poured into water and extracted with DCM (3*50 mL). The organic layers were combined and washed with brine, dried over anhydrous $Na_2SO_4$, filtered and concentrated. The residue obtained was purified by flash column chromatography (pet. ether/EtOAc, 50/1 to 10/1, v/v) to give a yellow solid (1.15 g, 36%). The structure was confirmed by H-NMR spectra.

TLC: $R_f$=0.2 (silica gel, ethyl acetate: pet ether=1:5, v/v)

$^1$H-NMR (400 MHz, CDCl$_3$) δ (ppm): 8.11 (d, J=9.2 Hz, 2H), 6.32 (d, J=9.2 Hz, 2H), 4.89 (s, 4H), 4.22 (s, 4H).

Synthesis of D

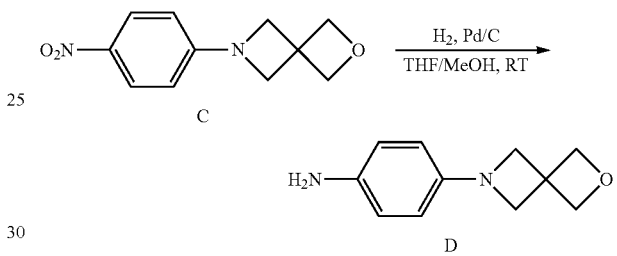

A solution of C (1.50 g, 6.8 mmol) and 10% Pd/C (90 mg) in a mixture of MeOH (20 mL) and THF (20 mL) was placed under a H$_2$ atmosphere and stirred at room temperature overnight. TLC showed the compound of C was completely consumed. The catalyst was removed by filtration through celite and the filter cake washed with MeOH. The filtrate was concentrated under reduce pressure and the residue obtained purified by chromatography to give a yellow solid (1.05 g, 81%). The structure was confirmed by H-NMR spectra.

TLC: $R_f$=0.2 (silica gel, ethyl acetate: pet ether=1:2, v/v)

$^1$H-NMR (400 MHz, CDCl$_3$) δ (ppm): 6.65 (d, J=8.4 Hz, 2H), 6.36 (d, J=8.4 Hz, 2H), 4.83 (s, 4H), 3.93 (s, 4H).

Synthesis of G

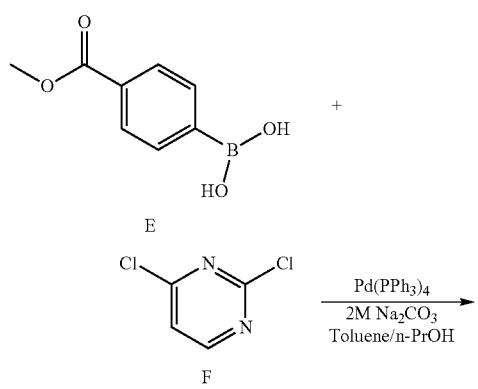

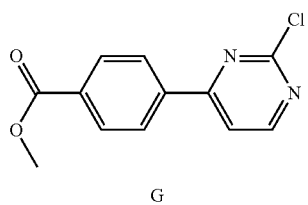

To a mixture of E (1.00 g, 5.55 mmol) and F (1.65 g, 11.11 mmol) in a mixture of toluene (20 mL), n-PrOH (6.5 mL) and 2M Na$_2$CO$_3$ (5 mL) was added Pd(PPh$_3$)$_4$ (0.65 g, 0.056 mmol). The reaction was stirred under nitrogen and heated to reflux for 24 hours. TLC showed the compound of E was consumed completely. The reaction was cooled to rt and poured into a mixture of H2O and EtOAc. This mixture was filtered through celite and washed with EtOAc. The aqueous layer was extracted with EtOAc (50 mL*3) and the combined organic layers washed with brine, dried over anhydrous Na$_2$SO$_4$, filtered and concentrated. The residue obtained was purified by column chromatography (DCM/MeOH, 100:0 to 98:2, v/v) to give the product as a white solid (800 mg, 61%). The structure was confirmed by LC-MS spectra.

TLC: R$_f$=0.5 (silica gel, pet ether/ethyl acetate=10/1, v/v)
LC-MS: [M+1]$^+$: 249.1/251.1=3/1

Synthesis of H

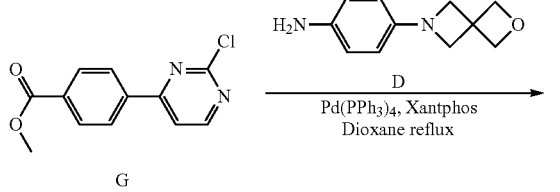

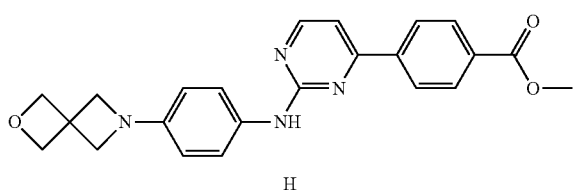

To a stirred mixture of G (800 mg, 3.23 mmol, D (675 mg, 3.23 mmol) and Cs$_2$CO$_3$ (2.09 g, 6.42 mmol) in dioxane (30 mL) was added Xantphos (186 mg, 0.32 mmol) and Pd(PPh$_3$)$_4$ (372 mg, 0.32 mmol). The reaction was heated to reflux for 16 hs. TLC showed compound E was consumed completely. The reaction was cooled to rt and poured into a mixture of H2O and EtOAc. This mixture was filtered through celite and washed with EtOAc. The aqueous layer was extracted with EtOAc (50 mL*3) and the combined organic layers washed with brine, dried over anhydrous Na$_2$SO$_4$, filtered and concentrated. The residue obtained was purified by column chromatography (DCM:MeOH=100:1/50:1) to give a viscous compound (680 mg, 52%) The structure was confirmed by LC-MS spectra and LC-MS showed it contained a little impurity. It was used for the next step without further purification.

TLC: R$_f$=0.5 (silica gel, pet ether/ethyl acetate=1/1, v/v)
LC-MS: [M+1]$^+$: 403.0

Synthesis of H

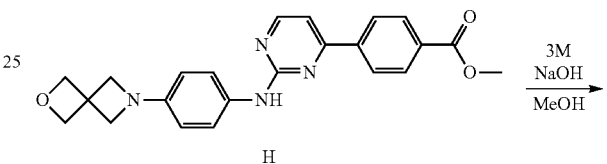

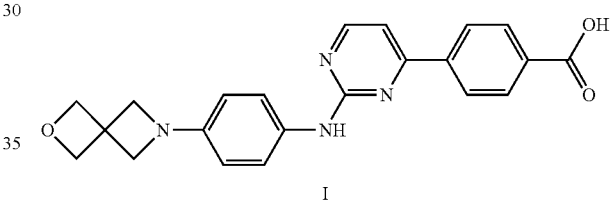

A solution of H (650 g, 1.61 mmol) in MeOH (8 mL) and 3 M NaOH (8 mL) was heated at 70° C. for 2 h. TLC showed compound of H was consumed completely. The organic solvent was removed in vacuo and the aqueous solution that remained poured into water and extracted with EtOAc. The organic layer was discarded and the pH of the remaining aqueous solution adjusted to PH=5 with 2N HCl (aq). The mixture was stirred at room temperature for 30 min. The precipitate that formed was collected by filtration washed with water and dried in vacuo to give a gray solid (230 mg, 37%). The structure was confirmed by LC-MS spectra.

TLC: R$_f$=0.4 (silica gel=DCM/MeOH=15/1, v/v)
LC-MS: [M+1]$^+$: 389.0

Synthesis of Compound 11

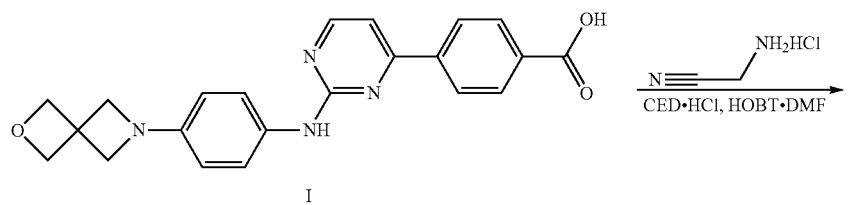

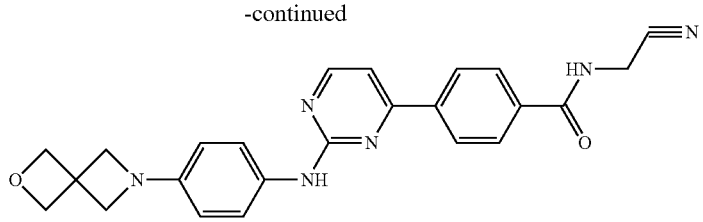

Compound 11

To a solution of I (220 mg, 0.57 mmol) and 2-aminoacetonitrile hydrochloride (104 mg, 1.13 mmol) in DMF (5 mL) were added TEA (434 mg, 3.39 mmol) HOBT (91 mg, 0.68 mmol) and EDC.HCl (239 mg, 1.24 mmol). The reaction mixture was stirred and heated to 100° C. for 2 h. TLC showed most of I were consumed and the reaction was cooled to rt. The reaction mixture was poured into water (10 mL) and extracted with DCM (3*20 mL). The organic layers were combined, washed with brine, dried over anhydrous $Na_2SO_4$, filtered and concentrated. The residue obtained was purified by column chromatography (DCM:MeOH=100:1/50:1) to give a yellow solid (123 mg, 51% yield). The structure was confirmed by LC-MS and H-NMR spectra.

TLC: $R_f$=0.5 (silica gel, MeOH/$CH_2Cl_2$=1/15 v/v)

LC-MS: $[M+1]^+$:427

$^1$H-NMR (400 MHz, $d_6$-DMSO) δ (ppm): 9.41 (s, 1H), 9.35 (t, J=5.2 Hz, 1H), 8.51 (d, J=5.2 Hz, 1H), 8.26 (d, J=8.4 Hz, 2H), 8.02 (d, J=8.8 Hz, 2H), 7.58 (d, J=8.8 Hz, 2H), 7.38 (d, J=4.8 Hz, 1H) 6.44 (d, J=8.8 Hz, 2H), 4.73 (s, 4H), 4.36 (d, J=5.2 Hz, 2H), 3.94 (s, 4H).

Compound Analysis $^1$H and $^{13}$C NMR data were acquired on a Brucker AV-300 AVANCE NMR spectrometer.

LC-EI-MS and EI-MS

General Parameters:

LC-EI-MS and EI-MS data were acquired on a Waters 2795 Alliance HPLC coupled to a Waters 2996 Photodiode Array Detector and Integrity TMD Electron Impact Mass Spectrometer operating under control of Waters Millenium$^{32}$ software version 4.0 with the settings outlined below.

Mass Spectrometer Parameters:

Helium flow of approximately 0.36 L/min.; acquisition mode set to scan; sampling rate of 1 spectra/sec; source temperature 200° C.; nebuliser temperature 80° C.; expansion region temperature 75° C.; mass range m/z 100-550, m/z 100-650 or m/z 100-700 as required.

HPLC Parameters

LC-MS parameters were as described for each of the methods outlined below. ELMS samples were injected and analysed with no column present, with a solvent flow rate of 0.25 mL/min.

Method A1 (LC-EI-MS)

Solvent Gradient:

| Time | % MilliQ water | % ACN | % (0.5% aq formic acid) | Curve |
|---|---|---|---|---|
| 0 | 90 | 0 | 10 | — |
| 0.5 | 90 | 0 | 10 | 6 |
| 7.5 | 0 | 90 | 10 | 6 |
| 10.5 | 0 | 90 | 10 | 6 |
| 11.5 | 90 | 0 | 10 | 6 |
| 14.5 | 90 | 0 | 10 | 6 |

Flow rate: 0.25 mL/min.

Column: one of
Alltima HP $C_{18}$ 2.1×150 mm, 5 micron
XTerra MS $C_{18}$, 3.0×100 mm, 3.5 micron
XBridge $C_{18}$, 3.0×100 mm, 3.5 micron Method A2 (LC-EI-MS)

Solvent Gradient:

| Time | % MilliQ water | % ACN | Curve |
|---|---|---|---|
| 0 | 90 | 10 | — |
| 7 | 0 | 100 | 6 |
| 9 | 0 | 100 | 6 |
| 10 | 90 | 10 | 6 |
| 13 | 90 | 10 | 6 |

Flow rate: 0.25 mL/min

Column: one of
Alltima HP $C_{18}$ 2.1×150 mm, 5 micron
XTerra MS $C_{18}$, 3.0×100 mm, 3.5 micron
XBridge $C_{18}$, 3.0×100 mm, 3.5 micron

LC-ESI-MS

General Parameters:

LC-ESI-MS data was acquired on a Waters 2695Xe HPLC coupled to a Waters 2996 Photodiode Array Detector and Waters ZQ Mass Spectrometer operating under electrospray ionization conditions with Masslynx software version 4.1 with the settings outlined below.

Mass Spectrometer Parameters:

Mass range: m/z 100-650
Scan time: 0.5
Inter scan delay: 0.1
Desolvation gas: 500 L/h $N_2$
Cone Gas: 100 L/h $N_2$
Desolvation Temperature: 400° C.
Source Temperature: 120° C.
Cone Voltage: +30 V for ESI positive mode, or −45 V for ESI negative mode HPLC Parameters:

Were one of the following sets of conditions outlined below.

Method B

Solvent Gradient:

| Time | % MilliQ water | % ACN | Curve |
|---|---|---|---|
| 0 | 90 | 10 | 1 |
| 5 | 0 | 100 | 6 |
| 6 | 0 | 100 | 6 |
| 7 | 90 | 10 | 6 |
| 10 | 90 | 10 | 6 |

Flow rate: 0.25 mL/min.

Column: XTerra MS $C_{18}$, 2.1×50 mm, 3.5 micron

Method C
Solvent Gradient:

| Time | % MilliQ water | % ACN | % 0.5% formic acid$_{(aq)}$ | Curve |
|---|---|---|---|---|
| 0 | 90 | 0 | 10 | 1 |
| 0.5 | 90 | 0 | 10 | 1 |
| 5.5 | 0 | 90 | 10 | 1 |
| 7.5 | 0 | 90 | 10 | 6 |
| 8.5 | 90 | 0 | 10 | 6 |
| 11.5 | 90 | 0 | 10 | 6 |

Flow rate: 0.25 mL/min.
Column: XTerra MS $C_{18}$, 2.1×50 mm, 3.5 micron
Method D
Solvent Gradient:

| Time | % MilliQ water | % ACN | Curve |
|---|---|---|---|
| 0 | 90 | 10 | 1 |
| 10 | 0 | 100 | 6 |
| 12 | 0 | 100 | 6 |
| 13 | 90 | 10 | 6 |
| 16 | 90 | 10 | 6 |

Flow rate: 0.25 mL/min.
Column: XTerra MS $C_{18}$, 3.0×100 mm, 3.5 micron

Example 12

Enzyme Screening

Assay Protocol
Kinase assays were performed based on the method reported by Anastassiadis, T; et al Nature Biotechnology (2011); 29 (11); p 1039-p 1045 (doi:10.1038/nbt.2017).
Results
The IC50 data is shown in Table 2.

TABLE 2

| Compound | JAK1 | | JAK2 | | JAK3 | | TYK2 | |
|---|---|---|---|---|---|---|---|---|
| No | Data 1 | Data 2 | Data 1 | Data 2 | Data 1 | Data 2 | Data 1 | Data 2 |
| 1 | 224.50 | 215.20 | 108.00 | 102.60 | 213.40 | 194.00 | 38.01 | 34.98 |
| 2 | 30.64 | 37.92 | 22.20 | 24.48 | 41.79 | 44.80 | 5.09 | 5.65 |
| 3 | 32.27 | 41.68 | 47.01 | 44.99 | 80.06 | 82.42 | 6.83 | 7.30 |
| 4 | 28.83 | 28.57 | 29.35 | 29.08 | 92.29 | 80.80 | 5.22 | 6.17 |
| 5 | 10.09 | 10.18 | 30.04 | 25.95 | 60.92 | 56.31 | 0.69 | 0.91 |
| 6 | 17.53 | 19.76 | 14.22 | 14.05 | 33.41 | 32.70 | 2.94 | 2.14 |
| 7 | 31.54 | 29.18 | 30.31 | 34.03 | 60.88 | 50.75 | 4.87 | 4.29 |
| 8 | 56.90 | 35.72 | 43.54 | 46.40 | 79.32 | 78.46 | 9.98 | 9.98 |
| 9 | 22.37 | 21.68 | 11.05 | 13.44 | 12.83 | 14.00 | 8.07 | 7.40 |
| 10 | 16.03 | 15.94 | 16.98 | 16.76 | 22.06 | 27.01 | 4.31 | 2.58 |
| 11 | 32.83 | 47.37 | 10.55 | 10.76 | 33.76 | 26.25 | 9.47 | 8.54 |

The compounds of greatest interest are compounds 5, 6 and 9.

Example 13

Cellular Screening

The cellular assay principle is based on the method reported by Daley & Baltimore (Daley and Baltimore; Proc. Natl. Acad. Sci. USA. 1988; 85(23):9312-6). In this cell-based assay, IL3-dependent Ba/F3 cells are transformed by transfection of an human recombinant kinase gene and in turn the modified cells are dependent on the activity of the recombinant kinase for survival and proliferation. The effects test compounds have on proliferation are assessed using conventional readouts such as Alamar Blue and MTT assays of metabolic turnover.

Example 14

Fluorescence Activated Cell Sorter (FACS)

Multiparameter Intracellular Flow Cytometric Analysis of STAT 5 Phosphorylation.
The human erythroleukaemic cell line, HEL 92.1.7 (ATCC, TIB-180), is grown in RPMI 1640 containing 10% FCS supplemented with 1 mM sodium pyruvate. For phosphor-STAT 5 determination, HEL cells are grown in RPMI 1640+1% FCS for 18 hours at 37° C. and $2 \times 10^5$ cells per assay point are exposed to DMSO/test compounds for 2 hours at 37° C. The cells are centrifuged at 1300 rpm for 3 minutes and fixed in paraformaldehyde (2% final concentration) for 15 minutes at 37° C. After centrifugation, cells are permeabilized in 90% methanol at 4° C. for 30 minutes. Following three washes in PBS-2% FCS, the staining is performed as follows using BD PharMingen phycoerythrin-conjugated mouse immunoglobulin isotype control (Cat. No. 551436 and phycoerythrin-conjugated mouse $IgG_1$ antibody to STAT 5 (Y694) (Cat. No. 612567).
Staining proceeds for 1 hour at room temperature in the dark, followed by 3 washes in PBS-2% FCS. The cells are next resuspended in 800 μL PBS-FCS for FACS analysis. Flow cytometry is performed using a Beckman Cell Lab Quanta SC System with 3 colour and side scatter capabilities. Data analysis is performed with CXP analysis software (version 2.2). The median fluorescence intensity (MFI) is used to determine fold change upon treatment of cells with specific inhibitor compounds, calculated as the $MFI_{stimulated}/MFI_{unstimulated}$ ratio for the phosphospecific antibody fluorescence channel (FL2).

Example 15

Western Blots

Experiment 1
Methodology
The murine pro-B cell line BaF3 is routinely maintained in RPMI 1640 media containing 10% FCS. On the day of the experiment, cells are washed twice in PBS, and resuspended in RPMI 1640 media containing 0.1% FCS. After 2 hours of serum deprivation, cells are treated with the desired concentration of Compound 3, Control Compound, or vehicle alone (DMSO) for a further 2 hours. Mouse IL-3 is then added to cells at a final concentration of 5 ng/ml for 15 minutes. Cells are then placed on ice and washed twice in ice-cold PBS. Washed cell pellets are snap-frozen in liquid nitrogen and stored at −80° C.

Cell pellets are lysed on ice in RIPA buffer, and lysates clarified by centrifugation (20,000×g, 4° C., 5 min). The protein concentration of lysates is determined by the Bradford method, and equal amounts of protein (601.1 g/lane) are separated by SDS-PAGE. Protein is then transferred to PVDF, and Western blotting performed using an antibody that specifically recognizes STAT5 phosphorylated at tyrosine 694. The membrane is then stripped and reprobed with an antibody that recognizes total STAT5 protein.

Experiment 2

Methodology

The human erythroleukaemic cell line HEL 92.1.7 is routinely maintained in RPMI 1640 media containing 10% FCS. The day before the experiment, cells are washed twice in PBS, resuspended in RPMI 1640 media containing 1% FCS, and cultured overnight.

The following day, cells are treated with the desired concentration of Compound 3, Control Compound, or vehicle alone (DMSO) for 2 hours. Cells are then placed on ice and washed twice in ice-cold PBS. Washed cell pellets are snap-frozen in liquid nitrogen and stored at −80° C.

Cell pellets are lysed on ice in RIPA buffer, and lysates clarified by centrifugation (20,000×g, 4° C., 5 min). The protein concentration of lysates is determined by the Bradford method, and equal amounts of protein (601.1 g/lane) are separated by SDS-PAGE. Protein is then transferred to PVDF, and Western blotting performed using an antibody that specifically recognizes STAT5 phosphorylated at tyrosine 694. The membrane was then stripped and reprobed with an antibody that recognizes total STAT5 protein.

Example 16

Additional Compound Evaluation

The compounds can also be tested in a murine model of JAK2$^{V617F}$-positive myeloproliferative disease (MPD)

Establishment of JAK2$^{V617F}$-Positive MPD

Bone marrow from male 5-Fluorouracil-treated Balb/c mice could be infected with a JAK2-V617F-GFP retrovirus and retroorbitally injected into lethally irradiated female recipients. From day 21 on the mice could be monitored by daily inspection and twice weekly blood counts+FACS for GFP-positive cells. It would be expected that a rise in hematocrit could occur around day 28 and a rise of the white blood cell count around day 40.

Treatment with Compounds

Early Intervention Group:

Treatment would start on day 21 with compound or carrier given per oral gavage (12 mice in each group). Mice could be monitored by daily inspection and twice weekly blood counts+FACS for GFP-positive cells. Animals would be sacrificed on day 60 8-12 h after the last drug dose. Moribund mice or mice with a white cell count over 200,000/nl or weight loss>20% could be sacrificed earlier.

Late Intervention Group:

Groups of 3 mice could be sacrificed on day 29, 36, 43, 50 and 57 and bone marrow and spleen could be analyzed for reticulin fibrosis. Treatment could start with compound or carrier given per oral gavage as soon as fibrosis is documented in 3/3 mice. Mice could be monitored by daily inspection and twice weekly blood counts+FACS for GFP-positive cells. Animals could be sacrificed after 30 days of therapy 8-12 h after the last drug dose. Moribund mice or mice with a white cell count over 200,000/nl or weight loss>20% could be sacrificed earlier. Animals could be subjected to necropsy.

Analysis of Tissues and Survival

Liver and spleen weights could be determined. Tissue sections from bone marrow, liver and spleen could be analyzed by HE stain. Marrow and spleens could also be silver-stained to assess reticulin fibrosis. Spleen and marrow cells could be analyzed by FACS for GFP, lineage markers, JAK2 and STAT5 phosphorylation. Blood could be collected by heart puncture and plasma separated and frozen for drug concentration measurement. Survival between groups could be compared with the Kaplan-Meyer method.

Assessment of the Activity of JAK2 Inhibitors in Colony-Forming Assays of Human Hematopoietic Cells Peripheral blood mononuclear cells from patients with MPD (predominantly myelofibrosis) with and without JAK2$^{V617F}$ mutation (N=10 for each) and 5 normal controls (commercial supplier) could be isolated by density gradient centrifugation (Ficoll). CD34+ cells can be selected using commercial kits to enrich for progenitor cells. CD34+ cells can be plated in triplicate in methylcellulose supplemented with fetal bovine serum and cytokines (+/−EPO). After incubation of the plates for 2 weeks erythroid and myeloid colony formation could be assessed under an inverted microscope.

Cancer

The effect of the compounds on tumor initiation, progression and metastasis can be evaluated in relevant in vivo animal efficacy models. Models could be human tumor xenografts models in immuno-deficient mice, from human tumor cell lines or preferably from primary or metastatic human tumors. Other models might be human tumor xenografts grown in orthotopic sites, models of disseminated disease and transgenic or labeled tumors models. Models could also include surgical resection of primary tumor and evaluation of metastatic disease.

Models could be selected to ensure that the molecular drug targeted is expressed. Examples of tumors displaying deregulation of the JAK/STAT pathway include prostate carcinoma, breast cancer, colon carcinoma, including leukemia, lymphoma, myeloma, ovarian tumors, melanoma, lung carcinoma, glioma, renal-cell tumors.

Efficacy can be measured in these models by various outcomes depending on tumor type (solid, leukemia or metastatic) and might include measure of tumor onset, tumor growth rate, tumor burden, tumor growth delay, tumor cell kill, incidence of metastasis, imaging of tumor and invasiveness/metastasis by various approaches including labeled cells or reagents, survival, angiogenesis, histopathology. The in vivo animal efficacy models might also be used for determination of the additivity or synergy of the effect of the compounds in combination with other drugs, Asthma is restricted to human species, but animal models are often used to investigate particular aspects of this human disease. Bronchial biopsies and bronchoalveolar lavage (BAL) fluid recovered from patients with asthma have been shown to contain an increased number of activated T cells, B cells, eosinophils and mast cells. Many patients with asthma are sensitized and have specific immunoglobulin E (IgE) antibodies to one or more inhalant allergens. Atopy is, considered to be a major cause of asthma. In atopic individuals, inhalation of allergens preferentially induces a T-helper 2 cell (Th2) response. In the majority of current models, mice are sensitized by itraperitoneal (ip) injection of ovalbumin (OVA), often together with a Th2 skewed adjuvant, such as alum. In the classical mouse model for asthma, C57/BL6 mice are actively sensitized on day 0 by ip injection of 10 µg of OVA absorbed onto 1 mg of alum. From day 14-21 the mice are exposed daily to aerosolized OVA over a 30 minute period. On day 22, airway inflammation is apparent. BAL fluid recovered from these animals demonstrate an increase in peri-bronchiolar space consisting of mixed cellular infiltrates of mononuclear cells and eosinophils. OVA-specific IgE antibodies can be demonstrated in the serum of sensitized animals. The mononuclear cell population consists mainly of cells of Th2 phenotype secreting cytokines IL-4 and IL-5. IL-4 promotes isotype switching of B cells towards IgE synthesis and IL-5 influences the production, maturation and activation of eosinophils.

Rheumatoid arthritis (RA) is a chronic, destrictive inflammatory polyarticular joint disease characterized by passive synovial proliferation and subintimal infiltration of inflammatory cells. Although the aetiology remains to be elucidated, it is generally acknowledged that RA is an autoimmune disease and arthritis is a consequence of loss of tolerance against a cartilage specific autoantigen. In this context, animal models have been established that evolves around induction of RA by an autoantigen such as 1. type II collagen-induced arthris (CIA) and 2. a combination of an antigen from gram-ve bacteria (LPS) with a panel of 4 monoclonal antibodies (mAb). A third model of arthritis is the Adjuvant-induced arthritis (AIA) which is performed mainly in rats. The underlying mechanism of AIA is still controversial. However, a 65 kD myobacterial heat shock protein was shown to share a nonapeptide sequence in the core protein molecule of proteoglycan, and suggests that AIA is also a disease inducible by autologous antigen.

In AIA, eight-week old Lewis rats are given Complete Freund's Adjuvant (CFA) prepared by suspending as an emulsion of heat-killed Mycobacterium butyricum in liquid paraffin at 12 mg/ml. CFA-induced arthritis can be stimulated by injection of 50 µl of CFA emulsion intradermally either in to the footpad or to the base of the tail. From day 7 (onset of arthritis), rats are examined daily for clinical arthritic score on a 0-4 scale: 0, normal; 1, minimal swelling; 2, medium swelling; 3, severe swelling; and 4, sever and non-weight bearing. For each limb, the mid-forpaw, the wrist, the joints of the fingersr, the midfoot, the ankle and the joints of the digits are scored giving a maximum clinical score of 48 per rat. The animals are scarified on day 17 and the hindpaws are amputated and fixed in 7.4% formalin. After decalcification and embedment in paraffin, the limbs are sectioned in a mid-sagittal plane, stained by eosin and hematoxylin and examined microscopically for pannus formation (cartilage and bone erosion and destruction), vascularity (blood vessel formation by CD31 staining) and mononuclear cell infiltration (T, B and macrophages).

In CIA, DBA/1 mice that bear H-2$^q$ MHC haplotype are used as they are more susceptible to CIA. In general, heterologous collagen is used as they are more immunogenic/arthitogenic than homologous type II collagen. The mice are primed with an emulsion consisting of bovine type II collagen and Complete-Freund's Adjuvant at a 1:1 ratio (final concentration=2 mg/ml). The emulsion (0.1 ml) is injected into the tail of each mouse approximately 1-2 cm from the base. A whitish bolus beneath the dermis should be visible. A type II collagen booster (200 µg per mouse) is given intraperitoneally in PBS on day 21. High CIA-susceptible mice (DBA/1) generally develop arthritis 4-5 weeks after initial priming. Fully developed arthritis including red and swollen paws, can be observed 3-5 days after the onset and active inflammatory arthritis persists more than 3-4 weeks. Although inflammation will eventually subside, joint damage as seen as ankylosis is permanent. Assessment of CIA symptoms is essentially similar to the AIA model in which clinical signs is assigned clinical score (0-4) based on the severity of the disease. Histological measurements can also be performed on formalin-fixed joints to assess erosin, cellular infiltrates and hyperplasia.

In combined LPS-mAB induced Arthritis, a severe and consistent arthritis can be induced in mice by a combination of LPS and mAB cocktail that recognize individual epitopes clustered within an 83 amino acid peptide fragment located within CB11 region of type II collagen. This model was developed based on the hypothesis that bacterial toxin(s) absorbed through the GI tract play a synergistic and pathologic role with sub-arthritogenic levels of autoantibodies to type II collagen in triggering RA. The advantages of this model are: 1. Synchronized arthritis (100%) is induced rapidly within 7 days 2. a variety of mouse strains can be used as administration of anti-type II collagen mAB cocktail bypasses the requirement for the host's generation of autoantibodies to type II collagen thus arthritis can be induced in mice that do not possess CIA-susceptible MHC haplotypes and 3. ease of administration of mAB and LPS by either i.v. and i.p routes.

Inflammatory Bowel Diseases (IBD) which includes Crohn's disease (CD) and ulcerative colitis (UC) represents a group of chronic disorders characterized by inflammation of the gastrointestinal tract. CD can affect any part of the digestive track whereas UC affects only the colon and rectum. UC causes inflammation and ulcers usually in the sigmoid colon and rectum. Cellular infiltrates are complex and pro-inflammatory cytokines are evident in CD and UC.

An experimental model of UC is established in Balb/C mice by administration of dextran sulphate sodium (3% DSS) isolated from *Leuconostoc* spp. Into the drinking water. The experiment has a relatively short time-course (8 days) and parameters for assessment of colitis include loss of body weight, stool consistency, rectal bleeding, shortening of colonic length, crypt damage and cytokine analysis of colonic rings.

In CD, Balb/C mice are sensitized at day 0 with 2×50 µl of 5 mg/ml of dinitrofluobenzene (DNFB) epicutaneously to shaved abdomen and feet on two consecutive days. DNFB is typically solubilised in acetone: olive oil (4:1). On day 5, the mice are challenged intracolonically with 50 µl dintrobenzene sulphonic acid (DNS) at 6 mg/ml in 10% ethanol. The mice are sacrificed on day 8. Parameters to be measured include suppression of total blood cell number and cell types, mucosal mast cell protease 1 (MMCP-1) in serum, TNFα level in colon homogenate, stool consistency, vascular permeability and number of colonic patches. Number of neutorphils and mast cells which are indicative of colonic damage and cellular influx will also be assessed by histological and microscopical examinations.

Example 17

Ex Vivo Analysis in Cells from JAK2V617F Positive Patients

To assess the activity of small molecule inhibitors of JAK2 an assay has been developed to quantify the activity of the JAK-STAT pathway by measuring the phosphorylation status of the downstream protein STAT5. After ligand binding, a haemopoietic cytokine receptor undergoes conformational change activating associated JAK2 protein. Activated JAK2 then phosphorylates the intracellular portion of the receptor forming binding sites for the recruitment of intracellular signaling proteins. STAT5 is one protein that is recruited to the activated cytokine receptor complex, where it is phosphorylated and then translocates to the nucleus to regulate the expression of a suite of genes that mediate cellular growth and differentiation.

Intracellular flow cytometry can be used to measure tyrosine phosphorylated STAT5 (pYSTAT5) in specific cell populations by gating on lineage-specific haemopoietic surface markers. This is particularly important for JAK2 V617F positive myeloproliferative disease as the clone containing the mutation only forms a variable fraction of all haemopoietic cells within the bone marrow. Erythroid cells have been selected for examination in this study as this lineage is hyperplastic in PV.

Methods

Bone marrow is collected from the ileal crest of patients with JAK2 V617F positive myeloproliferative disease. Flow cytometry assays are performed on fresh bone marrow samples on the day of the biopsy procedure. Bone marrow mononuclear cells are collected by density gradient centrifugation and then 0.75-1.0×10$^6$ cells were incubated with test compounds at various concentrations for one hour in indicator-free RPMI at 37° C. Cells are maximally stimulated with erythropoietin for 10 minutes and then fixed by adding 4% formaldehyde directly into the culture medium. Cells are then permeabilised by cold methanol and then optimal concentrations of fluorescent-labeled antibodies added. Erythroid cells are selected for measurement of pYSTAT5 based on cell surface protein expression (CD45$^{lo}$, CD71$^{hi}$ population).

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:
1. A compound of formula I

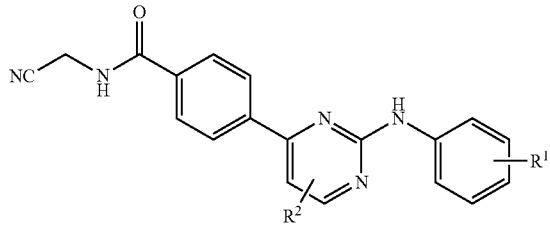

wherein
$R^1$ is a substituted or unsubstituted bicyclic heterocyclyl;
$R^2$ is selected from H, halogen, substituted or unsubstituted $C_{1-4}$ alkyl, $CF_3$ substituted or unsubstituted $C_{1-4}$ alkoxy, $CON(R)_2$, CN and $CO_2R$;
R is selected from H and substituted or unsubstituted $C_{1-4}$ alkyl,
or an enantiomer thereof or a pharmaceutically acceptable salt thereof.

2. The compound according to claim 1, wherein the compound of formula I has the formula Ia:

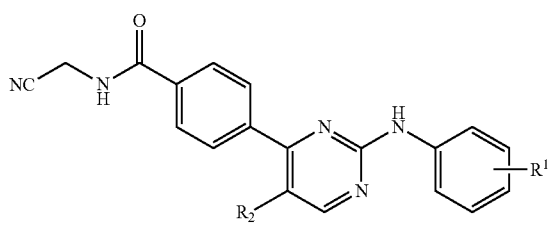

wherein,
$R^1$ and $R^2$ are as defined in claim 1,
or an enantiomer thereof or a pharmaceutically acceptable salt thereof.

3. The compound according to claim 1, wherein the compound of formula I has the formula Ib

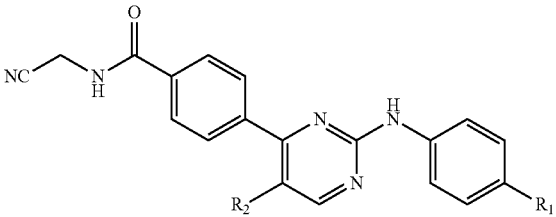

wherein $R^1$ and $R^2$ are as defined in claim 1,
or an enantiomer thereof or a pharmaceutically acceptable salt thereof.

4. A compound selected from
4-(2-((4-(1-oxa-6-azaspiro[3.3]heptan-6-yl)phenyl)amino)pyrimidin-4-yl)-N-(cyanomethyl)benzamide;
4-(2-((4-(2-oxa-6-azaspiro[3.3]heptan-6-yl)phenyl)amino)pyrimidin-4-yl)-N-(cyanomethyl)benzamide;
(S)-4-(2-((4-(1-oxa-6-azaspiro[3.4]octan-6-yl)phenyl)amino)pyrimidin-4-yl)-N-(cyanomethyl)benzamide;
(R)-4-(2-((4-(1-oxa-6-azaspiro[3.4]octan-6-yl)phenyl)amino)pyrimidin-4-yl)-N-(cyanomethyl)benzamide;
(R)-4-(2-((4(4-(1-oxa-6-azaspiro[3.5]nonan-6-yl)phenyl)amino)pyrimidin-4-yl)-N-(cyanomethyl)benzamide;
(S)-4-(2-((4-(1-oxa-6-azaspiro[3.5]nonan-6-yl)phenyl)amino)pyrimidin-4-yl)-N-(cyanomethyl)benzamide;
4-(2-((4-(1-oxa-7-azaspiro[3.5]nonan-7-yl)phenyl)amino)pyrimidin-4-yl)-N-(cyanomethyl)benzamide;
4-(2-((4-(6-oxa-3-azabicyclo [3.1.1]heptan-3-yl)phenyl)amino)pyrimidin-4-yl)-N-(cyanomethyl)benzamide;
4-(2-((4-(8-oxa-3-azabicyclo[3.2.1]octan-3-yl)phenyl)amino)pyrimidin-4-yl)-N-(cyanomethyl)benzamide;
4-(2-((4-((1S,4S)-2-oxa-5-azabicyclo[2.2.1]heptan-5-yl)phenyl)amino)pyrimidin-4-yl)-N-(cyanomethyl)benzamide; and
4-(2-((4-((1R,4R)-2-oxa-5-azabicyclo[2.2.1]heptan-5-yl)phenyl)amino)pyrimidin-4-yl)-N-(cyanomethyl)benzamide;

or an enantiomer thereof or a pharmaceutically acceptable salt thereof.

5. The compound according to claim 1 wherein the compound is a kinase inhibitor.

6. The compound according to claim 5, wherein the kinase inhibitor is a JAK1, JAK2, JAK3 and/or TYK2 inhibitor.

7. A process for the preparation of the compound of formula I according to claim 1 which comprises the step of coupling a compound of formula II

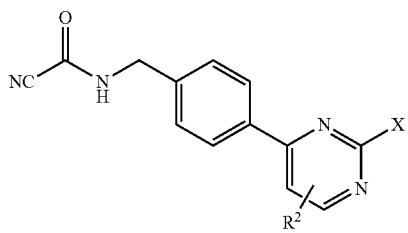

wherein
$R^2$ is defined in claim 1 and X is a leaving group with a compound of formula III

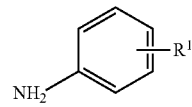

wherein
$R^1$ is defined in claim 1; and
M is B or a metal; or coupling a compound of formula IV

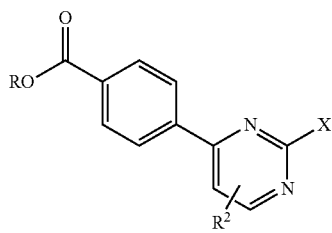

wherein
R², X and R are as defined above with a compound of formula III as defined above to prepare a compound of formula V

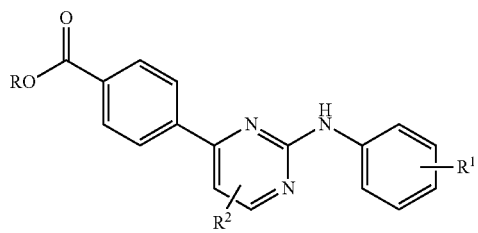

wherein
R¹, R², X and R are as defined in claim 1; and
coupling the compound of formula V defined above with

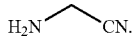

8. The process according to claim 7 wherein X in the compound of formula II is chloro which is then converted into iodo prior to coupling with the compound of formula III.

9. A pharmaceutical composition comprising the compound according to claim 1 and a pharmaceutically acceptable carrier.

10. An implant which comprises the compound according to claim 1.

11. A method for the treatment of an immunological or inflammatory disease selected from the group consisting of rheumatoid arthritis, systemic lupus erythematosis, inflammatory bowel disease, polymyalgia rheumatica, asthma, chronic obstructive pulmonary disease, and pulmonary fibrosis, which comprises administering an effective amount of the compound according to claim 1, or a pharmaceutically acceptable salt or a pharmaceutical composition thereof to a subject in need thereof.

12. A method for the treatment of a myeloproliferative disease selected from the group consisting of polycythemia vera, primary myelofibrosis, thrombocythemia, essential thrombocythemia, idiopathic myelofibrosis, chronic myelogenous leukemia, systemic mastocystosis, chronic neutrophilic leukemia, myelodisplastic syndrome, and systemic mast cell disease, which comprises administering an effective amount of the compound according to claim 1, or a pharmaceutically acceptable salt, or a pharmaceutical composition thereof to a subject in need thereof.

13. A method of inhibiting a kinase in a cell comprising contacting the cell with the compound according to claim 1.

14. A compound of formula V:

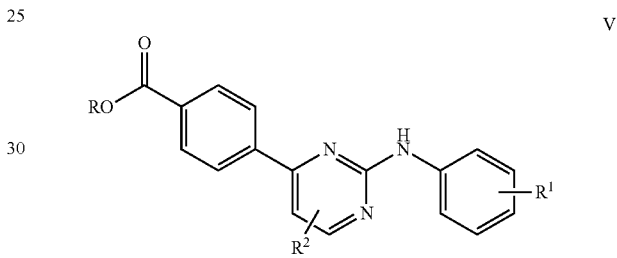

wherein
R¹ is a substituted or unsubstituted bicyclic heterocyclyl;
R² is selected from H, halogen, substituted or unsubstituted $C_{1-4}$ alkyl, $CF_3$ substituted or unsubstituted $C_{1-4}$ alkoxy, $CON(R)_2$, CN and $CO_2R$;
R is selected from H and substituted or unsubstituted $C_{1-4}$ alkyl,
or an enantiomer thereof or a pharmaceutically acceptable salt thereof.

* * * * *

UNITED STATES PATENT AND TRADEMARK OFFICE
CERTIFICATE OF CORRECTION

PATENT NO. : 8,809,359 B2  
APPLICATION NO. : 13/830152  
DATED : August 19, 2014  
INVENTOR(S) : Christopher John Burns It is certified that error appears in the above-identified patent and that said Letters Patent is hereby corrected as shown below:

In the Claims

Column 104

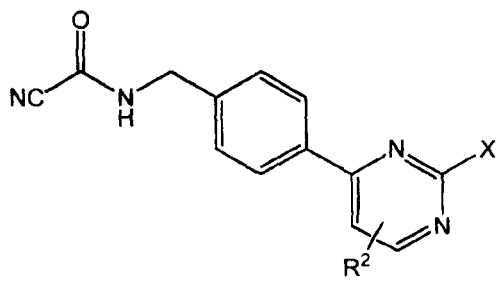

Claim 7, lines 35-50, " II "

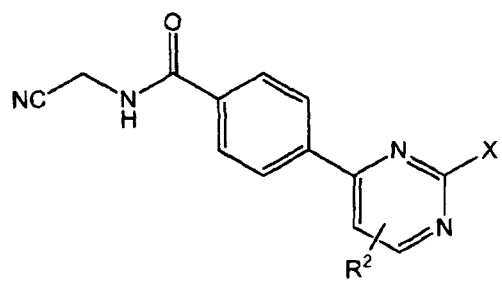

should read -- II --.

Signed and Sealed this  
Fifteenth Day of September, 2015

Michelle K. Lee  
*Director of the United States Patent and Trademark Office*

UNITED STATES PATENT AND TRADEMARK OFFICE
CERTIFICATE OF CORRECTION

PATENT NO. : 8,809,359 B2  
APPLICATION NO. : 13/830152  
DATED : August 19, 2014  
INVENTOR(S) : Christopher John Burns Page 1 of 1

It is certified that error appears in the above-identified patent and that said Letters Patent is hereby corrected as shown below:

In the Claims

Column 104  
Claim 4, lines 5-6, "(R)-4-(2-((4(4-(1-oxa-6-azaspiro[3.5]nonan-6-yl)phenyl)amino)pyrimidin-4-yl)-N-(cyanomethyl)benzamide"  
should read -- (R)-4-(2-((4-(1-oxa-6-azaspiro[3.5]nonan-6-yl)phenyl)amino)pyrimidin-4-yl)-N-(cyanomethyl)benzamide --.

Signed and Sealed this  
Fifth Day of January, 2016

Michelle K. Lee  
*Director of the United States Patent and Trademark Office*

SEQUENCE LISTING

```
<160> NUMBER OF SEQ ID NOS: 4

<210> SEQ ID NO 1
<211> LENGTH: 300
<212> TYPE: PRT
<213> ORGANISM: Homo sapiens
<220> FEATURE:
<223> OTHER INFORMATION: JAK2 Kinase j2h

<400> SEQUENCE: 1

Ser Gly Ala Phe Glu Asp Arg Asp Pro Thr Gln Phe Glu Glu Arg His
1               5                   10                  15

Leu Lys Phe Leu Gln Gln Leu Gly Lys Gly Asn Phe Gly Ser Val Glu
            20                  25                  30

Met Cys Arg Tyr Asp Pro Leu Gln Asp Asn Thr Gly Glu Val Val Ala
        35                  40                  45

Val Lys Lys Leu Gln His Ser Thr Glu Glu His Leu Arg Asp Phe Glu
    50                  55                  60

Arg Glu Ile Glu Ile Leu Lys Ser Leu Gln His Asp Asn Ile Val Lys
65                  70                  75                  80

Tyr Lys Gly Val Cys Tyr Ser Ala Gly Arg Arg Asn Leu Lys Leu Ile
                85                  90                  95

Met Glu Tyr Leu Pro Tyr Gly Ser Leu Arg Asp Tyr Leu Gln Lys His
            100                 105                 110

Lys Glu Arg Ile Asp His Ile Lys Leu Leu Gln Tyr Thr Ser Gln Ile
        115                 120                 125

Cys Lys Gly Met Glu Tyr Leu Gly Thr Lys Arg Tyr Ile His Arg Asp
    130                 135                 140

Leu Ala Thr Arg Asn Ile Leu Val Glu Asn Glu Asn Arg Val Lys Ile
145                 150                 155                 160

Gly Asp Phe Gly Leu Thr Lys Val Leu Pro Gln Asp Lys Glu Tyr Tyr
                165                 170                 175
```

-continued

```
Lys Val Lys Glu Pro Gly Glu Ser Pro Ile Phe Trp Tyr Ala Pro Glu
            180                 185                 190

Ser Leu Thr Glu Ser Lys Phe Ser Val Ala Ser Asp Val Trp Ser Phe
            195                 200                 205

Gly Val Val Leu Tyr Glu Leu Phe Thr Tyr Ile Glu Lys Ser Lys Ser
210                 215                 220

Pro Pro Ala Glu Phe Met Arg Met Ile Gly Asn Asp Lys Gln Gly Gln
225                 230                 235                 240

Met Ile Val Phe His Leu Ile Glu Leu Leu Lys Asn Asn Gly Arg Leu
                245                 250                 255

Pro Arg Pro Asp Gly Cys Pro Asp Glu Ile Tyr Met Ile Met Thr Glu
            260                 265                 270

Cys Trp Asn Asn Asn Val Asn Gln Arg Pro Ser Phe Arg Asp Leu Ala
            275                 280                 285

Leu Arg Val Asp Gln Ile Arg Asp Asn Met Ala Gly
            290                 295                 300

<210> SEQ ID NO 2
<211> LENGTH: 295
<212> TYPE: PRT
<213> ORGANISM: Homo sapiens
<220> FEATURE:
<223> OTHER INFORMATION: JAK1 Kinase j1h

<400> SEQUENCE: 2

Lys Asn Gln Pro Thr Glu Val Asp Pro Thr His Phe Glu Lys Arg Phe
1               5                   10                  15

Leu Lys Arg Ile Arg Asp Leu Gly Glu Gly His Phe Gly Lys Val Glu
            20                  25                  30

Leu Cys Arg Tyr Asp Pro Glu Asp Asn Thr Gly Glu Gln Val Ala Val
            35                  40                  45

Lys Ser Leu Lys Pro Glu Ser Gly Gly Asn His Ile Ala Asp Leu Lys
    50                  55                  60

Lys Glu Ile Glu Ile Leu Arg Asn Leu Tyr His Glu Asn Ile Val Lys
65                  70                  75                  80

Tyr Lys Gly Ile Cys Thr Glu Asp Gly Gly Asn Gly Ile Lys Leu Ile
                85                  90                  95

Met Glu Phe Leu Pro Ser Gly Ser Leu Lys Glu Tyr Leu Pro Lys Asn
            100                 105                 110

Lys Asn Lys Ile Asn Leu Lys Gln Gln Leu Lys Tyr Ala Val Gln Ile
        115                 120                 125

Cys Lys Gly Met Asp Tyr Leu Gly Ser Arg Gln Tyr Val His Arg Asp
130                 135                 140

Leu Ala Ala Arg Asn Val Leu Val Glu Ser His Gln Val Lys Ile
145                 150                 155                 160

Gly Asp Phe Gly Leu Thr Lys Ala Ile Glu Thr Asp Lys Glu Tyr Tyr
                165                 170                 175

Thr Val Lys Asp Asp Arg Asp Ser Pro Val Phe Trp Tyr Ala Pro Glu
            180                 185                 190

Cys Leu Met Gln Ser Lys Phe Tyr Ile Ala Ser Asp Val Trp Ser Phe
            195                 200                 205

Gly Val Thr Leu His Glu Leu Leu Thr Tyr Cys Asp Ser Asp Ser Ser
210                 215                 220

Pro Met Ala Leu Phe Leu Lys Met Ile Gly Pro Thr His Gly Gln Met
225                 230                 235                 240
```

Thr Val Thr Arg Leu Val Asn Thr Leu Lys Glu Gly Lys Arg Leu Pro
            245                 250                 255

Cys Pro Pro Asn Cys Pro Asp Glu Val Tyr Gln Leu Met Arg Lys Cys
            260                 265                 270

Trp Glu Phe Gln Pro Ser Asn Arg Thr Ser Phe Gln Asn Leu Ile Glu
            275                 280                 285

Gly Phe Glu Ala Leu Leu Lys
            290                 295

<210> SEQ ID NO 3
<211> LENGTH: 299
<212> TYPE: PRT
<213> ORGANISM: Homo sapiens
<220> FEATURE:
<223> OTHER INFORMATION: JAK3 Kinase j3h

<400> SEQUENCE: 3

Ala Gln Leu Tyr Ala Cys Gln Asp Pro Thr Ile Phe Glu Glu Arg His
1               5                   10                  15

Leu Lys Tyr Ile Ser Gln Leu Gly Lys Gly Asn Phe Gly Ser Val Glu
            20                  25                  30

Leu Cys Arg Tyr Asp Pro Leu Ala His Asn Thr Gly Ala Leu Val Ala
        35                  40                  45

Val Lys Gln Leu Gln His Ser Gly Pro Asp Gln Gln Arg Asp Phe Gln
    50                  55                  60

Arg Glu Ile Gln Ile Leu Lys Ala Leu His Ser Asp Phe Ile Val Lys
65                  70                  75                  80

Tyr Arg Gly Val Ser Tyr Gly Pro Gly Arg Pro Glu Leu Arg Leu Val
                85                  90                  95

Met Glu Tyr Leu Pro Ser Gly Cys Leu Arg Asp Phe Leu Gln Arg His
            100                 105                 110

Arg Ala Arg Leu Asp Ala Ser Arg Leu Leu Leu Tyr Ser Ser Gln Ile
        115                 120                 125

Cys Lys Gly Met Glu Tyr Leu Gly Ser Arg Arg Cys Val His Arg Asp
    130                 135                 140

Leu Ala Ala Arg Asn Ile Leu Val Glu Ser Glu Ala His Val Lys Ile
145                 150                 155                 160

Ala Asp Phe Gly Leu Ala Lys Leu Leu Pro Leu Asp Lys Asp Tyr Tyr
                165                 170                 175

Val Val Arg Glu Pro Gly Gln Ser Pro Ile Phe Trp Tyr Ala Pro Glu
            180                 185                 190

Ser Leu Ser Asp Asn Ile Phe Ser Arg Gln Ser Asp Val Trp Ser Phe
        195                 200                 205

Gly Val Val Leu Tyr Glu Leu Phe Thr Tyr Cys Asp Lys Ser Cys Ser
    210                 215                 220

Pro Ser Ala Glu Phe Leu Arg Met Met Gly Cys Glu Arg Asp Val Pro
225                 230                 235                 240

Ala Leu Cys Arg Leu Leu Glu Leu Leu Glu Glu Gly Gln Arg Leu Pro
                245                 250                 255

```
Ala Pro Pro Ala Cys Pro Ala Glu Val His Glu Leu Met Lys Leu Cys
            260             265                 270

Trp Ala Pro Ser Pro Gln Asp Arg Pro Ser Phe Ser Ala Leu Gly Pro
        275                 280                 285

Gln Leu Asp Met Leu Trp Ser Gly Ser Arg Gly
    290                 295

<210> SEQ ID NO 4
<211> LENGTH: 296
<212> TYPE: PRT
<213> ORGANISM: Homo sapiens
<220> FEATURE:
<223> OTHER INFORMATION: TYK2 Kinase tyk2

<400> SEQUENCE: 4

Asn Arg Asp Ser Pro Ala Val Gly Pro Thr Thr Phe His Lys Arg Tyr
1               5                   10                  15

Leu Lys Lys Ile Arg Asp Leu Gly Glu Gly His Phe Gly Lys Val Ser
            20                  25                  30

Leu Tyr Cys Tyr Asp Pro Thr Asn Asp Gly Thr Gly Glu Met Val Ala
        35                  40                  45

Val Lys Ala Leu Lys Ala Asp Cys Gly Pro Gln His Arg Ser Gly Trp
50                  55                  60

Lys Gln Glu Ile Asp Ile Leu Arg Thr Leu Tyr His Glu His Ile Ile
65                  70                  75                  80

Lys Tyr Lys Gly Cys Cys Glu Asp Gln Gly Glu Lys Ser Leu Gln Leu
                85                  90                  95

Val Met Glu Tyr Val Pro Leu Gly Ser Leu Arg Asp Tyr Leu Pro Arg
            100                 105                 110

His Ser Ile Gly Leu Ala Gln Leu Leu Leu Phe Ala Gln Gln Ile Cys
        115                 120                 125

Glu Gly Met Ala Tyr Leu His Ala His Asp Tyr Ile His Arg Asp Leu
130                 135                 140

Ala Ala Arg Asn Val Leu Leu Asp Asn Asp Arg Leu Val Lys Ile Gly
145                 150                 155                 160

Asp Phe Gly Leu Ala Lys Ala Val Pro Glu Gly His Glu Tyr Tyr Arg
                165                 170                 175

Val Arg Glu Asp Gly Asp Ser Pro Val Phe Trp Tyr Ala Pro Glu Cys
            180                 185                 190

Leu Lys Glu Tyr Lys Phe Tyr Tyr Ala Ser Asp Val Trp Ser Phe Gly
        195                 200                 205

Val Thr Leu Tyr Glu Leu Leu Thr His Cys Asp Ser Ser Gln Ser Pro
210                 215                 220

Pro Thr Lys Phe Leu Glu Leu Ile Gly Ile Ala Gln Gly Gln Met Thr
225                 230                 235                 240

Val Leu Arg Leu Thr Glu Leu Leu Glu Arg Gly Glu Arg Leu Pro Arg
                245                 250                 255

Pro Asp Lys Cys Pro Cys Glu Val Tyr His Leu Met Lys Asn Cys Trp
            260                 265                 270

Glu Thr Glu Ala Ser Phe Arg Pro Thr Phe Glu Asn Leu Ile Pro Ile
        275                 280                 285

Leu Lys Thr Val His Glu Lys Tyr
    290                 295
```